(12) United States Patent
Rodgers et al.

(10) Patent No.: US 7,544,176 B2
(45) Date of Patent: Jun. 9, 2009

(54) GLAUCOMA IMPLANT HAVING MEMS FLOW MODULE WITH FLEXING DIAPHRAGM FOR PRESSURE REGULATION

(75) Inventors: M. Steven Rodgers, Albuquerque, NM (US); Jeffry J. Sniegowski, Tijeras, NM (US); Paul J. McWhorter, Albuquerque, NM (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 439 days.

(21) Appl. No.: 11/158,144

(22) Filed: Jun. 21, 2005

(65) Prior Publication Data
US 2007/0004998 A1    Jan. 4, 2007

(51) Int. Cl.
*A61M 5/00* (2006.01)
*B01D 63/00* (2006.01)

(52) U.S. Cl. .................. 604/9; 210/321.84; 210/321.75
(58) Field of Classification Search ................ 604/4.01, 604/6.09, 264, 8, 9, 506, 6.1, 7; 210/321.84, 210/321.75, 511, 85, 500.22, 500.26; 137/115.13; 422/101
See application file for complete search history.

(56) References Cited

U.S. PATENT DOCUMENTS

| | | | |
|---|---|---|---|
| 3,159,161 A | 12/1964 | Ness | |
| 3,788,327 A | 1/1974 | Donowitz et al. | |
| 3,949,750 A | 4/1976 | Freeman | |
| 4,014,335 A | 3/1977 | Arnold | |
| 4,037,604 A | 7/1977 | Newkirk | |
| 4,168,697 A | 9/1979 | Cantekin | |
| 4,402,681 A | 9/1983 | Haas et al. | |
| 4,634,418 A | 1/1987 | Binder | |
| 4,750,901 A | 6/1988 | Molteno | |
| 4,787,885 A | 11/1988 | Binder | |
| 4,915,684 A | 4/1990 | MacKeen et al. | |

(Continued)

FOREIGN PATENT DOCUMENTS

DE    19922623 A1    12/2000

(Continued)

OTHER PUBLICATIONS

PCT Search Report dated Nov. 10, 2006; Application No. PCT/US2006/024175.

(Continued)

*Primary Examiner*—Leslie R Deak
(74) *Attorney, Agent, or Firm*—Nanette S. Thomas; James J. Murtha; Roylance, Abrams, Berdo & Goodman L.L.P.

(57) ABSTRACT

One embodiment of a MEMS flow module (34) includes a first plate (36) and a second plate (48) that are separated by a first link (62). A plurality of concentrically disposed, annular flow-restricting walls (40) extend from the first plate (36), and each is separated from the second plate (48) by a flow-restricting gap (58). When the MEMS flow module (34) is exposed to a differential pressure and in one configuration, a perimeter (46) of the first plate (36) flexes away from the second plate (48) (and at least generally about where the first link (62) interfaces with the first plate (36)) to increase the size of one or more of the flow-restricting gaps (58), to in turn accommodate an increased flow or flow rate through the MEMS flow module (34).

44 Claims, 14 Drawing Sheets

U.S. PATENT DOCUMENTS

| | | | |
|---|---|---|---|
| 4,936,825 A | 6/1990 | Ungerleider | |
| 4,959,048 A | 9/1990 | Seder et al. | |
| 4,968,296 A | 11/1990 | Ritch et al. | |
| 5,041,081 A | 8/1991 | Odrich | |
| 5,073,163 A | 12/1991 | Lippman | |
| 5,092,837 A | 3/1992 | Ritch et al. | |
| 5,127,901 A | 7/1992 | Odrich | |
| 5,273,750 A | 12/1993 | Homiger et al. | |
| 5,300,020 A | 4/1994 | L'Esperance | |
| 5,338,291 A | 8/1994 | Speckman | |
| 5,346,464 A | 9/1994 | Camras | |
| 5,372,577 A | 12/1994 | Ungerleider | |
| 5,433,701 A | 7/1995 | Rubinstein | |
| 5,454,796 A | 10/1995 | Krupin | |
| 5,558,630 A | 9/1996 | Fisher | |
| 5,626,558 A | 5/1997 | Suson | |
| 5,626,559 A | 5/1997 | Solomon | |
| 5,651,900 A * | 7/1997 | Keller et al. | 216/56 |
| 5,702,414 A | 12/1997 | Richter et al. | |
| 5,743,868 A | 4/1998 | Brown et al. | |
| 5,807,302 A | 9/1998 | Wandel | |
| 5,817,099 A | 10/1998 | Skolik et al. | |
| 5,824,086 A | 10/1998 | Silvestrini | |
| 5,868,697 A | 2/1999 | Richter et al. | |
| 5,879,319 A | 3/1999 | Pynson et al. | |
| 5,968,058 A | 10/1999 | Richter et al. | |
| 6,001,386 A | 12/1999 | Ashton et al. | |
| 6,007,511 A | 12/1999 | Prywes | |
| 6,027,470 A | 2/2000 | Mendius | |
| 6,186,974 B1 | 2/2001 | Allan et al. | |
| 6,203,513 B1 | 3/2001 | Yaron et al. | |
| 6,234,175 B1 | 5/2001 | Zhou et al. | |
| 6,261,256 B1 | 7/2001 | Ahmed | |
| 6,306,114 B1 | 10/2001 | Freeman et al. | |
| 6,450,984 B1 | 9/2002 | Lynch et al. | |
| 6,468,283 B1 | 10/2002 | Richter et al. | |
| 6,494,857 B1 | 12/2002 | Neuhann | |
| 6,508,779 B1 | 1/2003 | Suson | |
| 6,510,600 B2 | 1/2003 | Yaron et al. | |
| 6,533,768 B1 | 3/2003 | Hill | |
| 6,544,208 B2 | 4/2003 | Ethier et al. | |
| 6,544,249 B1 | 4/2003 | Yu et al. | |
| 6,558,342 B1 | 5/2003 | Yaron et al. | |
| 6,589,198 B1 | 7/2003 | Soltanpour et al. | |
| 6,595,945 B2 | 7/2003 | Brown | |
| 6,626,858 B2 | 9/2003 | Lynch et al. | |
| 6,638,239 B1 | 10/2003 | Bergheim et al. | |
| 6,666,841 B2 | 12/2003 | Gharib et al. | |
| 6,669,211 B2 | 12/2003 | Gonthier | |
| 6,699,210 B2 | 3/2004 | Williams et al. | |
| 6,699,211 B2 | 3/2004 | Savage | |
| 6,706,275 B1 | 3/2004 | Camp | |
| 6,726,664 B2 | 4/2004 | Yaron et al. | |
| 6,736,197 B2 | 5/2004 | Nozaki et al. | |
| 6,736,791 B1 | 5/2004 | Tu et al. | |
| 6,780,164 B2 | 8/2004 | Bergheim et al. | |
| 6,827,699 B2 | 12/2004 | Lynch et al. | |
| 6,827,700 B2 | 12/2004 | Lynch et al. | |
| 6,881,197 B1 | 4/2005 | Nigam | |
| 6,881,198 B2 * | 4/2005 | Brown | 604/8 |
| 6,955,656 B2 | 10/2005 | Bergheim et al. | |
| 6,981,958 B1 | 1/2006 | Gharib et al. | |
| 7,226,540 B2 * | 6/2007 | Rodgers et al. | 210/321.84 |
| 2002/0013546 A1 | 1/2002 | Grieshaber et al. | |
| 2002/0128560 A1 | 9/2002 | Urich | |
| 2002/0143284 A1 | 10/2002 | Tu et al. | |
| 2002/0169130 A1 | 11/2002 | Tu et al. | |
| 2002/0177856 A1 | 11/2002 | Richter et al. | |
| 2002/0188308 A1 | 12/2002 | Tu et al. | |
| 2003/0055372 A1 | 3/2003 | Lynch et al. | |
| 2003/0060752 A1 | 3/2003 | Bergheim et al. | |
| 2003/0069637 A1 | 4/2003 | Lynch et al. | |
| 2003/0088260 A1 | 5/2003 | Smedley et al. | |
| 2003/0181848 A1 | 9/2003 | Bergheim et al. | |
| 2003/0187384 A1 | 10/2003 | Bergheim et al. | |
| 2003/0187385 A1 | 10/2003 | Bergheim et al. | |
| 2003/0191428 A1 | 10/2003 | Bergheim et al. | |
| 2003/0220602 A1 | 11/2003 | Lynch et al. | |
| 2003/0229303 A1 | 12/2003 | Haffner et al. | |
| 2003/0232015 A1 | 12/2003 | Brown et al. | |
| 2003/0236483 A1 | 12/2003 | Ren | |
| 2004/0015140 A1 | 1/2004 | Shields | |
| 2004/0024345 A1 | 2/2004 | Gharib et al. | |
| 2004/0073231 A1 | 4/2004 | Juan et al. | |
| 2004/0088048 A1 | 5/2004 | Richter et al. | |
| 2004/0102729 A1 | 5/2004 | Haffner et al. | |
| 2004/0111050 A1 | 6/2004 | Smedley et al. | |
| 2004/0127843 A1 | 7/2004 | Tu et al. | |
| 2004/0193095 A1 | 9/2004 | Shadduck | |
| 2004/0210181 A1 | 10/2004 | Vass et al. | |
| 2004/0225250 A1 | 11/2004 | Yablonski | |
| 2004/0249333 A1 | 12/2004 | Bergheim et al. | |
| 2004/0254517 A1 | 12/2004 | Quiroz-Mercado et al. | |
| 2004/0254521 A1 | 12/2004 | Simon | |
| 2004/0260228 A1 | 12/2004 | Lynch et al. | |
| 2005/0038334 A1 | 2/2005 | Lynch et al. | |
| 2005/0049578 A1 | 3/2005 | Tu et al. | |
| 2005/0090806 A1 | 4/2005 | Lynch et al. | |
| 2005/0090807 A1 | 4/2005 | Lynch et al. | |
| 2005/0119601 A9 | 6/2005 | Lynch et al. | |
| 2005/0119636 A1 | 6/2005 | Haffner et al. | |
| 2005/0125003 A1 | 6/2005 | Pinchuk et al. | |
| 2005/0148925 A1 | 7/2005 | Rottenberg et al. | |
| 2005/0184003 A1 | 8/2005 | Rodgers et al. | |
| 2005/0184004 A1 | 8/2005 | Rodgers et al. | |
| 2005/0194303 A1 | 9/2005 | Sniegowski et al. | |
| 2005/0197613 A1 | 9/2005 | Sniegowski et al. | |
| 2005/0197653 A1 | 9/2005 | Sniegowski et al. | |
| 2005/0209549 A1 | 9/2005 | Bergheim et al. | |
| 2005/0209550 A1 | 9/2005 | Bergheim et al. | |
| 2005/0266047 A1 | 12/2005 | Tu et al. | |
| 2005/0267398 A1 | 12/2005 | Protopsaltis et al. | |
| 2005/0268722 A1 | 12/2005 | Tai et al. | |
| 2005/0271704 A1 | 12/2005 | Tu et al. | |
| 2005/0273033 A1 | 12/2005 | Grahn et al. | |
| 2005/0288617 A1 | 12/2005 | Yaron | |
| 2005/0288619 A1 | 12/2005 | Gharib et al. | |

FOREIGN PATENT DOCUMENTS

| | | |
|---|---|---|
| DE | 19922623 C2 | 12/2000 |
| WO | WO 01/50943 A2 | 7/2001 |
| WO | WO 01/50943 A3 | 7/2001 |
| WO | WO0150943 | 7/2001 |
| WO | WO 01/99175 A1 | 12/2001 |
| WO | WO 03/092564 A1 | 11/2003 |
| WO | WO 2005/081967 | 9/2005 |
| WO | WO 2005/081968 | 9/2005 |
| WO | WO2005081967 | 9/2005 |
| WO | WO 2005/105197 | 11/2005 |

OTHER PUBLICATIONS

Tae Seok Sim and Yong-Kweon Kim; A Study on The Passive Microvalve Applicable To Drainage Device For Glaucoma; Journal of Semiconductor Technology And Science, vol. 2., No. 4. Dec. 2002.

Spiegel, D.; Scheffthaler M.; Kobuch, K.; Outflow Facilities Through Descemet's Membrane in Rabbits; Graefes Arch Clin Exp Ophthalmol Feb. 2000 240 (2):111-3.

[No Authors listed] Krupin Eye Value With Disk For Filtration Surgery. The Krupin Eye Valve Filtering Surgery Study Group. Ophthalmology. Apr. 1994; 101(4):651-8.

Agfid Project Team; Cell and Protein Adhesion Studies In Glaucoma Drainage Device Development; Br. J. Ophthalmol. 1999; 83; 1168-1171.

Bruce Allan; Closer To Nature: New Biomaterials and Tissue Engineering In Ophthalmology; Br. J. Ophthalmol 1999; 1235-1240.

Agfid Project Team; Experimental Flow Studies in Glaucoma Drainage Device Development; Br. J. Ophthalmol 2001; 85; 1231-1236.

Yael Hanein; Y. Vickie Pan; Buddy D. Ratner; Denice D. Denton; Karl F. Bohringer; Micromachining of Non-Fouling Coatings For Bio-Mems Applications; Sensors & Actuators B 81, 2001.

Patty Chen; Eugene Lim; Kin-Joe Sham; Adiel Smith; and Patrick Willoughby; FDA Report: Smartflow Glaucoma Stent; Jan. 9, 2003 Submitting To Myron Spector & I.V. Yannas.

K.S. Lim, B.D.S. Allan, AW Lloyd, A Muir, PT Khaw; Glaucoma Drainage Devices; Past, Present and Future; Br. J. Ophthalmol 1998;82; 1083-1089.

D.J. Howorth; Feasibility Study For A Micromachined Glaucoma Drainage Device; MSc Thesis From Cranfield University 2001-2002; Sep. 13, 2002.

Cristina Rodica Neau, A Medical Microactuator Based on an Electrochemical Principle. Sep. 4, 1966; Roemania.

* cited by examiner

GLAUCOMA IMPLANT HAVING MEMS FLOW MODULE WITH FLEXING DIAPHRAGM FOR PRESSURE REGULATION

FIELD OF THE INVENTION

The present invention generally relates to the field of microfabricated devices and, more particularly, to an implant having a MEMS flow module that utilizes a flexing diaphragm to provide at least a pressure regulation function.

BACKGROUND OF THE INVENTION

High internal pressure within the eye can damage the optic nerve and lead to blindness. There are two primary chambers in the eye—an anterior chamber and a vitreous body that are generally separated by a lens. Aqueous humor exists within the anterior chamber, while vitreous humor exists in the vitreous body. Generally, an increase in the internal pressure within the eye is caused by more fluid being generated within the eye than is being discharged by the eye. The general consensus is that it is excess fluid within the anterior chamber of the eye that is the main contributor to an elevated intraocular pressure.

One proposed solution to addressing high internal pressure within the eye is to install an implant. Implants are typically directed through a wall of the patient's eye so as to fluidly connect the anterior chamber with an exterior location to the eye. There are a number of issues with implants of this type. One is the ability of the implant to respond to changes in the internal pressure within the eye in a manner that reduces the potential for damaging the optic nerve. Another is the ability of the implant to reduce the potential for bacteria and the like passing through the implant and into the interior of the patient's eye, for instance into the anterior chamber.

BRIEF SUMMARY OF THE INVENTION

The present invention is generally embodied by what may be characterized as a MEMS flow module that provides at least a pressure regulation function. The use of the term "flow" in the description of the invention does not mean or require that a flow regulation function be provided in the form of providing a certain or a desired flow rate. Instead, the term "flow" is used in the description of the invention simply to identify that the invention accommodates a flow through the MEMS module, for instance to accommodate a different flow to provide a desired pressure regulation function.

A first aspect of the present invention is embodied by an implant for addressing pressure within a first body region. The implant includes a conduit that has a flow path, and the conduit is adapted to fluidly interconnect with the first body region. At least one MEMS flow module is associated with this flow path, and includes first and second layers or plates that are spaced from each other, as well as at least one first flow-restricting structure. The first plate includes at least one first flow port, while the second plate includes at least one second flow port. The first flow-restricting structure extends from one of the first and second plates in the direction of the other of the first and second plates. A spacing between the first flow-restricting structure and either the first or second plate defines a first flow restriction (i.e., if the first flow-restricting structure extends from the first plate, the first flow-restricting structure and the second plate will collectively define the noted first flow restriction; if the first flow-restricting structure extends from the second plate, the first flow-restricting structure and the first plate will collectively define the noted first flow restriction). At least one dimension of the first flow restriction changes based upon at least one of the first and second plates flexing in response to the existence or development of at least a certain differential pressure across the MEMS flow module. Another characterization is that a flow resistance of the first flow restriction changes based upon the noted flexing.

Various refinements exist of the features noted in relation to the first aspect of the present invention. Further features may also be incorporated in the first aspect of the present invention as well. These refinements and additional features may exist individually or in any combination. The term "implant," as used herein, means a device that is at least partially disposed within an appropriate biological mass. The entire implant could be disposed within a biological mass. Another option would be for part of the implant to be disposed within a biological mass, and for another part of the implant to be disposed externally of the biological mass or at least provide for fluid communication externally of the biological mass (e.g., by interfacing with the environment).

The implant may be used for any appropriate application, may be installed in any appropriate biological mass, and may be installed at any appropriate location within such a biological mass. In this regard, the implant conduit may be of any appropriate size, shape, and configuration, or otherwise may be adapted for the targeted application. In one embodiment, the first body region is the anterior chamber of an eye. One example would be to dispose one or more of the noted MEMS flow modules in a conduit extending between the anterior chamber of an eye and a location that is exterior of the cornea of the eye. Another example would be to dispose one or more of the noted MEMS flow modules in a conduit extending between the anterior chamber of an eye and another location that is exterior of the sclera of the eye. Yet another example would be to dispose one or more of these MEMS flow modules in a conduit extending between the anterior chamber of an eye and another location within the eye (e.g., into Schlemm's canal) or body. In any case, any of these MEMS flow modules could be disposed directly into such a conduit, or one or more housings could be used to integrate any of these MEMS flow modules with the conduit. In each of these examples, the conduit would provide an exit path for aqueous humor when installed for a glaucoma patient. That is, each of these examples may be viewed as a way of treating glaucoma or providing at least some degree of control of the intraocular pressure.

Any appropriate coating may be applied to various surfaces of the MEMS flow module and/or any housing associated therewith, including without limitation a coating that improves biocompatibility, that makes such surfaces more hydrophilic, and/or that reduces the potential for bio-fouling. In one embodiment, a self-assembled monolayer coating (e.g., poly-ethylene-glycol) is applied in any appropriate manner (e.g., liquid or vapor phase, with vapor phase being the preferred technique) to all exposed surfaces of the MEMS flow module and any housing that integrates the MEMS flow module for positioning within the conduit.

As noted, one or more housings may be used to integrate the MEMS flow module with the conduit in the case of the first aspect. For instance, the MEMS flow module could be disposed on the end of or within a housing (e.g., in accordance with the outer housing discussed below), that in turn is at least partially disposed within the conduit of the implant. Another option would be for a first inner housing to be at least partially disposed within an outer housing having a first flow path, for the MEMS flow module to be mounted on or disposed adjacent to the first inner housing such that all flow through the first flow path is directed through the MEMS flow module, and for the outer housing to be at least partially disposed within the conduit of the implant. The outer housing and first inner housing may provide structural integrity for the MEMS flow module, and further may protect the MEMS flow module. In this regard, both the outer housing and first inner housing may be rigid structures, or at least may be more rigid than the MEMS flow module. Representative materials from which both the outer housing and the first inner housing may be formed include without limitation polymethylmethacrylate (PMMA), ceramics, silicon, titanium, and other implantable metals and plastics.

Both the outer housing and the first inner housing may be of any appropriate shape (e.g., a cylinder). Typically the outer housing will be adapted in some manner for disposition at least partially within the conduit, while the first inner housing will be adapted in some manner for disposition at least partially within the outer housing. For instance, the outer housing may be disposed about the first inner housing along the entire length of the first inner housing (e.g., each end of the first inner housing may be flush with or recessed inwardly from the corresponding end of the outer housing), or only along a portion of the length of the first inner housing (e.g., one or both ends of the first inner housing may extend beyond the corresponding end of the outer housing).

The first inner housing is preferably maintained in a stationary or fixed position relative to the outer housing in the case of the first aspect. For instance, the first inner housing may be bonded to the outer housing, a press fit may be utilized between the outer housing and first inner housing, the outer housing may be shrink-fitted about the first inner housing, or any combination thereof. A second inner housing may also be at least partially disposed within the outer housing, with the MEMS flow module being located between adjacent ends of the first inner housing and second inner housing, and preferably mounted to at least one of the first inner housing and second inner housing. Such a second inner housing is also preferably maintained in a stationary or fixed position relative to the outer housing in the same manner as the first inner housing.

Additional characterizations may be made in relation to incorporating the MEMS flow module using an outer housing and first inner housing in the case of the first aspect. The MEMS flow module may be recessed within the first inner housing. Consider the case where the first inner housing includes first and second ends, and where the first flow path extends between these first and second ends. The MEMS flow module may be located anywhere between these first and second ends. Another option would be for the MEMS flow module to be mounted on the first or second end of the first inner housing.

Any appropriate way of mounting the MEMS flow module to the first inner housing may be used in the case of the first aspect. For instance, the MEMS flow module may be bonded to the first inner housing, there may be a press fit between the MEMS flow module and the first inner housing, or both. In any case, preferably the MEMS flow module is maintained in a fixed position relative to the first inner housing.

The first and second plates of the MEMS flow module of the first aspect, as well as the first and second flow ports, each may be of any appropriate size, shape, and configuration. In one embodiment, both the first and second plates are defined by at least one layer, where each layer has a thickness within a range of about 1 micron to about 3 microns. The first and second plates may be structurally interconnected in any appropriate manner that allows at least part of at least one of the first and second plates to flex for purposes of changing at least one dimension of the first flow restriction and/or the flow resistance of the first flow restriction.

At least one of the first and second plates flexes in response to the existence or development of at least a certain differential pressure across the MEMS flow module as noted. Although this "certain differential pressure" may be of any appropriate magnitude, preferably the noted flexing occurs anytime the differential pressure is greater than zero, and furthermore preferably the flexing occurs anytime there is any change in the differential pressure. All references herein to a "certain differential pressure" or the like will be in accordance with the foregoing unless otherwise noted. Preferably, the flow rate through the MEMS flow module increases by the noted flexing increasing the size of the noted spacing.

The first flow-restricting structure of the MEMS flow module may extend from the first plate and terminate prior to reaching the second plate. However, the first flow-restricting structure could be spaced in any appropriate manner from the second plate to provide a first flow restriction. The first flow-restricting structure may be of any appropriate size, shape, and/or configuration, for instance, annular or in the form of a solid plug or the like that is disposed over or even within a flow port. "Annular" in relation to the first flow-restricting structure, as well as any other component described herein as being "annular," means that the particular structure extends a full 360 degrees about a common reference point, and thereby does not limit the particular structure to having a circular configuration. For instance, square-shaped, rectangular-shaped, and elliptical-shaped are other representative annular configurations.

A single first flow-restricting structure could be utilized. Alternatively, a plurality of first flow-restricting structures could be utilized, with each first flow-restricting structure having a corresponding first flow restriction. In either case, at least some of the flow should be required to pass through at least one flow restriction (for instance, a first flow restriction) in order to progress completely through the MEMS flow module. The MEMS flow module may include one or more etch release holes or the like that would allow part of the flow to bypass the first flow restriction(s). In one embodiment where a plurality of first flow-restricting structures are used, all that is required is for at least some of the flow to pass through only one flow restriction in order to progress completely through the MEMS flow module. Although at least one dimension of each first flow restriction could and likely will change by the flexing of the first and/or second plate in response to a differential pressure, the first aspect encompasses having only one of a plurality of first flow restrictions undergo the noted change.

Consider the case where each first flow-restricting structure extends along at least part of one of a plurality of at least generally concentrically disposed reference circles. At least one first flow-restricting structure may be associated with each reference circle. Each reference circle could include a single first flow-restricting structure (e.g., "annular" in accordance with the following) or a plurality of first flow-restricting structures that are appropriately spaced from each other in the manner disclosed in commonly assigned U.S. patent application Ser. No. 11/095,995, that is entitled, "MEMS FILTER MODULE WITH CONCENTRIC FILTERING WALLS," that was filed on Mar. 31, 2005, and the entire disclosure of which is incorporated by reference in its entirety herein, could be utilized as well. Adjacent first flow-restricting structures that are disposed along a common reference circle could be separated by the same size of gap as the size of the spacing that defines the first flow restriction when there is no differential pressure across the MEMS flow module. In any case, a plurality of first and second flow ports may be arranged such that a flow through any first flow port will have to flow through a flow restriction before reaching any second flow port, and vice versa (e.g., one or more first flow ports and one or more second flow ports may be disposed in alternating relation between pairs of adjacent, annular flow-restricting structures).

One or more of the noted first flow-restricting structures may be annular as noted, including having each first flow-restricting structure of the MEMS flow module be annular. In one embodiment, each of the plurality of first flow-restricting structures is concentrically disposed, and each adjacent pair of such annular first flow-restricting structures may be equally spaced from each other, although such is not required. The spacing between a particular adjacent pair of such annular first flow-restricting structures may be constant or otherwise about their entire annular extent as well. Other appropriate arrangements may be employed when having a plurality of annular first flow-restricting structures. For instance, a plurality of annular first flow-restricting structures may be disposed about a common point without being concentrically disposed (i.e., each first flow-restricting structure may extend completely about any adjacent first flow-restricting structure that is disposed inwardly thereof, but without being concentric relative thereto). A plurality of annular first flow-restricting structures could also be arranged such that each annular first flow-restricting structure encompasses its own region, or such that no two annular first flow-restricting structures encompass a common region. It should be appreciated that any annular first flow-restricting structure could be replaced by a plurality of flow-restricting segments that collectively define an annular arrangement or configuration, and where adjacent flow-restricting segments are appropriately spaced from each other.

A first embodiment of the MEMS flow module associated with the first aspect utilizes a first plate with a first region and a second region that extends from the first region to a perimeter of the first plate (e.g., the second region may be disposed about or surround the first region), as well as a second plate with a third region and a fourth region that extends from the third region to a perimeter of the second plate (e.g., the fourth region may be disposed about or surround the third region). The second region of the first plate includes a plurality of first flow ports, while the third region of the second plate includes a plurality of second flow ports. A single or multiple first flow-restricting structures could be utilized by this first embodiment in association with the various first and second flow ports and in accordance with the foregoing. In any case, a first link of any appropriate size, shape, and configuration extends between the first and second plates so as to interface with the first plate within its first region, and further so as to interface with the second plate within its third region.

The first region of the first plate may be defined as that which encompasses each structural interconnection between the first and second plates (e.g., the second region of the first plate may be free to flex to at least a certain degree relative to the second plate, and/or may be characterized as being free of any fixed, structural interconnection with the second plate). The second plate may be characterized as being spaced from the first plate in a first direction, with a second direction being opposite of this first direction. The fourth region of the second plate is at least substantially maintained in a fixed orientation relative to the structure(s) of the MEMS flow module that flexes to provide a pressure regulation function (e.g., such that the fourth region of the second plate does not flex or otherwise change shape to any significant degree). Typically, the first region of the first plate will be at least substantially maintained in a fixed orientation relative to the second region of the first plate as well (e.g., such that the first region of the first plate does not flex or otherwise change shape to any significant degree).

There are a number of options in which flexing may be provided in relation to the first embodiment of the MEMS flow module to provide a pressure regulation function. The second region of the first plate (e.g., an "outer" region) may flex relative to the first region of the first plate (e.g., an "inner" region) in the second direction (at least generally away from the second plate) in response to the development of at least a certain differential pressure across the MEMS flow module to change at least one dimension of at least one first flow restriction and/or decrease the flow resistance of at least one first flow restriction in a manner that accommodates an increased flow or flow rate through the MEMS flow module. The surface of the first plate that is opposite that which faces the second plate may become at least generally cup-shaped when the second region of the first plate flexes in the second direction. When the first plate flexes in the second direction, the entire second plate may be at least substantially maintained in a fixed orientation (e.g., such that the entire second plate does not flex or otherwise change shape to any significant degree), or stated another way the entire second plate may remain at least substantially stationary. When the first plate flexes in the second direction, the third region of the second plate (e.g., an "inner" region) may also flex relative to the fourth region of the second plate (e.g., an "outer" region) and in the second direction (toward the first plate) in response to the development of at least a certain differential pressure across the MEMS flow module to also contribute to changing at least one dimension of at least one first flow restriction and/or decreasing the flow resistance of at least one first flow restriction in a manner that accommodates an increased flow or flow rate through the MEMS flow module.

Another option in which flexing may be provided in relation to the first embodiment of the MEMS flow module to provide a pressure regulation function is to at least substantially maintain the entire first plate in a fixed orientation (e.g., such that the entire first plate does not flex or otherwise change shape to any significant degree). In this case, the third region of the second plate (e.g., an "inner" region) may flex relative to the fourth region of the second plate (e.g., an "outer" region), and in the second direction, in response to the development of at least a certain differential pressure across the MEMS flow module to change at least one dimension of at least one first flow restriction and/or decrease the flow resistance of at least one first flow restriction in a manner that accommodates an increased flow or flow rate through the MEMS flow module.

The first embodiment of the MEMS flow module may include first and second fabrication levels. The term "fabrication level" is addressed in more detail below. The first plate and the first flow-restricting structure may exist at least in the first fabrication level, the second plate may exist at least in the second fabrication level, and the first flow-restricting structure may extend from the first plate in the direction of the second plate. Alternatively, the first plate may exist at least in the first fabrication level, the second plate and the first flow-restricting structure may exist at least in the second fabrication level, and the first flow-restricting structure may extend from the second plate in the direction of the first plate.

The first plate may be smaller than the second plate in the case of the first embodiment of the MEMS flow module. One characterization in this regard is that the perimeter of the first plate is disposed inwardly of the perimeter of the second plate. Another characterization in this regard is that a projection of the first plate onto the second plate defines a region that encompasses each of the various second flow ports associated with the second plate, and the entirety of the perimeter of the second plate is disposed outwardly or further beyond this projection region.

A second embodiment of a MEMS flow module utilizes first and second plates, each having first and second regions. The first region of the first plate in this case is disposed about or surrounds the second region of the first plate, while the first region of the second plate is disposed about or surrounds the second region of the second plate. The first plate includes a plurality of first flow ports at least within the second region of the first plate, while the second plate includes a plurality of second flow ports at least within the second region of the second plate. A single or multiple first flow-restricting structures could be utilized by this second embodiment in association with the various first and second flow ports and in accordance with the foregoing. Each first flow-restricting structure is disposed within the second region of either the first or second plate (e.g., an "inner" region). The first region of both the first and second plates (e.g., an "outer" region) is maintained in an at least substantially fixed orientation in the second embodiment (e.g., such that the first region of both the first and second plates does not flex or otherwise change shape to any significant degree). Flexing of the first and/or second plate within its corresponding second region in response to the development of at least a certain differential pressure across the MEMS flow module will change at least one dimension of at least one first flow restriction and/or decrease the flow resistance of at least one first flow restriction in a manner that accommodates an increased flow or flow rate through the MEMS flow module.

The first region of the first and second plates (e.g., an "outer" region) may be maintained in an at least substantially fixed orientation (e.g., such that the first region of both the first and second plates does not flex or otherwise change shape to any significant degree) in any appropriate manner. One or more structural interconnects of any appropriate size, shape, configuration, and arrangement may extend between the first region of the first plate and the first region of the second plate to provide this function. In one embodiment, such a structural interconnect is in the form of a plurality of columns, posts, or the like. In another embodiment, at least one annular wall extends between the first region of the first plate and the first region of the second plate. Such an annular wall would thereby also provide at least one radial seal (e.g., to reduce the potential of a flow exiting the MEMS flow module through the space between the first and second plates). A plurality of columns, posts, or the like could be used in combination with at least one annular wall within the first region of the first and second plates as well.

Consider the case where the second plate is spaced from the first plate in a first direction in relation to the second embodiment of the MEMS flow module. The MEMS flow module may be oriented so that the first plate is on the high-pressure side of the MEMS flow module and so that the second plate is on the low-pressure side of the MEMS flow module. The second region of the second plate (e.g., an "inner" region) may flex at least generally in the first direction (or away from the first plate) in response to the development of at least a certain differential pressure across the MEMS flow module to change at least one dimension of at least one first flow restriction and/or decrease the flow resistance of at least one first flow restriction in a manner that accommodates an increased flow or flow rate through the MEMS flow module. The entire first plate may be at least substantially maintained in a fixed orientation (e.g., such that the entire first plate does not flex or otherwise change shape to any significant degree), or the second region of the first plate (e.g., an "inner" region) could also flex to at least a certain degree in the first direction, but not to the same extent as the second plate. Flexing of the second region of the first plate in this manner will still allow for a change in at least one dimension of at least one first flow restriction and/or a decrease in the flow resistance of at least one first flow restriction in a manner that accommodates an increased flow or flow rate through the MEMS flow module, but not to the same degree when compared to when the entire first plate remains in an at least substantially fixed orientation.

The second embodiment of the MEMS flow module also may include first and second fabrication levels. The term "fabrication level" again is addressed in more detail below. The first plate and the first flow-restricting structure may exist at least in the first fabrication level, the second plate may exist at least in the second fabrication level, and the first flow-restricting structure may extend from the first plate in the direction of the second plate. Alternatively, the first plate may exist at least in the first fabrication level, the second plate and the first flow-restricting structure may exist at least in the second fabrication level, and the first flow-restricting structure may extend from the second plate in the direction of the first plate.

A third embodiment of a MEMS flow module is a variation of the above-noted second embodiment, where the first region of the first plate (e.g., an "outer" region) also includes a plurality of first flow ports, where the first region of the second plate (e.g., an "outer" region) also includes a plurality of second flow ports, and where at least one second flow-restricting structure is associated with the first region of the first and second plates. Each such second flow-restricting structure extends from the first region of the first plate in the direction of the first region of the second plate and is spaced from the second plate, or vice versa. In either case, this spacing associated with each second flow-restricting structure defines a second flow restriction. Since the first regions of the first and second plates are maintained in an at least substantially fixed orientation (e.g., such that the first region of both the first and second plates does not flex or otherwise change shape to any significant degree), the second flow restriction associated with each second flow-restricting structure is of a fixed magnitude (e.g., does not change to any significant degree during flexing of the first and/or second plates in response to the MEMS flow module experiencing a differential pressure). Therefore, this third embodiment may be characterized as a MEMS flow module having both a fixed filter section (having one or more second flow-restricting structures) and a pressure regulator section (having one or more first flow-restricting structures). The various features that are discussed in relation to the second aspect may be utilized by this third embodiment of the first aspect as well, individually or in any combination.

A fourth embodiment of a MEMS flow module utilizes first and second plates, each having first and second regions. The first region of the first plate is disposed about or surrounds the second region of the first plate, while the first region of the second plate is disposed about or surrounds the second region of the second plate. The first flow port is disposed within the second region of the first plate, and the second flow port is disposed within the second region of the second plate. The first flow-restricting structure is disposed about at least part of the first flow port and extends from the first plate toward the second plate, but remains spaced from the second plate to define a first flow restriction. The first flow-restricting structure in this case is either annular, or in the form of a plurality of appropriately spaced first flow-restricting segments that are collectively disposed about the entire perimeter of the first flow port. In one embodiment, such a first flow-restricting structure(s) is associated with a single first flow port, and this single first flow port has an area of at least about 2,000 µm² (in plan view or within a plane that is normal to the flow therethrough). The second flow port is located so as to be disposed beyond a projection of an annular first flow-restricting structure onto the second plate. Multiple second flow ports could be disposed in this same relative position as well. In one embodiment, the first regions of the first and second plates (e.g., an "outer" region) are each maintained in an at least substantially fixed orientation (e.g., such that the first region of both the first and second plates does not flex or otherwise change shape to any significant degree), including in the manner discussed above in relation to the second embodiment. One or more second flow-restricting structures could also be disposed within the first region of the first and/or second plate in the manner discussed above in relation to the third embodiment as well.

Consider again the case where the second plate is spaced from the first plate in a first direction for the fourth embodiment of the MEMS flow module. The MEMS flow module may be oriented so that the first plate is on the high-pressure side of the MEMS flow module and so that the second plate is on the low-pressure side of the MEMS flow module. The second region of the second plate (e.g., an "inner" region) may flex at least generally in the first direction (or away from the first plate) in response to the development of at least a certain differential pressure across the MEMS flow module to change at least one dimension of the first flow restriction and/or decrease the flow resistance of the first flow restriction in a manner that accommodates an increased flow or flow rate through the MEMS flow module. The entire first plate may be at least substantially maintained in a fixed orientation (e.g., such that the entire first plate does not flex or otherwise change shape to any significant degree), or the second region of the first plate (e.g., an "inner" region) could also flex to at least a certain degree in the first direction, but not to the same extent as the second plate. Flexing of the first plate in this manner will still allow for a change in at least one dimension of the first flow restriction and/or a decrease in the flow resistance of the first flow restriction in a manner that accommodates an increased flow or flow rate through the MEMS flow module, but not to the same degree when compared to when the entire first plate remains in an at least substantially fixed orientation.

The fourth embodiment of the MEMS flow module could also be oriented so that the second plate is on the high-pressure side of the MEMS flow module and so that the first plate is on the low-pressure side of the MEMS flow module. The second region of the first plate (e.g., an "inner" region) may flex at least generally in a second direction that is opposite of the first direction (e.g., to move at least generally away from the second plate) in response to the development of at least a certain differential pressure across the MEMS flow module to change at least one dimension of the first flow restriction and/or decrease the flow resistance of the first flow restriction in a manner that accommodates an increased flow or flow rate through the MEMS flow module. The entire second plate may be at least substantially maintained in a fixed orientation (e.g., such that the entire second plate does not flex or otherwise change shape to any significant degree), or the second region of the second plate (e.g., an "inner" region) could also flex to at least a certain degree in the second direction, but not to the same extent as the first plate. Flexing of the second plate in this manner will still allow for a change in at least one dimension of the first flow restriction and/or a decrease in the flow resistance of the first flow restriction in a manner that accommodates an increased flow or flow rate through the MEMS flow module, but not to the same degree when compared to when the entire second plate remains in an at least substantially fixed orientation.

The fourth embodiment of the MEMS flow module also may include first and second fabrication levels. The term "fabrication level" again is addressed in more detail below. The first plate and the first flow-restricting structure may exist at least in the first fabrication level, the second plate may exist at least in the second fabrication level, and the first flow-restricting structure may extend from the first plate in the direction of the second plate.

A second aspect of the present invention is embodied by an implant for addressing pressure within a first body region. The implant includes a conduit that has a flow path, and the conduit is adapted to fluidly interconnect with the first body region. At least one MEMS flow module is associated with this flow path, and includes first and second layers or plates that are spaced from each other. The first plate includes first and second regions, where the first region of the first plate is disposed about or surrounds the second region of the first plate, where the first and second regions of the first plate each include at least one and more typically a plurality of first flow ports, where the first region of the first plate includes at least one first flow-restricting structure, and where the second region of the first plate includes at least one second flow-restricting structure. The second plate includes first and second regions, where the first region of the second plate is disposed about or surrounds the second region of the second plate, and where each of the first and second regions of the second plate includes at least one and more typically a plurality of second flow ports. Each of the first and second flow-restricting structures extend from the first plate at least generally in the direction of the second plate, but remain spaced from the second plate so as to define a flow restriction (a first flow restriction in the case of a first flow-restricting structure, and a second flow restriction in the case of a second flow-restricting structure). The first region of the first plate and the first region of the second plate (e.g., an "outer" region) are each maintained in an at least substantially fixed orientation (e.g., such that the first region of both the first and second plates does not flex or otherwise change shape to any significant degree), while the second region of at least one of the first and second plates will flex in response to the development of at least a certain differential pressure across the MEMS flow module. This flexing changes at least one dimension of at least one second flow restriction and/or the flow resistance of at least one second flow restriction, and thereby encompassing changing at least one dimension of each second flow restriction and/or the flow resistance of each second flow restriction.

Various refinements exist of the features noted in relation to the second aspect of the present invention. Further features may also be incorporated in the second aspect of the present invention as well. These refinements and additional features may exist individually or in any combination. One or both of the first and second plates may flex in the manner discussed above in relation to the third embodiment of the first aspect, and the MEMS flow module may be configured such that either the first or second plate is exposed to the high-pressure source. The various features discussed above in relation to the third embodiment of the first aspect may be used in relation to the second aspect, individually or in any combination. More generally, the first aspect is applicable to the second region of the first and second plates. All flow between each first flow port and each second flow port should pass through at least one flow restriction (a first or second flow restriction) in the case of the second aspect. In one embodiment, all that is required is for at least some of the flow to pass through only one flow restriction (a first or second flow restriction) in order to completely progress through the MEMS flow module. That is, the MEMS flow module of the second aspect may allow part of the flow through the MEMS flow module to bypass all first and second flow restrictions (e.g., by having one or more etch release holes).

The first region of the first plate (e.g., an "outer" region) and the first region of the second plate (e.g., an "outer" region) may be characterized as a fixed filter section, in that the size of each first flow restriction should not appreciably change in response to any differential pressure, since the first regions of the first and second plates are each at least substantially maintained in a fixed orientation (e.g., such that the first region of both the first and second plates does not flex or otherwise change shape to any significant degree). The second region of the first plate (e.g., an "inner" region) and the second region of the second plate (e.g., an "inner" region) may be characterized as a pressure regulator section, in that at least one of the first and second plates flexes in response to the development of at least a certain differential pressure across the MEMS flow module to change at least one dimension of at least one second flow restriction and/or decrease the flow resistance of at least one second flow restriction in a manner that accommodates an increased flow or flow rate through the MEMS flow module. Each first and second flow restriction may be of any desired size. In one embodiment, all first flow restrictions and all second flow restrictions are the same size. In another embodiment, all first flow restrictions are of one common size, and all second flow restrictions are of another common size.

A plurality of first flow-restricting structures could extend from the first region of the first plate, a plurality of second flow-restricting structures could extend from the second region of the first plate, or both. The first and second flow-restricting structures used by this second aspect may be in accordance with the first and/or second flow-restricting structure(s) that were discussed above in relation to the first aspect. For instance, each first and second flow-restricting structure used in relation to the second aspect could be annular and concentrically disposed. In any case, a plurality of first and second flow ports may be arranged such that a flow through any first flow port will have to flow through a first or second flow restriction before reaching any second flow port, and vice versa (e.g., one or more first flow ports and one or more second flow ports may be disposed in alternating relation between pairs of adjacent annular flow-restricting structures).

In one embodiment, a first annular wall extends between the first region of the first plate (e.g., an "outer" region) and the first region of the second plate (e.g., an "outer" region), and at least contributes to maintaining the first region of the first and second plates in an at least substantially fixed orientation (e.g., such that the first region of both the first and second plates does not flex or otherwise change shape to any significant degree). Each flow-restricting structure may be disposed inwardly of this first annular wall. A plurality of structural interconnects may extend between the first region of the first plate and the first region of the second plate, alone or in combination with the noted first annular wall. Each such structural interconnect may be of any appropriate size, shape, and configuration, and the various structural interconnects may be disposed in any appropriate arrangement within the first region of the first and second plates.

The MEMS flow module of the first and second aspects, including the above-noted first, second, third, and fourth embodiments of the MEMS flow module, may be used other than with the described implant of the first aspect. For instance, any of these MEMS flow modules may be disposed in a flow path of any type (e.g., between a pair of sources of any appropriate type, such as a man-made reservoir, a biological reservoir, and/or the environment). Stated another way, one or more of any of these MEMS flow modules could be disposed in a conduit that fluidly interconnects multiple sources (e.g., two or more), and each source may be either a man-made reservoir, a biological reservoir, the environment, or any other appropriate source. Each of these embodiments of MEMS flow modules may be used in any appropriate application, and may be presented independently of any application-specific requirements.

The MEMS flow modules associated with the first and second aspects are subject to a number of additional characterizations, including without limitation the MEMS flow modules of the first, second, third, and fourth embodiments of the first aspect. One is that a flow path having a volume greater than zero may always be present through the MEMS flow module. For instance, the spacing that defines the flow restriction may have a positive value when there is no differential pressure across the MEMS flow module. In one embodiment, the MEMS flow module may primarily provide a filtering function where there is little or no differential pressure across the MEMS flow module, and may provide at least a pressure regulation function when there is a differential pressure across the MEMS flow module (at least some type of filtering function may still be provided in this second instance as well).

The MEMS flow modules associated with the first and second aspects are also preferably a passive device (no external electrical signal of any type required). Stated another way, the MEMS flow module is autonomous in that it is a self-contained structure and requires no external power. Further in this regard, the "flexing" described in relation to the MEMS flow module is preferably an elastic deformation or the like. As such, upon any reduction of the differential pressure, the spring force that is stored in the "flexed" structure will at least contribute to moving the flexed structure back toward an un-deformed state. How far back toward the un-deformed state the flexed structure will move may depend upon the amount that the differential pressure is reduced.

Surface micromachining is the preferred technology for fabricating the MEMS flow modules described herein. In this regard, the various plates of the MEMS flow modules described herein each may be fabricated from one or more layers or films, where each layer or film has a thickness of no more than about 10 microns in one embodiment, and more typically a thickness within a range of about 1 micron to about 3 microns in another embodiment. Each of the MEMS flow modules described herein may be fabricated in at least two different or separate fabrication levels (hereafter a first fabrication level and a second fabrication level). "Fabrication level" corresponds with what may be formed by a deposition of a structural material before having to form any overlying layer of a sacrificial material (e.g., from a single deposition of a structural layer or film). The first plate discussed herein may be fabricated at least in the first fabrication level, while the second plate discussed herein may be fabricated in at least the second fabrication level. It should be appreciated that the characterization of the first plate being in the "first fabrication level" and the second plate being in the "second fabrication level" by no means requires that the first fabrication level be that which is deposited "first", and that the second fabrication level be that which is deposited "second." Moreover, it does not require that the first fabrication level and the second fabrication level be immediately adjacent to each other. These MEMS flow modules may be fabricated on an appropriate substrate and where the first plate is fabricated in one structural layer that is disposed somewhere between the substrate and another structural layer in which the second plate is fabricated, or vice versa.

The first plate and second plate each may exist in a single fabrication level or may exist in multiple fabrication levels. In the above-noted first instance, a deposition of a structural material in a single fabrication level may define an at least generally planar layer. Another option regarding the first instance would be for the deposition of a structural material in a single fabrication level to define an at least generally planar portion, plus one or more structures that extend down toward, but not to, the underlying structural layer at the underlying fabrication level (e.g., the first flow-restricting structure that extends from the first plate). In either situation and prior to the release, in at least some cases there will be at least some thickness of sacrificial material disposed between the first and second plates.

Various techniques may be employed to increase the rigidity of the first and/or second plate, for instance such that it remains in an at least substantially fixed orientation (e.g., such that it does not flex or otherwise change shape to any significant degree) when the MEMS flow module is exposed to the anticipated differential pressures. Two or more structural layers or films from adjacent fabrication levels could also be disposed in direct interfacing relation (e.g., one directly on the other) to increase the rigidity of the first and/or second plate. Over the region that is to define the first plate or second plate, this would require removal of at least some of the sacrificial material that is deposited on the structural material at one fabrication level before depositing the structural material at the next fabrication level (e.g. sacrificial material may be encased by a structural material, so as to not be removed by the release). Another option for increasing the rigidity of the first and/or second plate would be to maintain the separation between structural layers or films in different fabrication levels for the first plate and/or second plate, but provide an appropriate structural interconnection therebetween (e.g., a plurality of columns, posts, or the like extending between a third plate in a third fabrication level and either the first or second plate).

DETAILED DESCRIPTION OF THE INVENTION

Figure 1:
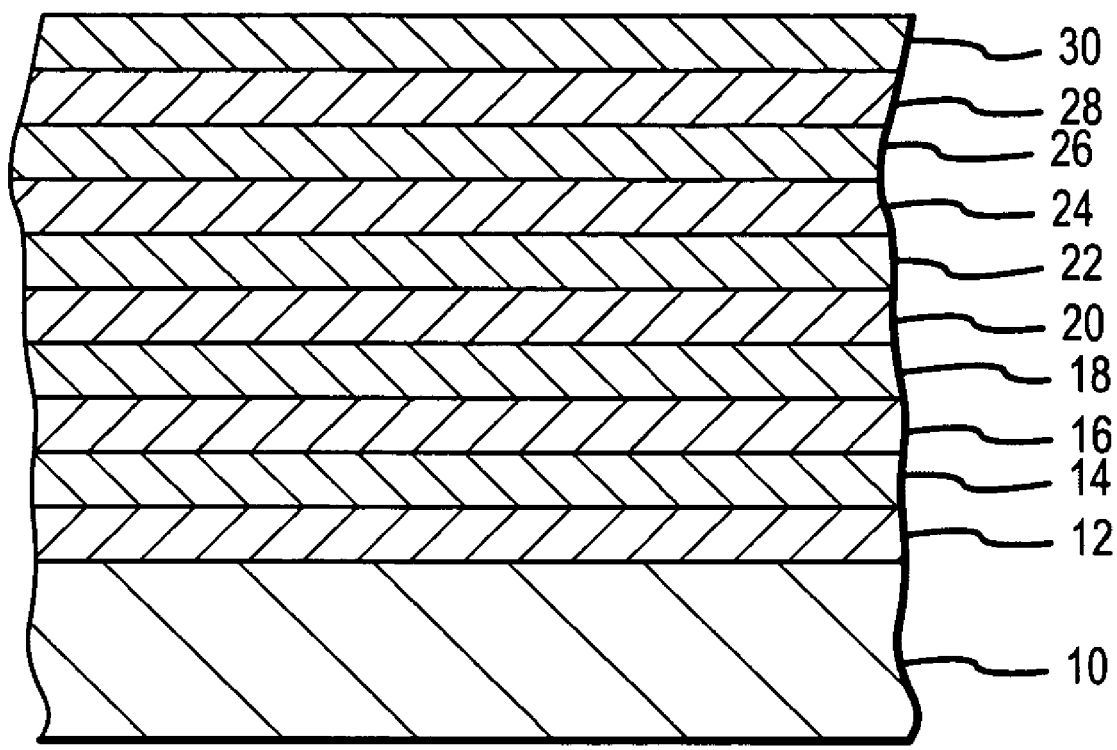
FIG. 1 is a side view of a plurality of layers that may be used by one embodiment of a surface micromachining fabrication technique.

The present invention will now be described in relation to the accompanying drawings that at least assist in illustrating its various pertinent features. Generally, the devices described herein are microfabricated. There are a number of microfabrication technologies that are commonly characterized as "micromachining," including without limitation LIGA (Lithographie, Galvonoformung, Abformung), SLIGA (sacrificial LIGA), bulk micromachining, surface micromachining, micro electrodischarge machining (EDM), laser micromachining, 3-D stereolithography, and other techniques. Hereafter, the term "MEMS device," "microfabricated device," or the like means any such device that is fabricated using a technology that allows realization of a feature size of 10 microns or less. Any appropriate microfabrication technology or combination of microfabrication technologies may be used to fabricate the various devices to be described herein.

Surface micromachining is currently the preferred fabrication technique for the various devices to be described herein. One particularly desirable surface micromachining technique is described in U.S. Pat. No. 6,082,208, that issued Jul. 4, 2000, that is entitled "Method For Fabricating Five-Level Microelectromechanical Structures and Microelectromechanical Transmission Formed," and the entire disclosure of which is incorporated by reference in its entirety herein. Surface micromachining generally entails depositing alternate layers of structural material and sacrificial material using an appropriate substrate (e.g., a silicon wafer) which functions as the foundation for the resulting microstructure. Various patterning operations (collectively including masking, etching, and mask removal operations) may be executed on one or more of these layers before the next layer is deposited so as to define the desired microstructure. After the microstructure has been defined in this general manner, all or a portion of the various sacrificial layers are removed by exposing the microstructure and the various sacrificial layers to one or more etchants. This is commonly called "releasing" the microstructure.

The term "sacrificial layer" as used herein means any layer or portion thereof of any surface micromachined microstructure that is used to fabricate the microstructure, but which does not generally exist in the final configuration (e.g., sacrificial material may be encased by a structural material at one or more locations for one or more purposes, and as a result this encased sacrificial material is not removed by the release). Exemplary materials for the sacrificial layers described herein include undoped silicon dioxide or silicon oxide, and doped silicon dioxide or silicon oxide ("doped" indicating that additional elemental materials are added to the film during or after deposition). The term "structural layer" as used herein means any other layer or portion thereof of a surface micromachined microstructure other than a sacrificial layer and a substrate on which the microstructure is being fabricated. Exemplary materials for the structural layers described herein include doped or undoped polysilicon and doped or undoped silicon. Exemplary materials for the substrates described herein include silicon. The various layers described herein may be formed/deposited by techniques such as chemical vapor deposition (CVD) and including low-pressure CVD (LPCVD), atmospheric-pressure CVD (APCVD), and plasma-enhanced CVD (PECVD), thermal oxidation processes, and physical vapor deposition (PVD) and including evaporative PVD and sputtering PVD, as examples.

In more general terms, surface micromachining can be done with any suitable system of a substrate, sacrificial film(s) or layer(s) and structural film(s) or layer(s). Many substrate materials may be used in surface micromachining operations, although the tendency is to use silicon wafers because of their ubiquitous presence and availability. The substrate is essentially a foundation on which the microstructures are fabricated. This foundation material must be stable to the processes that are being used to define the microstructure(s) and cannot adversely affect the processing of the sacrificial/structural films that are being used to define the microstructure(s). With regard to the sacrificial and structural films, the primary differentiating factor is a selectivity difference between the sacrificial and structural films to the desired/required release etchant(s). This selectivity ratio may be on the order of about 10:1, and is more preferably several hundred to one or much greater, with an infinite selectivity ratio being most preferred. Examples of such a sacrificial film/structural film system include: various silicon oxides/various forms of silicon; poly germanium/poly germanium-silicon; various polymeric films/various metal films (e.g., photoresist/aluminum); various metals/various metals (e.g., aluminum/nickel); polysilicon/silicon carbide; silicone dioxide/polysilicon (i.e., using a different release etchant like potassium hydroxide, for example). Examples of release etchants for silicon dioxide and silicon oxide sacrificial materials are typically hydrofluoric (HF) acid based (e.g., concentrated HF acid, which is actually 49 wt % HF acid and 51 wt % water; concentrated HF acid further diluted with water; buffered HF acid (HF acid and ammonium fluoride)).

The microfabrication technology described in the above-noted '208 patent uses a plurality of alternating structural layers (e.g., polysilicon and therefore referred to as "P" layers herein) and sacrificial layers (e.g., silicon dioxide, and therefore referred to as "S" layers herein). The nomenclature that is commonly used to describe the various layers in the microfabrication technology described in the above-noted '208 patent will also be used herein.

FIG. 1 generally illustrates one embodiment of layers on a substrate 10 that is appropriate for surface micromachining and in accordance with the nomenclature commonly associated with the '208 patent. Each of these layers will typically have a thickness of no more than about 10 microns, and more typically a thickness within a range of about 1 micron to about 3 microns. Progressing away from the substrate 10, the various layers are: a dielectric layer 12 (there may be an intermediate oxide layer between the dielectric layer 12 and the substrate 10 as well, which is not shown); a $P_0$ layer 14 (a first fabrication level); an $S_1$ layer 16; a $P_1$ layer 18 (a second fabrication level); an $S_2$ layer 20; a $P_2$ layer 22 (a third fabrication level); an $S_3$ layer 24; a $P_3$ layer 26 (a fourth fabrication level); an $S_4$ layer 28; and a $P_4$ layer 30 (a fifth fabrication level). In some cases, the $S_2$ layer 20 may be removed such that the $P_2$ layer 22 is deposited directly on the $P_1$ layer 18, and such will hereafter be referred to as a $P_1/P_2$ layer. It should also be appreciated that one or more other layers may be deposited on the $P_4$ layer 30 after the formation thereof and prior to the release, where the entirety of the $S_1$ layer 16, $S_2$ layer 20, $S_3$ layer 24, and $S_4$ layer 28 may be removed (although portions of one or more of these layers may be retained for one or more purposes if properly encased so as to be protected from the release etchant). It should also be appreciated that adjacent structural layers may be structurally interconnected by forming cuts or apertures through the entire thickness of a particular sacrificial layer before depositing the next structural layer. In this case, the structural material will not only be deposited on the upper surface of the particular sacrificial layer, but will be deposited in these cuts or apertures as well (and will thereby interconnect a pair of adjacent, spaced, structural layers).

Figure 2A:
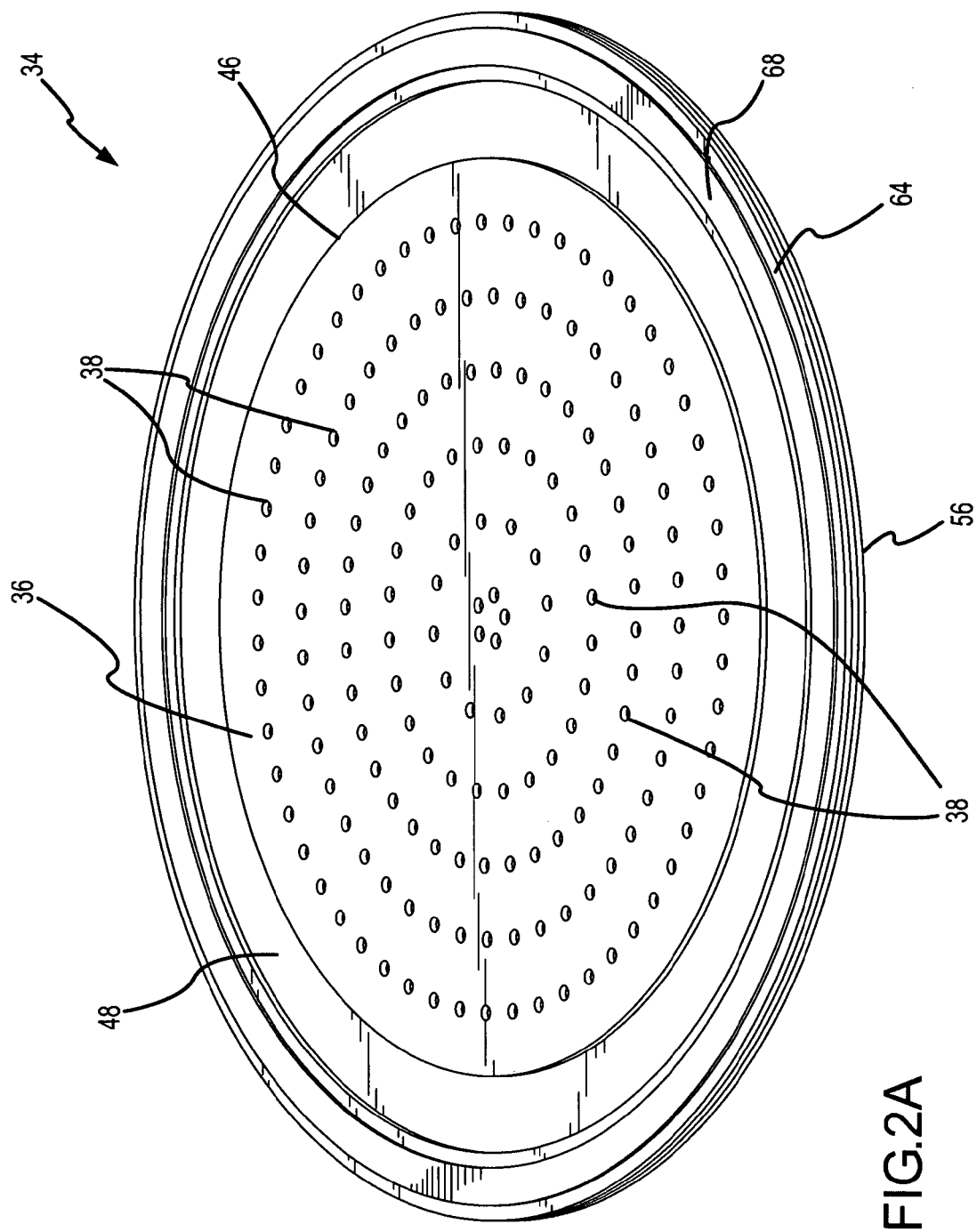
FIG. 2A is a perspective view of one embodiment of an MEMS flow module that uses a flexing diaphragm for regulating pressure.
Figure 2B:
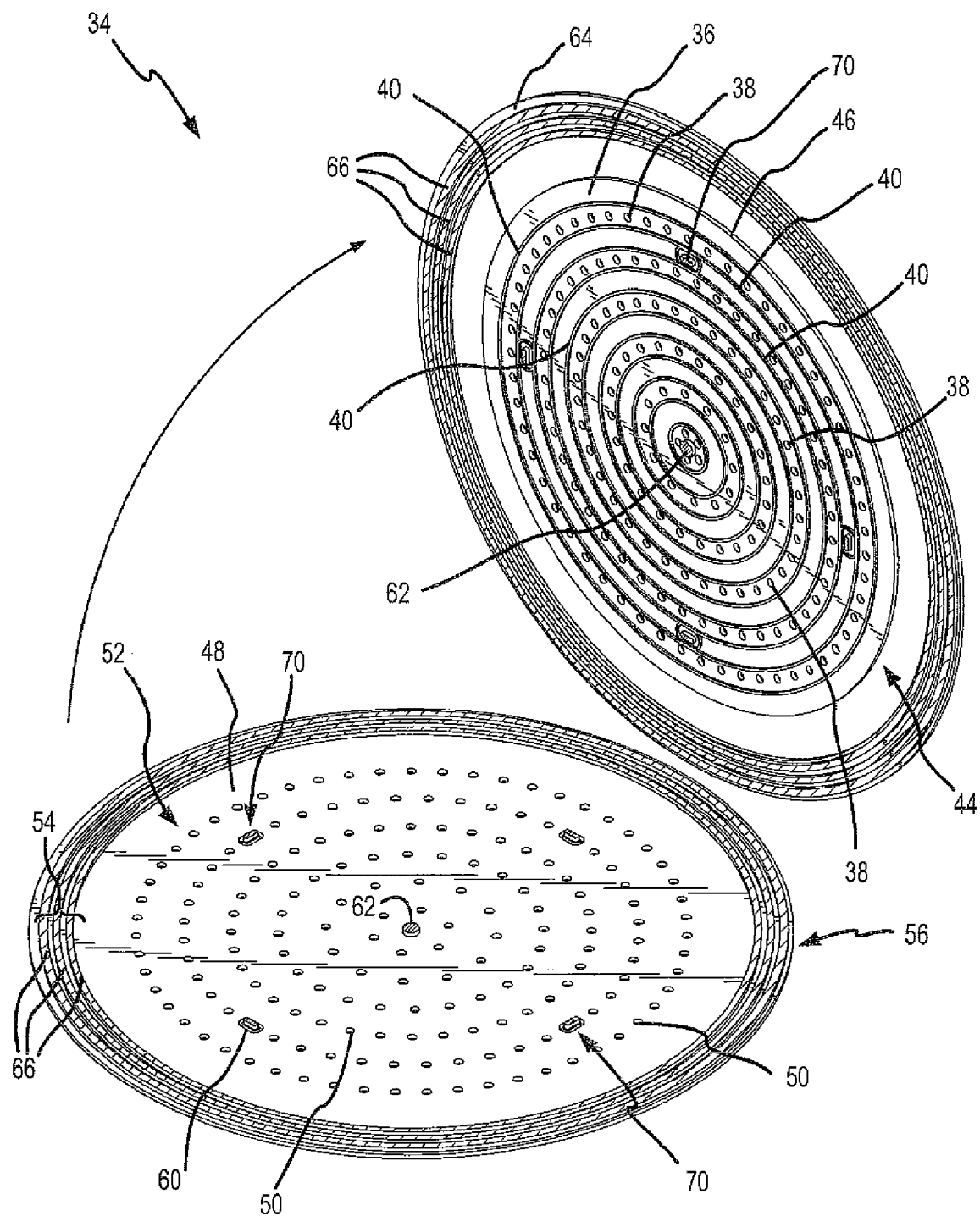
FIG. 2B is a cross-sectional, exploded, perspective view of first and second plates and a plurality of interconnecting annular supports for the MEMS flow module of FIG. 2A.
Figure 2C:
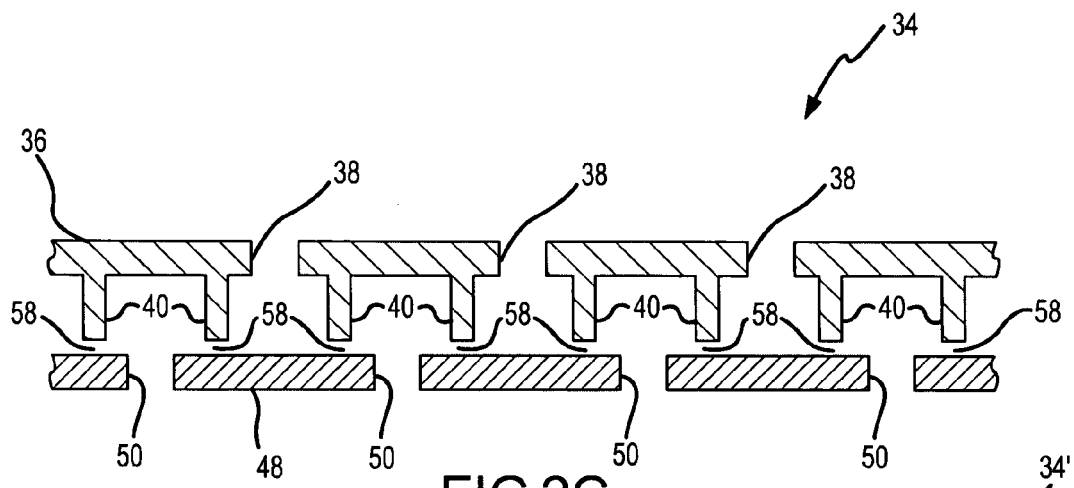
FIG. 2C is a cross-sectional view of the first and second plates of the MEMS flow module of FIG. 2A that shows a flow-restricting gap between the second plate and the flow-restricting walls of the first plate.

The general construction of one embodiment of a MEMS flow module (a MEMS device) is illustrated in FIGS. 2A-C, is identified by reference numeral 34, and provides at least a pressure regulation function by a flexing diaphragm. Although the MEMS flow module 34 is illustrated as having a circular configuration in plan view, any appropriate configuration may be utilized and in any appropriate size. Generally, FIG. 2B shows a cross-sectional, exploded, perspective view of the MEMS flow module 34. More specifically, FIG. 2B is a cross-section of the MEMS flow module 34 that is taken along a plane that is parallel to its first plate 36, at a location that is between the first plate 36 and its second plate 48 so as to extend through flow-restricting gaps 58 between the distal ends of flow-restricting walls 40 and the second plate 48, and with the first plate 36 being pivoted away from the second plate 48. FIG. 2C illustrates the position of the first plate 36 and the second plate 48 at a time when there is no differential pressure across the MEMS flow module 34 (hereafter a "home position").

Continuing to refer to FIGS. 2A-C, the MEMS flow module 34 includes a first plate 36 (e.g., fabricated in $P_4$ layer 30) having a plurality of first flow ports 38 that extend completely through the first plate 36, a second plate 48 (e.g., fabricated in $P_3$ layer 26) having a plurality of second flow ports 50 that extend completely through the second plate 48, a first connector or link 62 (e.g., fabricated in $P_4$ layer 30) that extends between and structurally interconnects the first plate 36 and the second plate 48 (and further disposes the first plate 36 and the second plate 48 in spaced relation), and a plurality of flow-restricting walls 40 (e.g., fabricated in $P_4$ layer 30). The flow-restricting walls 40 extend from the first plate 36 in the direction of the second plate 48. A gap or space 58 (a flow restriction) exists between the distal end of each flow-restricting wall 40 and the second plate 48 to provide a desired flow restriction in the illustrated embodiment, although this gap 58 between each of the flow-restricting walls 40 and the second plate 48 may be defined in any appropriate manner. As will be discussed in more detail below, a certain flexing of the first plate 36 and/or the second plate 48 will change at least one dimension of at least one flow-restricting gap 58 and/or decrease the flow resistance through at least one flow-restricting gap 58 to accommodate an increased flow or flow rate through the MEMS flow module 34.

At least some of the flow entering the MEMS flow module 34 must pass through at least one flow-restricting gap 58 in order to progress completely through the MEMS flow module 34. That is, the first flow ports 38 and the second flow ports 50 are arranged so that at least some of the flow entering the MEMS flow module 34 through a second flow port 50 will have to pass through at least one flow-restricting gap 58 before exiting the MEMS flow module 34 through a first flow port 38. In the illustrated embodiment, all that is required is for at least some of the flow to pass through only one gap 58 in order to progress completely through the MEMS flow module 34. Any way of providing one or more fluid seals to direct at least some of the flow through at least one gap 58 of the MEMS flow module 34 may be utilized.

The foregoing reference to "at least some of the flow" relates to the situation where part of the flow through the MEMS flow module 34 is in fact allowed to bypass all of its flow-restricting gaps 58. For instance, it may be acceptable for at least certain applications to have the MEMS flow module 34 include one or more etch release holes (not shown) that would allow a portion of the flow through the MEMS flow module 34 to bypass all of its flow-restricting gaps 58. It is possible that the ability of the MEMS flow module 34 to provide a pressure regulation function will not be adversely affected to an undesired degree by allowing a limited bypass flow of this type. However, the use of such etch release holes may have an adverse affect on the filtering capabilities of the MEMS flow module 34, depending upon the size of these etch release holes.

In the illustrated embodiment, the first flow ports 38 and the second flow ports 50 are disposed in alternating relation between adjacent pairs of annular flow-restricting walls 40. For instance, one or more first flow ports 38 may be aligned with a first space between first and second flow-restricting walls 40, while no second flow ports 50 are aligned with this first space. One or more second flow ports 50 may be aligned with a second space between second and third flow-restricting walls 40, while no first flow port 38 is aligned with this second space. Therefore a fluid in the first space would have to flow through the flow-restricting gap 58 associated with the second flow-restricting wall 40 before being able to enter the second space, and vice versa.

The size of each flow-restricting gap 58 may be of any appropriate value when there is no differential pressure across the MEMS flow module 34 (e.g., the home position of FIG. 2C). The size of each flow-restricting gap 58 when there is no differential pressure across the MEMS flow module 34 is no more than about 0.4 microns in one embodiment, is about 0.2 to about 0.3 microns in another embodiment, and is about 0.1 micron or less in yet another embodiment. Each flow-restricting gap 58 may provide a filtering function when there is no differential pressure across the MEMS flow module 34, in addition to providing a desired flow resistance. The size of one or more flow-restricting gaps 58 may be changed to provide at least a pressure-regulation function (e.g., at least some degree of filtering may still be provided at this time as well).

Each flow-restricting gap 58 may be designed such that its corresponding flow-restricting wall 40 and the second plate 48 are spaced to allow at least a certain flow through the MEMS flow module 34 without requiring relative movement between at least part of the first plate 36 and at least part of the second plate 48 to increase the relevant spacing therebetween. That is, the MEMS flow module 34 may be designed to provide a constantly open flow path that allows at least a certain limited flow through the MEMS flow module 34 at all times. Such a constantly open flow path may be beneficial in at least a number of respects. One relates to the case where the MEMS flow module 34 is used to relieve intraocular pressure in an eye (e.g., by being incorporated into an eye implant). In this case, the second plate 48 of the MEMS flow module 34 could be on the "anterior chamber" side (e.g., the flow of aqueous humor out of the anterior chamber of the patient's eye through the MEMS flow module 34 would be through one or more of the second flow ports 50, and then into the spacing between the second plate 48 and the first plate 36, and then through one or more of the first flow ports 38 and/or through a space that exists between a perimeter 46 of the first plate 36 and an annular support 64). Having a flow path through the MEMS flow module 34 exist at all times (such that it always has a volume greater than zero, but with the flow restriction discussed herein) is believed to at least generally mimic the flow of aqueous humor out of the anterior chamber of a patient's eye through the eye's canal of Schlemm. However, the MEMS flow module 34 could be designed so that the flow-restricting walls 40 are effectively disposed directly on the second plate 48 until at least a certain differential pressure develops (e.g., a differential pressure "set-point"), after which at least part of the first plate 36 and/or at least part of the second plate 48 would flex to open the flow path through the MEMS flow module 34. Stated another way, the MEMS flow module 34 could be designed such that the flow-restricting walls 40 are positioned to at least substantially preclude any flow through the MEMS flow module 34 until at least a certain differential pressure exists across the MEMS flow module 34.

At least part of at least one of the first plate 36 or the second plate 48 of the MEMS flow module 34 will flex in response to the existence or development of at least a certain differential pressure across the MEMS flow module 34 to change at least one dimension of one or more of its flow-restricting gaps 58 and/or decrease the flow resistance of one or more flow-restricting gaps 58 to accommodate an increased flow or flow rate through the MEMS flow module 34. Although the amount of differential pressure required to flex one or both of these structures may be of any appropriate magnitude, preferably the relevant structure will flex to at least some degree anytime the differential pressure across the MEMS flow module 34 is greater than zero or anytime there is any change in the differential pressure. As such, flexing will preferably occur anytime the differential pressure across the MEMS flow module 34 is greater than zero or anytime there is any change in the differential pressure. In any case, the MEMS flow module 34 provides a pressure regulation function by the noted flexing. It would be typical to configure the MEMS flow module 34 (as well as the other MEMS flow modules to be described herein) to allow a target flow rate at a target differential pressure. The flow rate through the MEMS flow module 34 at other differential pressures would depend on the various characteristics of the MEMS flow module 34.

The first plate 36 will typically be disposed on the "outlet side" or "low-pressure side" of the MEMS flow module 34. Any appropriate size, shape, and/or configuration may be utilized for the first plate 36. As noted, the first flow ports 38 extend completely through the first plate 36. These first flow ports 38 also may be of any appropriate size, shape, and/or configuration, and further may be disposed in any appropriate arrangement. Any appropriate number of first flow ports 38 may be utilized as well.

Generally, the first flow ports 38 are appropriately distributed within what may be characterized as a second region 44 of the first plate 36. The second region 44 of the first plate 36 extends from a first region 42 of the first plate 36 to a perimeter 46 of the first plate 36 (also see FIGS. 3A-D). The first region 42 of the first plate 36 coincides with where the first link 62 interfaces with the first plate 36. The first link 62 may be of any appropriate size, shape, and/or configuration (e.g., a column or post). Multiple first links 62 could be utilized as well (not shown). In the illustrated embodiment, the first link 62 interfaces with the geometric center of the first plate 36, as well as the geometric center of the second plate 48. It may be possible to dispose the first link 62 in other relative positions on one or both of the first plate 36 and the second plate 48.

Figure 2D:
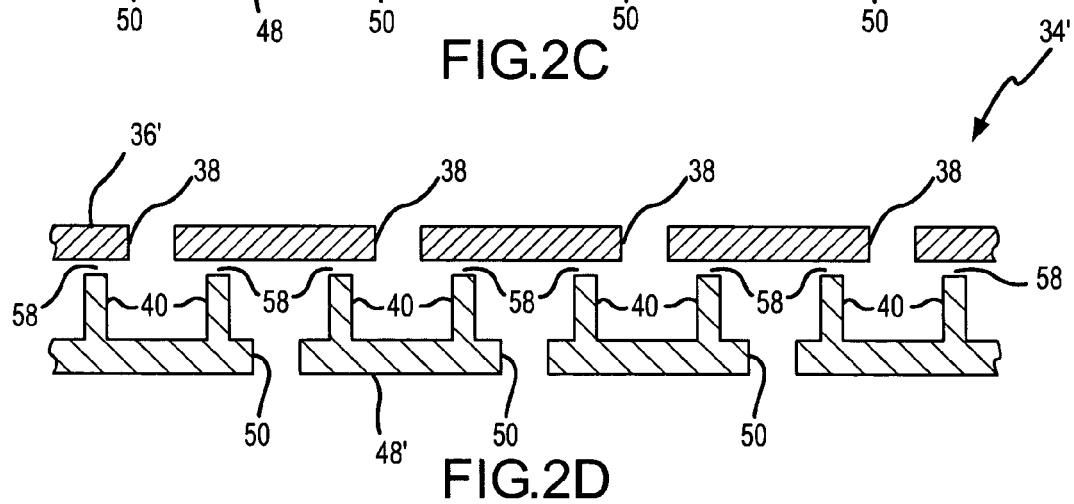
FIG. 2D is a variation of the MEMS flow module of FIG. 2A, where the flow-restricting walls extend from the second plate versus the first plate.

The plurality of flow-restricting walls 40 cooperate with the second plate 48 to provide the desired degree of flow resistance when the MEMS flow module 34 is in the home position of FIG. 2C. However, the MEMS flow module 34 could be fabricated such that the flow-restricting walls 40 instead extend from the second plate 48 in the direction of the first plate 36. This particular variation is illustrated in FIG. 2D, where common components are identified by the same reference numeral, and where a "single prime" designation is used to identify corresponding components that differ in at least some respect. Generally in the case of the MEMS flow module 34' of FIG. 2D, the flow-restricting walls 40 extend from the second plate 48' toward the first plate 36', such that the flow-restricting walls 40 and the first plate 36' cooperate to define the various flow-restricting gaps 58.

Each flow-restricting wall 40 may be of any appropriate size, shape, and configuration. In the illustrated embodiment, the flow-restricting walls 40 are annular. "Annular" again means that the flow-restricting walls 40 extend a full 360 degrees about a common point, and does not limit the flow-restricting walls 40 to having a circular configuration. The various flow-restricting walls 40 are also concentrically disposed relative to each other in the illustrated embodiment. However, it may be possible to arrange each of the various flow-restricting walls 40 about a common point without the flow-restricting walls 40 actually being concentric.

Each adjacent pair of flow-restricting walls 40 may be separated by the same, common spacing, although any appropriate spacing may be utilized between any particular adjacent pair of flow-restricting walls 40 (e.g., a first flow-restricting wall 40 and an adjacent second flow-restricting wall 40 could be separated by a first spacing, while the second flow-restricting wall 40 and an adjacent third flow-restricting wall 40 could be separated by a second spacing that is of a different magnitude than the first spacing). The same spacing may be maintained between all corresponding portions of each adjacent pair of flow-restricting walls 40, although such need not be the case. For instance, a first flow-restricting wall 40 and an adjacent second flow-restricting wall 40 may be separated by a first distance at a first location, and may be separated by a different, second distance at a second location. Stated another way, the gap between each adjacent pair of flow-restricting walls 40 may be constant or otherwise.

Other types of flow-restricting structures could be utilized by the MEMS flow module 34 as well. For instance, one or more of the flow-restricting walls 40 could be replaced by a plurality of flow-restricting segments of any appropriate size, shape, and configuration, where adjacent pairs of flow-restricting segments would be appropriately spaced from each other (e.g., a gap could be introduced in a particular flow-restricting wall 40 at each of a plurality of locations to define these flow-restricting segments). The gap between such flow-restricting segments and the second plate 48, as well as the gap between each adjacent pair of flow-restricting segments, would provide the desired degree of flow restriction with the MEMS flow module 34 being in the home position of FIG. 2C. Other options are discussed below in relation to FIGS. 5A-B and 6.

The second plate 48 will typically be disposed on the "inlet side" or "high-pressure side" of the MEMS flow module 34. Any appropriate size, shape, and/or configuration may be utilized for the second plate 48. As noted, the second flow ports 50 extend completely through the second plate 48. These second flow ports 50 also may be of any appropriate size, shape, and/or configuration, and further may be disposed in any appropriate arrangement. Any appropriate number of second flow ports 50 may be utilized as well.

Generally, the second flow ports 50 are appropriately distributed within what may be characterized as a third region 52 of the second plate 48. A fourth region 54 of the second plate 48 extends from the third region 52 of the second plate 48 to a perimeter 56 of the second plate 48. The fourth region 54 of the second plate 48 generally coincides with where the second plate 48 may be structurally interconnected with an annular support 64 (e.g., fabricated in $P_4$ layer 30) of the MEMS flow module 34, but in any case is a portion of the second plate 48 that is at least substantially maintained in a fixed orientation throughout operation of the MEMS flow module 34 for the anticipated conditions (e.g., such that the fourth region 54 of the second plate 48 does not flex or otherwise change shape to any significant degree). In the illustrated embodiment, the fourth region 54 is a perimeter portion of the second plate 48.

The annular support 64 may be utilized to enhance the rigidity of at least a perimeter portion of the MEMS flow module 34. At least one annular wall, connector, or link 66 (three shown; e.g., fabricated in $P_4$ layer 30) may extend between and structurally interconnect the second plate 48 and the annular support 64. Alternatively, the annular support 64 could be fabricated directly on a perimeter portion of the second plate 48. One or more columns, posts, or the like could also be used to structurally interconnect the annular support 64 with the second plate 48, alone or in combination with one or more annular links 66 (not shown). Any appropriate way of increasing the rigidity of at least a perimeter portion of the MEMS flow module 34 could be implemented.

The MEMS flow module 34 may further include at least one ring 68. A ring 68 could be fixedly interconnected to the annular support 64 such that the annular support 64 is "sandwiched" between the ring 68 and the second plate 48, an annular ring 68 could be fixedly interconnected with the side of the second plate 48 that faces away from the first plate 36, or a first ring 68 could be fixedly interconnected to the annular support 64 and a second ring 68 could be fixedly interconnected with the side of the second plate 48 that faces away from the first plate 36. Any such ring 68 may be a metallic ring that is attached to or formed on the relevant structure after the MEMS flow module 34 has been fabricated, or may be made from another fabrication level. Generally, any such ring 68 may provide a desired interface with a housing or other structure that incorporates the MEMS flow module 34.

Figure 2E:
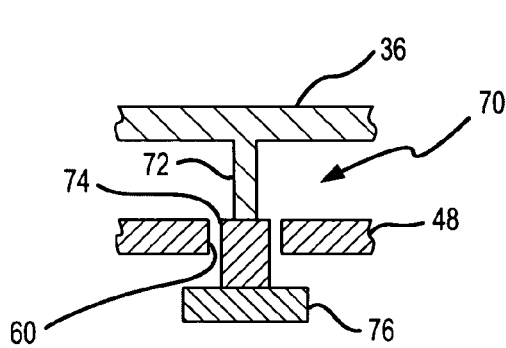
FIG. 2E is a cross-sectional view of one embodiment of a travel limiter that may be used to control the maximum spacing between the first and second plates of the MEMS flow module of FIG. 2A.
Figure 2F:
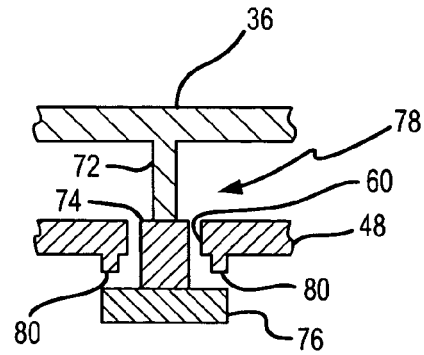
FIG. 2F is a cross-sectional view of another embodiment of a travel limiter that may be used to control the maximum spacing between the first and second plates of the MEMS flow module of FIG. 2A.

It may be desirable to limit the maximum spacing between the first plate 36 and the second plate 48 when either or both are flexing in response to experiencing a differential pressure and in order to accommodate a larger flow or flow rate through the MEMS flow module 34 to provide the desired pressure regulation function. This may be implemented in any appropriate manner. Two possible configurations are presented in FIGS. 2E-F. FIG. 2E illustrates one embodiment of a travel limiter 70. The travel limiter 70 includes a first section 72 (e.g., fabricated in $P_4$ layer 30) that extends from the first plate 36 in the direction of a corresponding travel limiter aperture 60 that extends through the second plate 48. A second section 74 (e.g., fabricated in $P_3$ layer 26) of the travel limiter 70 is disposed within the travel limiter aperture 60, preferably such that an annular gap exists between the perimeter of the second section 74 and the sidewall of the second plate 48 that defines the travel limiter aperture 60. This second section 74 of the travel limiter 70 also extends beyond the second plate 48 and attaches to a head 76 (e.g., fabricated at least in $P_2$ layer 22) that is spaced from the second plate 48 when there is no differential pressure across the MEMS flow module 34. The head 76 is larger than the travel limiter aperture 60. As such, the amount that the first plate 36 and second plate 48 may be moved relatively away from each other is limited to the magnitude of the spacing between the head 76 and the second plate 48. Typically a plurality of travel limiters 70 will be utilized by the MEMS flow module 34, and these travel limiters 70 may be positioned as desired/required to provide a desired maximum spacing between the first plate 36 and the second plate 48.

Fabricating the head 76 of the travel limiter 70 in the $P_2$ layer 22 and fabricating the second plate 48 in the $P_3$ layer 26 may allow the first plate 36 to relatively move further away from the second plate 48 by a distance of about 2 microns from the home position of FIG. 2C and FIG. 2E, and at the location of the travel limiter 70. Depending upon the location of the travel limiter 70 relative to the perimeter 46 of the first plate 36 and/or the perimeter 56 of the second plate 48, a larger travel range may exist between corresponding portions of the first plate 36 and the second plate 48 (e.g., portions disposed closer to their corresponding perimeter 46, 56). One way to provide less than a 2 micron travel limit from the home position of FIG. 2C is provided by the travel limiter 78 of FIG. 2F. Common components of the travel limiters 70, 78 are identified by the same reference numeral. Generally, the travel limiter 78 includes an additional structure in the form of one or more stops 80 (e.g., fabricated in $P_3$ layer 26) that extend from the second plate 48 toward, but not to, the head 76 when there is no differential pressure across the MEMS flow module 34. Each stop 80 may be of any appropriate size, shape, and configuration. The maximum spacing between the first plate 36 and the second plate 48, at the location of the travel limiter 78, will be when the stops 80 engage the head 76.

One or both of the first plate 36 and the second plate 48 will flex upon experiencing at least a certain differential pressure to accommodate an increased flow or flow rate through the MEMS flow module 34. Preferably, this is by an elastic deformation. The elasticity may then at least contribute to returning the relevant structure back toward its original position upon a subsequent reduction of the differential pressure. This preferably applies to the various other MEMS flow modules described herein.

Figure 3A:
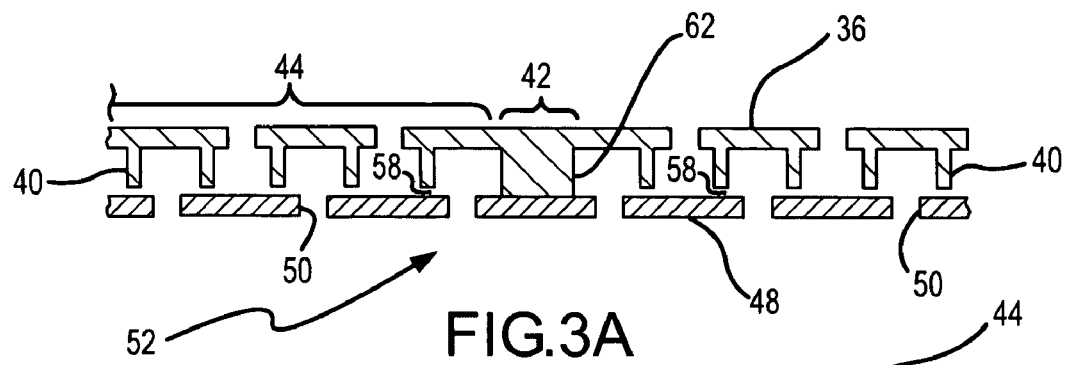
FIG. 3A is a cross-sectional view of part of the first and second plates of the MEMS flow module of FIG. 2A, where there is no differential pressure.
Figure 3B:
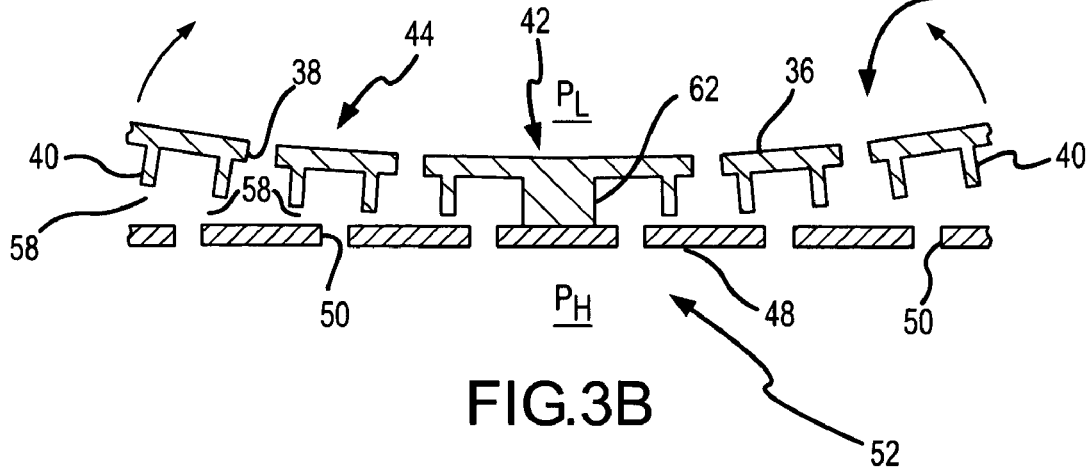
FIG. 3B is a cross-sectional view of the first and second plates of the MEMS flow module of FIG. 2A, where the first plate is configured to flex in response to experiencing a differential pressure.
Figure 3C:
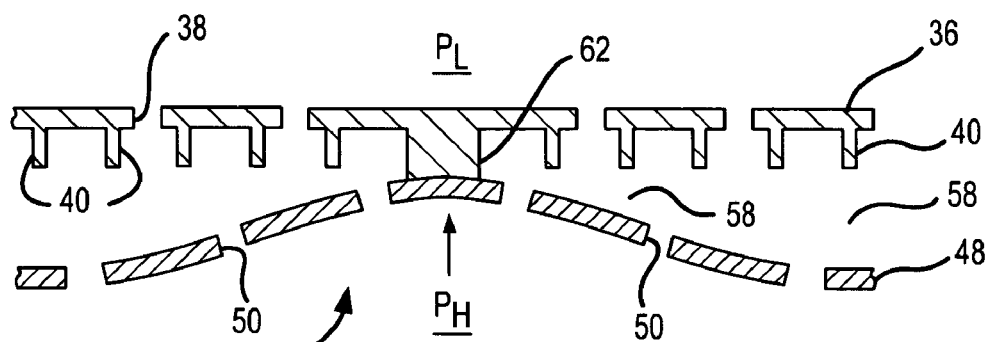
FIG. 3C is a cross-sectional view of the first and second plates of the MEMS flow module of FIG. 2A, where the second plate is configured to flex in response to experiencing a differential pressure.
Figure 3D:
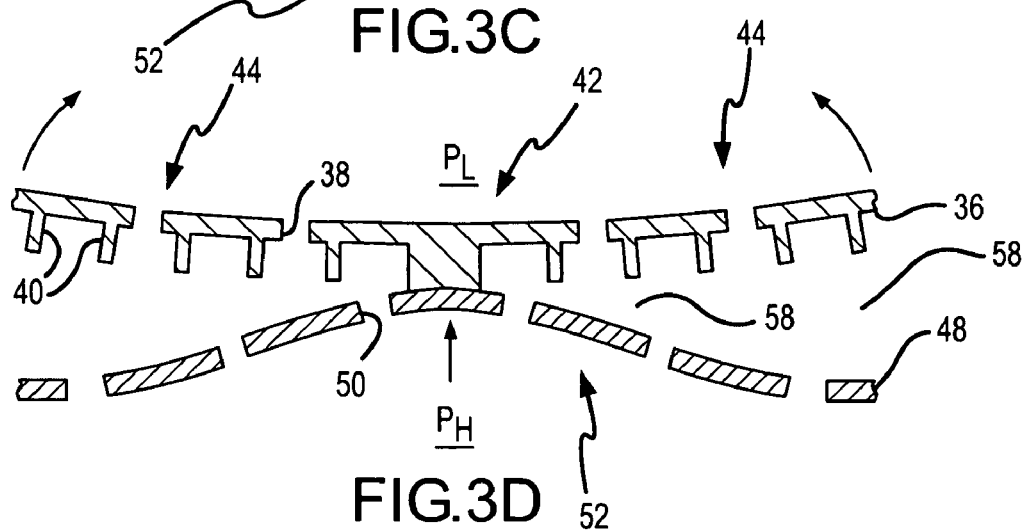
FIG. 3D is a cross-sectional view of the first and second plates of the MEMS flow module of FIG. 2A, where both the first and second plates are configured to flex in response to experiencing a differential pressure.

FIG. 3A illustrates a preferred position of the first plate 36 and the second plate 48 when there is no differential pressure across the MEMS flow module 34. FIGS. 3B-D present three different options for configuring the MEMS flow module 34 to address the existence of at least a certain differential pressure. FIG. 3B illustrates that the first plate 36 may be configured to flex, and that the entire second plate 48 may be configured to be at least substantially maintained in a fixed orientation (e.g., such that the entire second plate 48 does not flex or otherwise change shape to any significant degree). More specifically, the second region 44 of the first plate 36 flexes at least generally away from the second plate 48 and at least generally about the first region 42 of the first plate 36 (where the first link 62 is anchored to the first plate 36) when the pressure $P_H$ exceeds the pressure $P_L$. The first plate 36 may assume an at least generally cup-shaped profile. In the illustrated embodiment, those flow-restricting walls 40 that are disposed closer to the perimeter 46 of the first plate 36 will be spaced further from the second plate 48 than those flow-restricting walls 40 that are disposed closer to the first region 42 of the first plate 36. Stated another way and for the case of the illustrated embodiment, the spacing between the flow-restricting walls 40 and the second plate 48 will increase from flow-restricting wall 40 to flow-restricting wall 40 progressing in the direction of the perimeter 46 of the first plate 36. Increasing the size of the flow-restricting gap 58 associated with a particular flow-restricting wall 40, which decreases the flow resistance through this particular flow-restricting gap 58, will accommodate a larger flow or flow rate through the MEMS flow module 34. Generally, the flexing of the first plate 36 may be characterized as increasing the size of one or more flow-restricting gaps 58 (e.g., changing at least one dimension of one or more flow-restricting gaps 58), decreasing the flow resistance of one or more flow-restricting gaps 58, or both. In any case, this type of flexing accommodates a larger flow or flow rate through the MEMS flow module 34.

It should be appreciated that a variety of factors may impact how the first plate 36 actually flexes when exposed to a differential pressure. Any desired "flexing profile" may be utilized for the first plate 36 (e.g., its "shape" after the first plate 36 flexes when exposed to a differential pressure), and this flexing profile may be realized in any appropriate manner. For instance, the first plate 36 could be configured/reinforced in a manner such that two locations that are equally spaced from the geometric center of the first plate 36 will actually flex a different amount when exposed to the same differential pressure.

FIG. 3C illustrates that the second plate 48 may be configured to flex, and that the entire first plate 36 may be configured to be at least substantially maintained in a fixed orientation (e.g., such that the entire first plate 36 does not flex or otherwise change shape to any significant degree, which is in effect the inverse of the FIG. 3B configuration). More specifically, the third region 52 of the second plate 48 flexes at least generally in the direction of the first plate 36 and relative to the fourth region 54 of the second plate 48 (where the second plate 48 is anchored to the annular support 64) when the pressure $P_H$ exceeds the pressure $P_L$. Typically, the fourth region 54 of the second plate 48 will be at least substantially maintained in a fixed orientation as noted (e.g., such that the fourth region 54 of the second plate 48 does not flex or otherwise change shape to any significant degree). Since the first link 62 engages the second plate 48 within the third region 52 (preferably at the center of the second plate 48) and also engages the first plate 36 within its first region 42, the flexing of the third region 52 of the second plate 48 in the noted manner will raise the first plate 36 relative to the fourth region 54 of the second plate 48, to increase the spacing between the first plate 36 and at least part of the second plate 48. As in the case of the FIG. 3B configuration and for the illustrated embodiment, those flow-restricting walls 40 that are disposed closer to the perimeter 46 of the first plate 36 will be spaced further from the second plate 48 than those flow-restricting walls 40 that are disposed closer to the first region 42 of the first plate 36. Stated another way and for the illustrated embodiment, the spacing between the flow-restricting walls 40 and the second plate 48 will increase from flow-restricting wall 40 to flow-restricting wall 40 progressing in the direction of the perimeter 46 of the first plate 36. Increasing the size of the flow-restricting gap 58 associated with a particular flow-restricting wall 40, which decreases the flow resistance through this particular flow-restricting gap 58, will accommodate a larger flow or flow rate through the MEMS flow module 34. Generally, the flexing of the second plate 48 may be characterized as increasing the size of one or more flow-restricting gaps 58 (e.g., changing at least one dimension of one or more flow-restricting gaps 58), decreasing the flow resistance of one or more flow-restricting gaps 58, or both. In any case, this type of flexing accommodates a larger flow or flow rate through the MEMS flow module 34.

It should be appreciated that a variety of factors may impact how the second plate 48 actually flexes when exposed to a differential pressure. Any desired "flexing profile" may be utilized for the second plate 48 (e.g., its "shape" after the second plate 48 flexes when exposed to a differential pressure), and this flexing profile may be realized in any appropriate manner. For instance, the second plate 48 could be configured/reinforced in a manner such that two locations that are equally spaced from the geometric center of the second plate 48 will actually flex a different amount when exposed to the same differential pressure.

FIG. 3D in effect illustrates the combination of the FIG. 3B and FIG. 3C configurations. Generally, both the first plate 36 and the second plate 48 flex when the pressure $P_H$ exceeds the pressure $P_L$. More specifically, the second region 44 of the first plate 36 flexes at least generally away from the second plate 48 and at least generally about the first region 42 of the first plate 36 (where the first link 62 is anchored to the first plate 36) when the pressure $P_H$ exceeds the pressure $P_L$. The first plate 36 may assume an at least generally cup-shaped profile. In addition, the third region 52 of the second plate 48 flexes at least generally in the direction of the first plate 36 and relative to the fourth region 54 of the second plate 48 (where the second plate 48 is anchored to the annular support 64) when the pressure $P_H$ exceeds the pressure $P_L$. Typically, the fourth region 54 of the second plate 48 will be at least substantially maintained in a fixed orientation (e.g., such that the fourth region 54 of the second plate 48 does not flex or otherwise change shape to any significant degree). Since the first link 62 engages the second plate 48 within the third region 52 (preferably at the center of the second plate 48) and also engages the first plate 36 within its first region 42, the flexing of the third region 52 of the second plate 48 in the noted manner will raise the first plate 36 relative to the fourth region 54 of the second plate 48, to further increase the spacing between the first plate 36 and at least part of the second plate 48. Once again and for the case of the illustrated embodiment, those flow-restricting walls 40 that are disposed closer to the perimeter 46 of the first plate 36 will be spaced further from the second plate 48 than those flow-restricting walls 40 that are disposed closer to the first region 42 of the first plate 36. Stated another way and in the case of the illustrated embodiment, the spacing between flow-restricting walls 40 and the second plate 48 will increase from flow-restricting wall 40 to flow-restricting wall 40 progressing in the direction of the perimeter 46 of the first plate 36. Increasing the size of the flow-restricting gap 58 associated with a particular flow-restricting wall 40, which decreases the flow resistance through this particular flow-restricting gap 58, will accommodate a larger flow or flow rate through the MEMS flow module 34. Generally, the flexing of the first plate 36 and the second plate 48 may be characterized as increasing the size of one or more flow-restricting gaps 58 (e.g., changing at least one dimension of one or more flow-restricting gaps 58), decreasing the flow resistance of one or more flow-restricting gaps 58, or both. In any case, this type of flexing accommodates a larger flow or flow rate through the MEMS flow module 34.

Surface micromachining is a preferred fabrication technique for the MEMS flow module 34, as well as the other MEMS flow modules to be described herein. For instance, the first plate 36 and the flow-restricting walls 40 may exist at least in a first fabrication level, while the second plate 48 may exist in at least a second fabrication level. More generally, one or both of the first plate 36 and the second plate 48 of the MEMS flow module 34 each may exist in a single fabrication level or may exist in multiple fabrication levels. "Fabrication level" corresponds with what may be formed by a deposition of a structural material before having to form any overlying layer of a sacrificial material (e.g., from a single deposition of a structural layer or film). It should be appreciated that the characterization of a structure described herein being in a "first fabrication level" and another structure described herein being in a "second fabrication level" by no means requires that the first fabrication level be that which is deposited "first", and that the second fabrication level be that which is deposited "second." Moreover, it does not require that the first fabrication level and the second fabrication level be immediately adjacent.

A deposition of a structural material in a single fabrication level may define an at least generally planar layer. Another option would be for the deposition of a structural material in a single fabrication level to define an at least generally planar portion, plus one or more structures that extend down toward, but not to, the underlying structural layer at the underlying fabrication level (e.g., the first plate 36 with the flow-restricting walls 40 extending downwardly therefrom could exist in a common fabrication level). Yet another option would be for the deposition of a structural material in a single fabrication level to define an at least generally planar portion, plus one or more structures that extend down to an underlying structural layer at the underlying fabrication level (e.g., the first plate 36 and the first link 62 may exist in a common fabrication level, where the first link 62 again extends from the first plate 36 to the second plate 48, with the second plate 48 existing in a different fabrication level). In each of these cases and prior to the release, in at least some cases there will be at least some thickness of sacrificial material disposed between at least a portion of the structures in adjacent fabrication levels.

Two or more structural layers or films from adjacent fabrication levels also could be disposed in direct interfacing relation (e.g., one directly on the other) to define a desired structure. The first plate 36 and/or the second plate 48 could be defined in this manner to increase the rigidity of the same. In either case, this would require removal of at least some of sacrificial material that is deposited on the structural material at one fabrication level before depositing the structural material at the next fabrication level. All of the sacrificial material need not be removed between the adjacent structure layers in this case. For instance, it may be desirable to encase sacrificial material at one or more locations in the structural material from adjacent fabrication levels.

Based upon the foregoing, one way to fabricate the MEMS flow module 34 with a plurality of travel limiters 70 would be as follows: 1) deposit the $P_2$ layer 22; 2) pattern the $P_2$ layer 22 to define the head 76 of each travel limiter 70; 3) deposit the $S_3$ layer 24 on top of the $P_2$ layer 22, on top of the head 76 of each travel limiter 70, and into the space between the remainder of the $P_2$ layer 22 and the head 76 of each travel limiter 70; 4) pattern the $S_3$ layer 24 to define a plurality of first apertures that extend down to the head 76 of each travel limiter 70, and that will coincide with the desired configuration of the second section 74 of each travel limiter 70; 5) deposit the $P_3$ layer 26 on top of the $S_3$ layer 24 and into noted first apertures to define the second link 74 for each travel limiter 70; 6) pattern the $P_3$ layer 26 to define the second plate 48, the plurality of second flow ports 50, and a travel limiter aperture 60 for each travel limiter 70; 7) deposit the $S_4$ layer 28 on top of the second plate 48, into the second flow ports 50, and into the portion of each travel limiter aperture 60 that is not occupied by a second section 74 of a travel limiter 70; 8) pattern the $S_4$ layer 28 to define a plurality of annular first apertures that extend down to the second plate 48, and that coincide with the desired location and configuration of the flow-restricting walls 40; 9) deposit a thin layer of sacrificial material on top of the $S_4$ layer 28 and into the annular first apertures, the thickness of which will define the height of the flow-restricting gap 58 for the home position of FIG. 2C; 10) pattern the $S_4$ layer 28 to define a plurality of second apertures, where each second aperture will extend to the second section 74 of a particular travel limiter 70 so as to coincide with the desired configuration of the first section 72 of the corresponding travel limiter 70; 11) pattern the $S_4$ layer 28 to define a third aperture that extends down to the second plate 48, and that will coincide with the desired location and configuration of the first link 62 that extends between and structurally interconnects the second plate 48 and the first plate 36; 12) pattern the $S_4$ layer 28 to define a plurality of annular second apertures that extend down to the second plate 48 and that will coincide with the desired location and configuration of the annular links 66 that structurally interconnect the second plate 48 and the annular support 64; 13) deposit the $P_4$ layer 30 on top of the $S_4$ layer 28, into the second apertures to define the first section 72 of each travel limiter 70, into the third aperture to define the first link 62, into the annular first apertures to define the flow-restricting walls 40, and into the annular second apertures to define the annular links 66; 14) pattern the $P_4$ layer 30 to define the first plate 36 and its first flow ports 38, and further to define the annular support 64 that is laterally or radially spaced from the perimeter 46 of the first plate 36; and 15) initiate a release to remove all exposed sacrificial material from the various sacrificial layers.

Notwithstanding the foregoing, it should be appreciated that the various components of the MEMS flow module 34 may be formed within different layers of a MEMS structure compared to what has been described herein. Furthermore, it will be appreciated that the MEMS flow module 34 may be formed in a MEMS structure in a reverse order to that described above as. In this case and as illustrated in FIG. 2D, the flow-restricting walls 40 would extend from the second plate 48', instead of the first plate 36'. The flow-restricting walls 40 and the second plate 48' would then exist in a common fabrication level.

Figure 4A:
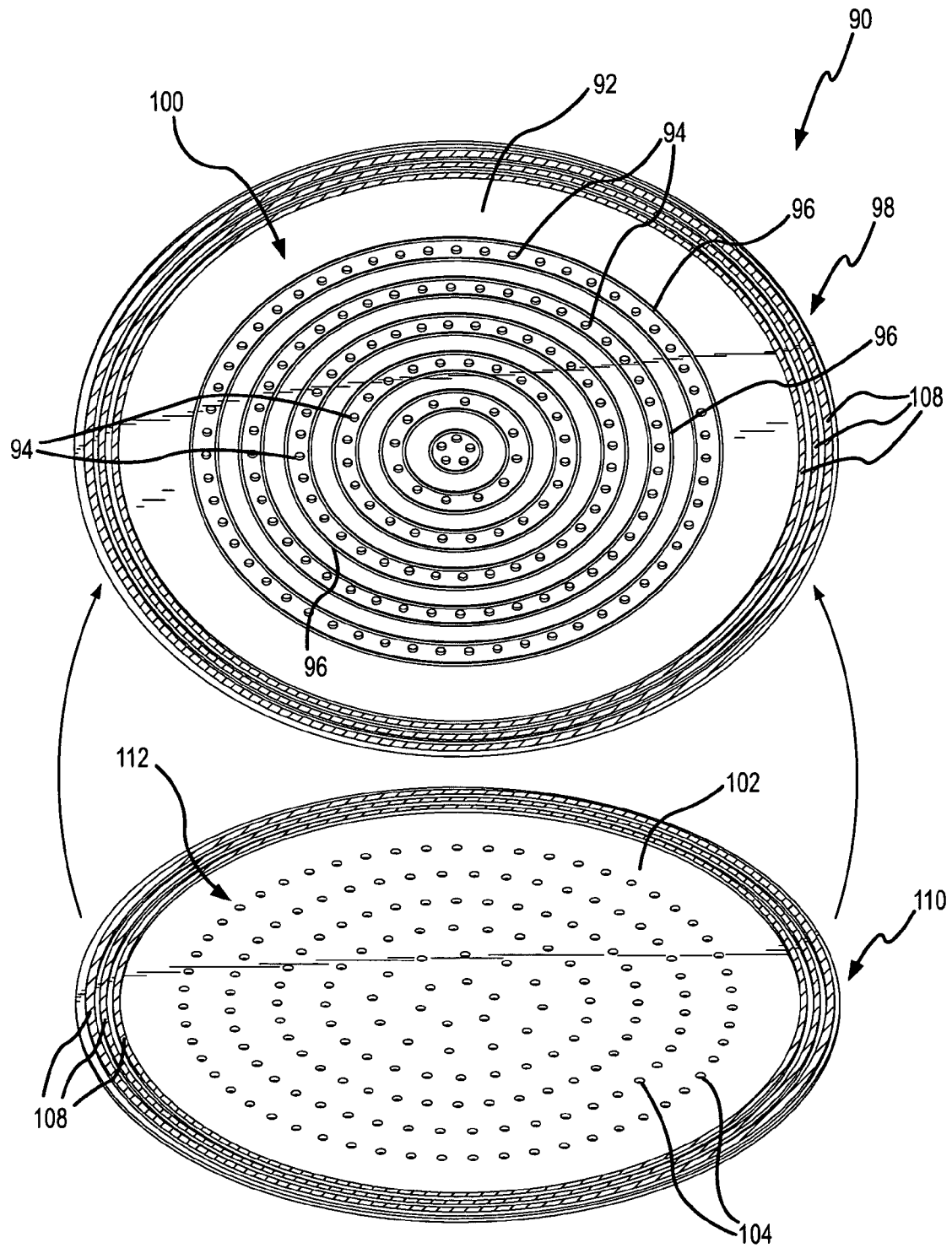
FIG. 4A is a cross-sectional, exploded, perspective view of another embodiment of a MEMS flow module that uses a flexing diaphragm for regulating pressure.
Figure 4B:
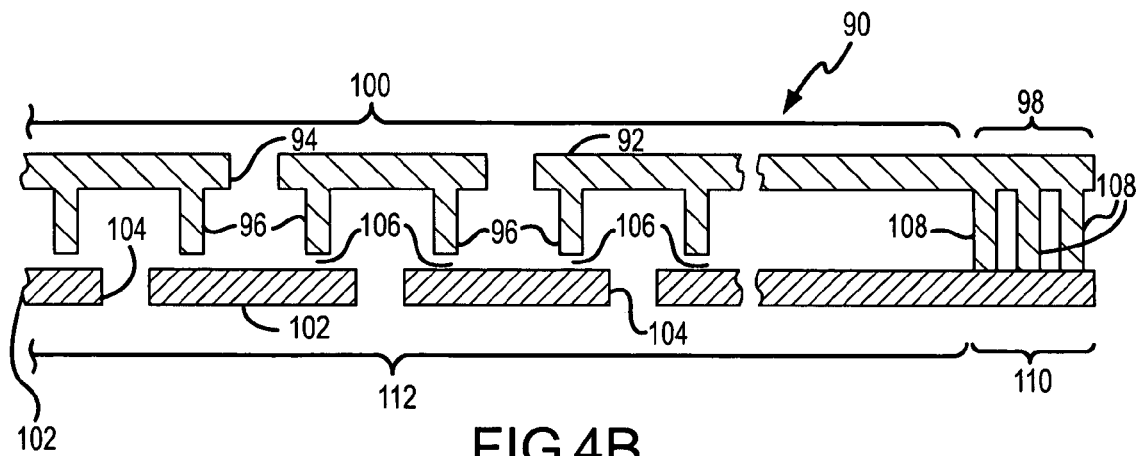
FIG. 4B is a cross-sectional view of the MEMS flow module of FIG. 4A that shows a flow-restricting gap between the second plate and the flow-restricting walls of the first plate.
Figure 4C:
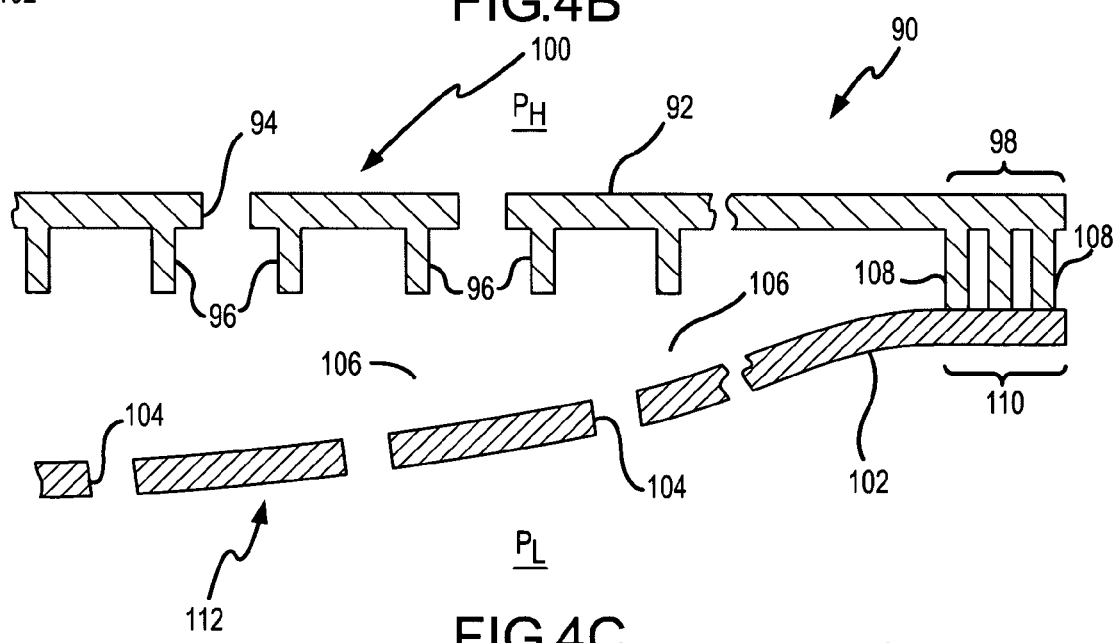
FIG. 4C is a cross-sectional view of the first and second plates of the MEMS flow module of FIG. 4A, where the second plate is configured to flex in response to experiencing a differential pressure.

Another embodiment of a MEMS flow module (a MEMS device) is illustrated in FIGS. 4A-C, is identified by reference numeral 90, and provides at least a pressure regulation function by a flexing diaphragm. Although the MEMS flow module 90 is illustrated as having a circular configuration in plan view, any appropriate configuration may be utilized and in any appropriate size. FIG. 4A shows a cross-section of the MEMS flow module 90 that is taken along a plane that is parallel to its first plate 92, at a location that is between the first plate 92 and its second plate 102 so as to extend through flow-restricting gaps 106 between the distal ends of flow-restricting walls 96 and the second plate 102, and with the first plate 92 having been pivoted away from the second plate 102. Generally, at least one of the first plate 92 and the second plate 102 flexes to increase the spacing between these two structures, to in turn accommodate an increased flow or flow rate through the MEMS flow module 90. Once again, preferably this flexing is by an elastic deformation. The elasticity may then at least contribute to returning the relevant structure back toward its original position upon a subsequent reduction of the differential pressure.

As shown in FIGS. 4A-C, the MEMS flow module 90 includes a first plate 92 (e.g., fabricated in $P_3$ layer 26, possibly reinforced with $P_4$ layer 30) having a plurality of first flow ports 94 that extend completely through the first plate 92, a second plate 102 (e.g., fabricated in $P_2$ layer 22, possibly reinforced by depositing $P_2$ layer 22 directly on $P_1$ layer 18) having a plurality of second flow ports 104 that extend completely through the second plate 102, and a plurality of flow-restricting walls 96 (e.g., fabricated in $P_3$ layer 26). A first region 98 of the first plate 92 and a first region 110 of the second plate 102 include one or more structural interconnections that extend between the first plate 92 and the second plate 102. In the illustrated embodiment, this structural interconnection is in the form of at least one annular connector, wall, or link 108 of any appropriate size, shape, and/or configuration. This not only disposes the first plate 92 and the second plate 102 in spaced relation and structurally interconnects the same, but provides at least one radial seal—namely a seal that reduces the potential of fluid exiting the MEMS flow module 90 through the space between the first plate 92 and the second plate 102. Using multiple, radially-spaced annular links 108 would thereby provide multiple, radially-spaced, radial seals. Other types of structural connections could exist in the first region 98 of the first plate 92 and the first region 110 of the second plate 102 if such a "radial seal" function was not desired or required, if one or more seals existed elsewhere to at least attempt to force all flow through the MEMS flow module 90, or both. For instance, a plurality of columns, posts, or the like could structurally interconnect the first region 98 of the first plate 92 and the first region 110 of the second plate 102. In any case, the first region 98 of the first plate 92 and the first region 110 of the second plate 102 generally are at least substantially maintained in a fixed orientation during use of the MEMS flow module 90 under the anticipated conditions (e.g., such that the first region 98 of the first plate 92 and the first region 110 of the second plate 102 do not flex or otherwise change shape to any significant degree).

The MEMS flow module 90 may include various features from the MEMS flow module 34 of FIGS. 2A-C. The noted annular support 64 may be interconnected with the first plate 92 by one or more of the noted annular connectors, walls, or links 66 so as to "sandwich" the first plate 92 between the annular support 64 and the second plate 102. A ring 68 could be disposed on either side of the MEMS flow module 90, or on each side of the MEMS flow module 90. One or more of the noted travel limiters 70, 78 also may be utilized to limit the maximum spacing between the first plate 92 and the second plate 102 as well.

The flow-restricting walls 96 extend from the first plate 92 in the direction of the second plate 102. A gap or space 106 exists between the distal end of each flow-restricting wall 96 and the second plate 102 to provide a desired flow restriction in the illustrated embodiment, although this gap 106 between each of the flow-restricting walls 96 and the second plate 102 may be defined in any appropriate manner one. At least some of the flow entering the MEMS flow module 90 must pass through at least one flow-restricting gap 106 in order to progress completely through the MEMS flow module 90. In the illustrated embodiment, all that is required is for at least some of the flow to pass through only one gap 106 in order to progress completely through the MEMS flow module 90. Any way of providing one or more fluid seals to direct at least some of the flow through at least one gap 106 of the MEMS flow module 90 may be utilized. A portion of the flow through the MEMS flow module 90 may bypass all of its flow-restricting gaps 106 in accordance with the corresponding discussion presented above on the MEMS flow module 34 (e.g., by utilizing one or more etch release holes).

The inward-most annular link 108, the first plate 92, and the second plate 102 may be characterized as collectively defining an enclosed space that may be accessed through the first flow ports 94 and the second flow ports 104 (as well as possibly through one or more etch release holes). The above-noted flow-restricting gaps 106 would exist within this enclosed space. However and as noted above, any way of providing one or more fluid seals to attempt to direct at least some of the flow through a least one flow-restricting gap 106 may be utilized by the MEMS flow module 90. For instance, one or more seals could exist between the MEMS flow module 90 and a housing that incorporates the MEMS flow module 90 so as to attempt to direct at least some of the flow through at least one flow-restricting gap 106.

In the particular configuration presented in FIG. 4C, the first plate 92 would be exposed to the high-pressure side $P_H$ of the MEMS flow module 90, and the second plate 102 flexes at least generally away from the first plate 92 to provide an increased flow or flow rate through the MEMS flow module 90 for the desired pressure regulation function. However, the MEMS flow module 90 could be adapted/installed so that the second plate 102 is exposed to the high-pressure side $P_H$, and such that the first plate 92 flexes at least generally away from the second plate 102 to provide an increased flow or flow rate for the desired pressure regulation function. One embodiment in this respect is presented in FIG. 4D, where common components are identified by the same reference numeral, and where a "single prime" designation is used to identify the existence of at least one structural difference. In the case of the MEMS flow module 90' of FIG. 4D, the flow-restricting walls 96 extend from the second plate 102' toward the first plate 92', such that the flow-restricting walls 96 and the first plate 92' cooperate to define the various flow-restricting gaps 106. Moreover, the first plate 92' flexes at least generally away from the second plate 102' to provide an increased flow or flow rate through the MEMS flow module 90' for the desired pressure regulation function.

The size of each flow-restricting gap 106 may be of any appropriate value when there is no differential pressure across the MEMS flow module 90 (the FIG. 4B position). The size of each flow-restricting gap 106 when there is no differential pressure across the MEMS flow module 90 is no more than about 0.4 microns in one embodiment, is about 0.2 to about 0.3 microns in another embodiment, and is about 0.1 micron or less in yet another embodiment. Each flow-restricting gap 106 may provide a filtering function when there is no differential pressure across the MEMS flow module 90, in addition to providing a desired flow resistance. The size of one or more flow-restricting gaps 106 may be changed to provide at least a pressure-regulation function (e.g., at least some degree of filtering may still be provided at this time as well).

Each flow-restricting gap 106 may be designed such that its corresponding flow-restricting wall 96 and the second plate 102 are spaced to allow at least a certain flow through the MEMS flow module 90 without requiring relative movement between at least part of the first plate 92 and at least part of the second plate 102 to increase the relevant spacing therebetween. That is, the MEMS flow module 90 may be designed to provide a constantly open flow path that allows at least a certain limited flow through the MEMS flow module 90 at all times. Such a constantly open flow path may be beneficial in at least number of respects. One relates to the case where the MEMS flow module 90 is used to relieve intraocular pressure in an eye (e.g., by being incorporated into an eye implant). In this case, the first plate 92 of the MEMS flow module 90 could be on the "anterior chamber" side (e.g., the flow of aqueous humor out of the anterior chamber of the patient's eye through the MEMS flow module 90 would be through one or more of the first flow ports 94, and then through the spacing between the first plate 92 and the second plate 102, and then through one or more of the second flow ports 104). Having a flow path through the MEMS flow module 90 exist at all times (such that it always has a volume greater than zero, but with the flow restriction discussed herein) is believed to at least generally mimic the flow of aqueous humor out of the anterior chamber of a patient's eye through the eye's canal of Schlemm. However, the MEMS flow module 90 could be designed so that the flow-restricting walls 96 are effectively disposed directly on the second plate 102 until at least a certain differential pressure develops (e.g., a differential pressure "set-point"), after which at least part of the first plate 92 and/or at least part of the second plate 102 would flex to open the flow path through the MEMS flow module 90. Stated another way, the MEMS flow module 90 could be designed such that the flow-restricting walls 96 are positioned to at least substantially preclude any flow through the MEMS flow module 90 until at least a certain differential pressure exists across the MEMS flow module 90.

At least one of the first plate 92 or the second plate 102 of the MEMS flow module 90 will flex in response to the existence or development of at least a certain differential pressure across the MEMS flow module 90 to increase the size of one or more flow-restricting gaps 106 (e.g., to change at least one dimension of one or more flow-restricting gaps 106), to decrease the flow resistance through one or more flow-restricting gaps 106, or both to accommodate an increased flow or flow rate through the MEMS flow module 90. Although the amount of differential pressure required to flex one or both of these structures may be of any appropriate magnitude, preferably the relevant structure will flex to at least some degree anytime the differential pressure across the MEMS flow module 90 is greater than zero or anytime there is any change in the differential pressure. As such, flexing will preferably occur anytime the differential pressure across the MEMS flow module 90 is greater than zero or anytime there is any change in the differential pressure. In any case, the MEMS flow module 90 provides a pressure regulation function by the noted flexing.

Figure 4D:
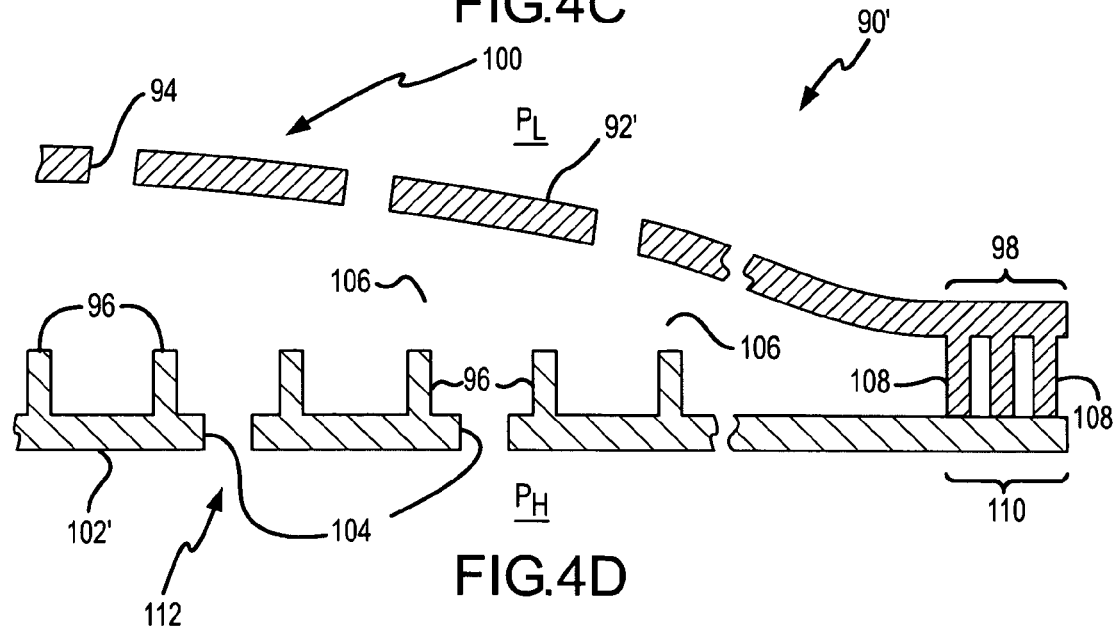
FIG. 4D is a variation of the MEMS flow module of FIG. 4A, where the flow-restricting walls extend from the second plate versus the first plate, and where the first plate versus the second plate is configured to flex in response to experiencing a differential pressure.

The first plate 92 may be configured to be disposed on the "inlet side" or "high-pressure side" of the MEMS flow module 90 (e.g., FIG. 4C), or as in the case of the MEMS flow module 90' of FIG. 4D, the first plate 92' may be configured to be disposed on the "outlet side" or "low-pressure side". Any appropriate size, shape, and/or configuration may be utilized for the first plate 92. As noted, the first flow ports 94 extend completely through the first plate 92. These first flow ports 94 also may be of any appropriate size, shape, and/or configuration, and further may be disposed in any appropriate arrangement. Any appropriate number of first flow ports 94 may be utilized as well.

As noted above, the first region 98 of the first plate 92 is structurally interconnected with the first region 110 of the second plate 102 by one or more annular links 108 in the illustrated embodiment. The first plate 92 also includes a second region 100, which is that portion of the first plate 92 that is disposed inwardly of the inward-most annular link 108. No structural interconnection exists between the second plate 102 and the first plate 92 in its second region 100. All first flow ports 94 are also disposed within the second region 100 of the first plate 92 as well.

The plurality of flow-restricting walls 96, that extend from the first plate 92 in the direction of the second plate 102, cooperate with the second plate 102 to provide the desired degree of flow resistance when the MEMS flow module 90 is in the home position illustrated in FIG. 4B. The discussion presented above with regard to the flow-restricting walls 40 of the MEMS flow module 34 is equally applicable to the flow-restricting walls 96 of the MEMS flow module 90. Once again and for the case of the MEMS flow module 90' of FIG. 4D, it is fabricated such that the flow-restricting walls 96 instead extend from the second plate 102' in the direction of the first plate 92'.

The second plate 102 may be configured to be disposed on the "outlet side" or "low-pressure side" of the MEMS flow module 90 (e.g., FIG. 4C), or as in the case of the MEMS flow module 90' of FIG. 4D, the second plate 102 may be configured to be disposed on the "inlet side" or the "high-pressure side". Any appropriate size, shape, and/or configuration may be utilized for the second plate 102. As noted, the second flow ports 104 extend completely through the second plate 102. These second flow ports 104 also may be of any appropriate size, shape, and/or configuration, and further may be disposed in any appropriate arrangement. Any appropriate number of second flow ports 104 may be utilized as well.

The first region 98 of the first plate 92 is structurally interconnected with the first region 110 of the second plate 102 by one or more annular links 108 in the illustrated embodiment. The second plate 102 also includes a second region 112, which is that portion of the second plate 102 that is disposed inwardly of the inward-most annular link 108. No structural interconnection exists between the first plate 92 and the second plate 102 in its second region 112. All second flow ports 104 are also disposed within the second region 112 of the second plate 102 as well.

Generally, the first flow ports 94 and the second flow ports 104 are arranged so that at least some of the flow entering the MEMS flow module 90 through either a first flow port 94 or a second flow port 104 will have to pass through at least one flow-restricting gap 106 before exiting the MEMS flow module 90 through a first flow port 94 or a second flow port 104. In the illustrated embodiment, all that is required is for at least some of the flow to pass through only one flow-restricting gap 106 in order to progress completely through the MEMS flow module 90. This is accomplished in the illustrated embodiment by disposing the first flow ports 94 and the second flow ports 104 in alternating relation between adjacent pairs of annular flow-restricting walls 96. For instance, one or more first flow ports 94 may be aligned with a first space between first and second flow-restricting walls 96, while no second flow ports 104 are aligned with this first space. One or more second flow ports 104 may be aligned with a second space between second and third flow-restricting walls 96, while no first flow port 94 is aligned with this second space. Therefore a fluid in the first space would have to flow through the flow-restricting gap 106 associated with the second flow-restricting wall 96 before being able to enter the second space, and vice versa.

Typically either the first plate 92 or the second plate 102 will be configured to flex for purposes of accommodating an increased flow or flow rate through the MEMS flow module 90 to provide a pressure regulation function. Consider the configuration of the MEMS flow module 90 of FIGS. 4A-C, where the MEMS flow module 90 is installed such that the first plate 92 is exposed to a high-pressure source $P_H$ and such that the second plate 102 is exposed to a low-pressure source $P_L$. Upon experiencing at least a certain differential pressure, and again preferably anytime the pressure of the high-pressure source $P_H$ is larger than the pressure of the low-pressure source $P_L$, the second region 112 of the second plate 102 (again, that which is disposed inwardly of the inward-most annular link 108) will flex or bulge at least generally away from the first plate 92 (e.g., FIG. 4C) and relative to the first region 110 of the second plate 102 (which should remain in an at least substantially fixed orientation). It should be appreciated a variety of factors may impact how the second region 112 of the second plate 102 actually flexes when exposed to a differential pressure. Any desired "flexing profile" may be utilized for the second plate 102 (e.g., the "shape" of the second plate 102 when exposed to a differential pressure), and this flexing profile may be realized in any appropriate manner. For instance, the second plate 102 could be configured/reinforced in a manner such that two locations that are equally spaced from the geometric center of the second plate 102 will actually flex a different amount when exposed to the same differential pressure.

Having the second plate 102 deflect in the above-noted manner increases the spacing between the distal end of each flow-restricting wall 96 and the second plate 102 (e.g., changes at least one dimension of the associated flow-restricting gap 106) and/or decreases the flow resistance of the associated flow-restricting gap 106, which accommodates a larger flow or flow rate through the MEMS flow module 90. Those flow-restricting walls 96 that are disposed closer to the center of the second plate 102 in the lateral or radial dimension will be spaced further from the second plate 102 (and will thereby have a larger corresponding flow-restricting gap 106) than those flow-restricting walls 96 that are disposed further from the center of the second plate 102 in the illustrated embodiment. Stated another way and for the case of the illustrated embodiment, the spacing between flow-restricting walls 96 and the second plate 102 will increase from flow-restricting wall 96 to flow-restricting wall 96, progressing in the direction of the center of the second plate 102 in the lateral or radial dimension. However and as previously noted, any desired "flexing profile" may be utilized for the second plate 102, and each flexing profile will not necessarily provide spacings between the first plate 92 and the second plate 102 in accordance with the illustrated embodiment. In any case, the noted flexing of the second plate 102 increases the size of the flow-restricting gap 106 associated with a particular flow-restricting wall 96 (e.g., changes at least one dimension of the corresponding flow-restricting gap 106), decreases the flow resistance of the flow-restricting gap 106 associated with a particular flow-restricting wall 96, or both, to accommodate a larger flow or flow rate through the MEMS flow module 90.

It should be appreciated that the foregoing discussion would be equally applicable to having the flow-restricting walls 96 extend from the second plate 102 toward the first plate 92. Flexing of the second plate 102 away from the first plate 92 in the above-noted manner will still change at least one dimension of each flow-restricting gap 106 and/or decrease the flow resistance of each such flow-restricting gap 106, thereby accommodating a larger flow or flow rate through the MEMS flow module 90. While it may be desirable for the entire first plate 92 to remain in an at least substantially fixed orientation (e.g., such that the entire first plate 92 does not flex or otherwise change shape to any significant degree) during flexing of the second plate 102 to provide a pressure regulation function, it should be appreciated that at least some flexing of the first plate 92 in the direction of the second plate 102 could occur and yet still allow the MEMS flow module 90 to accommodate a higher flow or flow rate when the pressure of the high-pressure source $P_H$ exceeds the pressure of the low-pressure source $P_L$. Generally, the second plate 102 would have to flex more than the first plate 92 when the pressure of the high-pressure source $P_H$ exceeds the pressure of the low-pressure source $P_L$ in order for the MEMS flow module 90 to accommodate an increased flow or flow rate through the MEMS flow module 90 in this case.

Now consider the configuration of the MEMS flow module 90' of FIG. 4D, where the MEMS flow module 90' is installed such that the first plate 92' is exposed to a low-pressure source $P_L$ and such that the second plate 102' is exposed to a high-pressure source $P_H$. Upon experiencing at least a certain differential pressure, and again preferably anytime the pressure of the high-pressure source $P_H$ is larger than the pressure of the low-pressure source $P_L$, the second region 100 of the first plate 92' (again, that which is disposed inwardly of the inward-most annular link 108) will flex or bulge at least generally away from the second plate 102' and relative to the first region 98 of the first plate 92' (which should remain in an at least substantially fixed position, or where the first region 98 of the first plate 92 does not flex or otherwise change shape to any significant degree). It should be appreciated that a variety of factors may impact how the second region 100 of the first plate 92' flexes when exposed to a differential pressure. Any desired "flexing profile" may be utilized for the first plate 92' (e.g., the "shape" of the first plate 92' when exposed to a differential pressure), and this flexing profile may be realized in any appropriate manner. For instance, the first plate 92' could be configured/reinforced in a manner such that two locations that are equally spaced from the geometric center of the first plate 92' will actually flex a different amount when exposed to the same differential pressure.

Having the first plate 92' deflect in the above-noted manner changes at least one dimension of the spacing between each flow-restricting wall 96 and the second plate 102' and/or the flow resistance of the associated flow-restricting gap 106, which accommodates a larger flow or flow rate through the MEMS flow module 90'. Those flow-restricting walls 96 that are disposed closer to the center of the first plate 92' in the lateral or radial dimension will be spaced further from the first plate 92' (and will thereby have a larger corresponding flow-restricting gap 106) than those flow-restricting walls 96 that are disposed further from the center of the first plate 92' in the illustrated embodiment. Stated another way and for the case of the illustrated embodiment, the spacing between flow-restricting walls 96 and the first plate 92' will increase from flow-restricting wall 96 to flow-restricting wall 96, progressing toward the center of the first plate 92' in the lateral or radial dimension. In any case, the flexing of the first plate 92' increases the size of the flow-restricting gap 106 associated with a particular flow-restricting wall 96 (e.g., changes at least one dimension of such a flow-restricting gap 106), decreases the flow resistance of the flow-restricting gap 106 associated with a particular flow-restricting wall 96, or both to accommodate a larger flow or flow rate through the MEMS flow module 90'.

It should be appreciated that the foregoing discussion would be equally applicable to having the flow-restricting walls 96 extend from the first plate 92' toward the second plate 102'. Flexing of the first plate 92' away from the second plate 102' in the above-noted manner will still change at least one dimension of each flow-restricting gap 106 and/or decrease the flow resistance of each such flow-restricting gap 106, thereby accommodating a larger flow or flow rate through the MEMS flow module 90'. While it may be desirable for the second plate 102' to remain in an at least substantially fixed orientation (e.g., such that the second plate 102' does not flex or otherwise change shape to any significant degree in this case) during flexing of the first plate 92' to provide a pressure regulation function, it should be appreciated that at least some flexing of the second plate 102' in the direction of the first plate 92' could occur and yet still allow the MEMS flow module 90' to accommodate a higher flow or flow rate when the pressure of the high-pressure source $P_H$ exceeds the pressure of the low-pressure source $P_L$. Generally, the first plate 92' would have to flex more than the second plate 102' when the pressure of the high-pressure source $P_H$ exceeds the pressure of the low-pressure source $P_L$ in order for the MEMS flow module 90' to accommodate an increased flow or flow rate through the MEMS flow module 90' in this case.

Figure 4E:
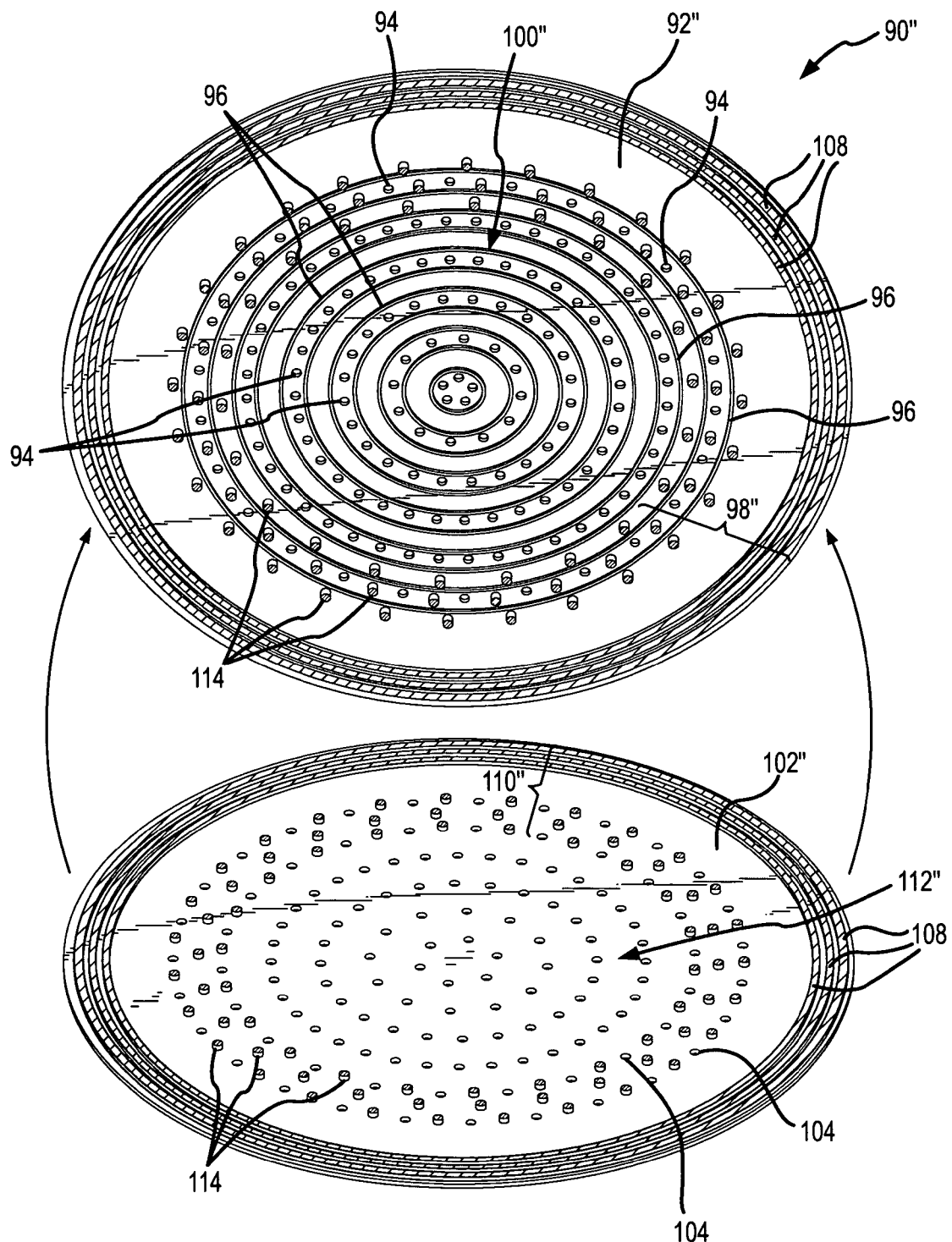
FIG. 4E is a cross-sectional, exploded, perspective view of a variation of the MEMS flow module of FIG. 4A, that includes both fixed filter section and a pressure-regulator section.

A variation of the MEMS flow module 90 of FIG. 4A is presented in FIG. 4E and is identified by reference numeral 90". Corresponding components of these two embodiments are identified by the same reference numeral, and the above-noted discussion remains equally applicable unless otherwise noted. Those components that differ in at least some respect are identified by a "double prime" designation in the FIG. 4E embodiment.

The primary difference between the MEMS flow module 90 of FIG. 4A and the MEMS flow module 90" of FIG. 4E is that the first region 98" of the first plate 92" and the first region 110" of the second plate 102" have each been extended so as to include at least some first flow ports 94, at least some second flow ports 104, and at least one flow-restricting wall 96 (two in the illustrated embodiment). Any number of flow-restricting walls 96 could be associated within the first region 98" of the first plate 92" and the first region 110" of the second plate 102". Once again, the first region 98" of the first plate 92" and the first region 110" of the second plate 102" each remain in an at least substantially fixed orientation (e.g., such that the first region 98" of the first plate 92" and the first region 110" of the second plate 102" do not flex or otherwise change shape to any significant degree) during exposure to the anticipated differential pressures for which the MEMS flow module 90" was designed.

The above-noted "extension" of the first region 98" of the first plate 92" and the first region 110" of the second plate 102" is accomplished by adding a plurality of structural interconnects 114 (e.g., columns, posts, or the like) that structurally interconnect the first plate 92" and the second plate 102". Each structural interconnect 114 may be of any appropriate size, shape, and configuration, and the various structural interconnects 114 may be distributed in any appropriate arrangement. Preferably, the structural interconnects 114 at least substantially retain a corresponding annular portion of each of the first plate 92" and the second plate 102" in an at least substantially fixed orientation (e.g., such that a corresponding annular portion of each of the first plate 92" and the second plate 102" do not flex or otherwise change shape to any significant degree).

The MEMS flow module 90" may be characterized as including a fixed filter section and a pressure-regulating section. The fixed filter section is in the form of at least part of the first region 98" of the first plate 92" and the first region 110" of the second plate 102". A "fixed filter section" characterization is used since the size or magnitude of the flow restriction associated with each flow-restricting wall 96 that interacts with the first region 110" of the second plate 102" remains at least substantially constant, regardless of the differential pressure to which the MEMS flow module 90" is exposed. Stated another way, since neither the first region 98" of the first plate 92" nor the first region 110" of the second plate 102" flexes to any significant degree upon experiencing a differential pressure within the design limits of the MEMS flow module 90", the magnitude of a flow restriction provided by an associated flow-restricting wall 96 will not appreciably change. Therefore, this portion of the MEMS flow module 90" provides a filtering function using an at least substantially constant pore size (corresponding with the size of the gaps 106 associated with the first region 110" of the second plate 102").

The MEMS flow module 90" provides a pressure-regulating function in the same general manner as discussed above in relation to the MEMS flow module 90. That is, one or both of the second region 100" of the first plate 92" and the second region 112" of the first plate 102" will flex upon experiencing a differential pressure to accommodate an increased flow through the MEMS flow module 90" (e.g., by changing at least one dimension of at least one flow-restricting gap 106, by decreasing the flow resistance of at least one flow-restricting gap 106, or both). It should be appreciated that the size of the first region 98" and the second region 100" of the first plate 92", as well as the size of the first region 110" and the second region 112" of the second plate 102", may be selected as desired/required. Moreover, any number of flow-restricting walls 96 may be associated with either region (fixed-filter or pressure regulator) of the MEMS flow module 90".

Figure 5A:
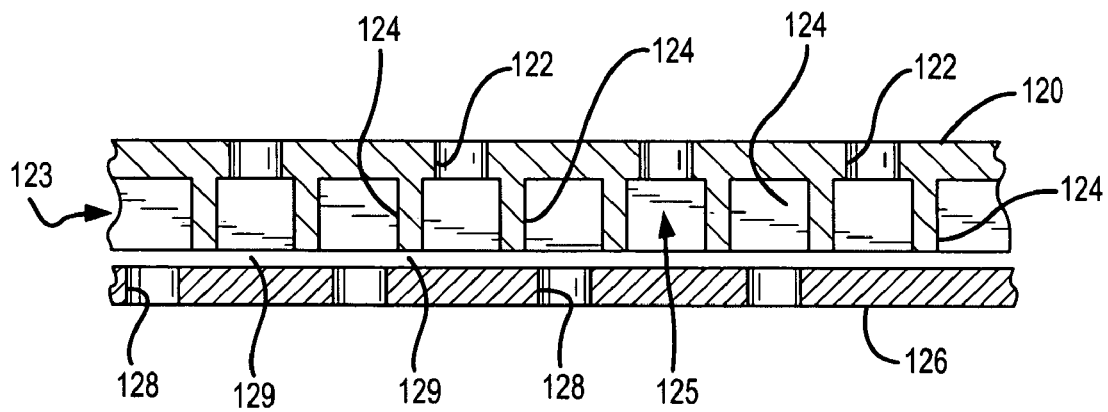
FIG. 5A is a cross-sectional view of one embodiment of a grid of flow-restricting walls that may be used by any of the MEMS flow modules described herein.
Figure 5B:
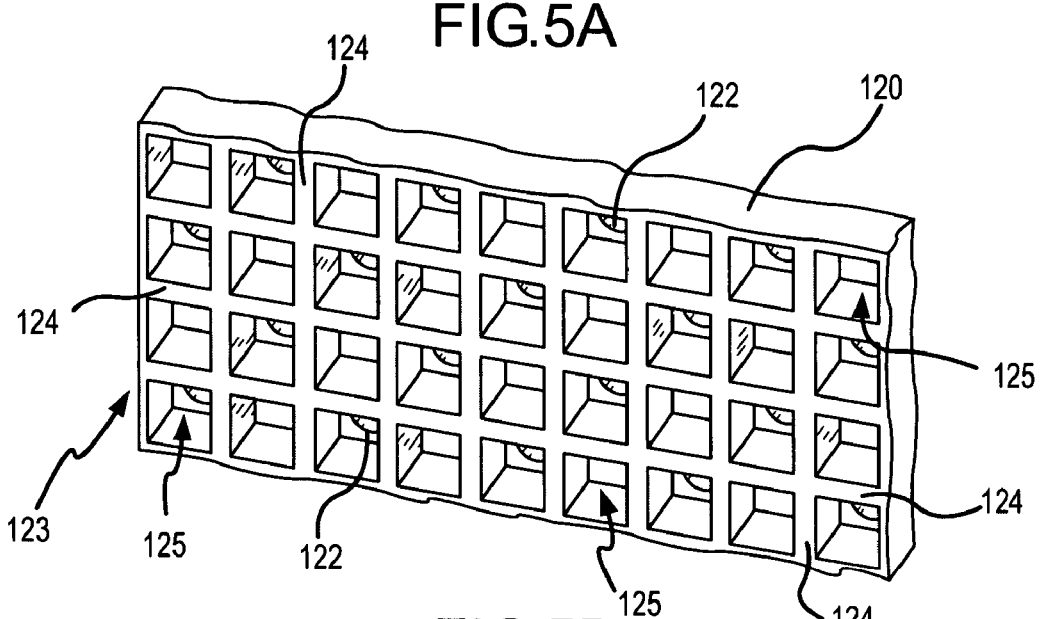
FIG. 5B is a perspective view of the grid of flow-restricting walls from FIG. 5A.

The above-described MEMS flow modules may utilize a plurality of annular flow-restricting walls that are concentrically disposed. Other configurations for flow-restricting structures may be appropriate as previously noted, other arrangements of flow-restricting structures may be appropriate, or both. One example is illustrated in FIGS. 5A-B, where a first plate 120 and a second plate 126 are disposed in spaced relation. The first plate 120 includes a plurality of first flow ports 122, while the second plate 126 includes a plurality of second flow ports 128. What may be characterized as a grid 123 of flow-restricting walls 124 extends from the first plate 120 toward the second plate 126. These flow-restricting walls 124 intersect with each other to define a plurality of cavities 125. It should be appreciated that the grid 123 may be of any appropriate size, shape, and configuration. For instance, the cavities 125 could be of any appropriate shape in plan view (e.g., rectangular, circular, elliptical) by appropriately configuring/arranging the flow-restricting walls 124.

Each cavity 125 is surrounded by a continuous boundary of flow-restricting walls 124 that collectively define an annular flow-restricting structure. The flow-restricting walls 124 may be of any appropriate size, shape, and configuration, and further may be disposed in any appropriate arrangement to define the desired cavity 125. In any case, some of the cavities 125 are aligned with and fluidly communicate with at least one first flow port 122. Other cavities 125 are aligned with and fluidly communicate with at least one second flow port 128. No cavity 125 is aligned with both a first flow port 122 and a second flow port 128. Instead, a flow entering a particular cavity 125 is required to pass through at least one flow restriction before entering another cavity 125.

A flow-restricting gap 129 exists between each flow-restricting wall 124 and the second plate 126. Generally, the first flow ports 122 and the second flow ports 128 are arranged such that all fluid communication between any first flow port 122 and any second flow port 128 requires that a flow pass through at least one flow-restricting gap 129. Consider the case where a flow enters a cavity 125 through a first flow port 122. This flow would have to pass through at least one flow-restricting gap 129 before reaching any cavity 125 where this flow could exit through a second flow port 128. The reverse would be true as well. That is, a flow entering a cavity 125 through a second flow port 128 would have to pass through at least one flow-restricting gap 129 before reaching any cavity 125 where this flow could exit through a first flow port 122. In the illustrated embodiment, all that is required is for at least some of the flow to pass through only one gap 129 in order to progress completely through the first plate 120 and the second plate 126. As in the case of the MEMS flow modules 34 and 90, part of the flow through a MEMS flow module that utilizes the first plate 120 and the second plate 126 could bypass all of its flow-restricting gaps 129 in accordance with the corresponding discussion presented above on the MEMS flow module 34 (e.g., by utilizing one or more etch release holes).

The configuration presented in FIGS. 5A-B could be utilized in any of the above-noted embodiments. That is, one or both of the first plate 120 and second plate 126 may flex in at least some manner to increase the size of at least one flow-restricting gap 129 (e.g., to change at least one dimension of at least one flow-restricting gap 129) and/or decrease the flow resistance of at least one flow-restricting gap 129 in order to accommodate an increased flow or flow rate through a MEMS flow module incorporating the plates 120, 126 and upon experiencing a pressure differential. It should be appreciated that the flow-restricting walls 124 could extend from the second plate 126, such that the flow-restricting gaps 129 are defined between the flow-restricting walls 124 and the first plate 120 (not shown).

Figure 6:
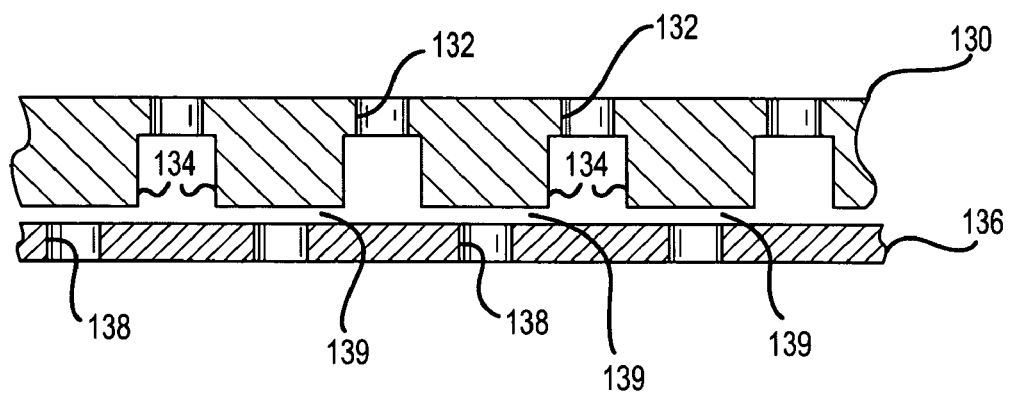
FIG. 6 is a cross-sectional view of flow-restricting plugs that may be used by any of the MEMS flow modules described herein.

Another example of a flow-restricting structure is illustrated in FIG. 6, where a first plate 130 and a second plate 136 are disposed in spaced relation. The first plate 130 includes a plurality of first flow ports 132, while the second plate 136 includes a plurality of second flow ports 138. A plurality of flow-restricting plugs 134 extend from the first plate 130 toward the second plate 136. Each flow-restricting plug 134 may be of any appropriate size, shape, and configuration. Representative configurations in plan view for the flow-restricting plugs 134 include circular, square, rectangular, and elliptical. In any case, a flow-restricting gap 139 exists between each flow-restricting plug 134 and the second plate 136. Generally, the first flow ports 132 and the second flow ports 138 are arranged such that all fluid communication between any first flow port 132 and any second flow port 138 requires that a flow pass through at least one flow-restricting gap 139. In the illustrated embodiment, all that is required is for at least some of the flow to pass through only one gap 139 in order to progress completely through the first plate 130 and second plate 136. In the illustrated embodiment, this is provided by disposing each flow-restricting plug 134 over a particular second flow port 138. One or more of the flow-restricting plugs 134 could of course be disposed over multiple second flow ports 138. It also may be possible for one or more flow-restricting plugs 134 to be configured to extend within a corresponding second flow port 138 (not shown). Although it would be preferred for any such flow-restricting plug 134 to remain spaced from the second plate 136, this may not be required in all instances. As in the case of the MEMS flow modules 34 and 90, part of the flow through a MEMS flow module that utilizes the first plate 130 and the second plate 136 could bypass all of its flow-restricting gaps 139 in accordance with the corresponding discussion presented above on the MEMS flow module 34 (e.g., by utilizing one or more etch release holes).

One or more of the above-noted flow-restricting plugs 134 could be replaced by an annular flow-restricting wall of any appropriate size, shape, and configuration as well. A flow-restricting gap in accordance with the flow-restricting gap 139 would be provided between each such annular flow-restricting wall and the second plate 136. One or more first flow ports 132 could interface with the hollow interior of each such annular flow-restricting wall, while one or more second flow ports 138 could be disposed beyond the perimeter of each such annular flow-restricting wall. The arrangement of the first flow ports 132 and the second flow ports 138 relative to each annular flow-restricting wall could be reversed as well.

The configuration presented in FIG. 6 could be utilized in any of the above-noted embodiments. That is, one or both of the first plate 130 and second plate 136 may flex in at least some manner to increase the size of at least one flow-restricting gap 139 (e.g., change at least one dimension of at least one flow-restricting gap 139) and/or decrease the flow resistance of one or more flow-restricting gaps 139 in order to accommodate an increased flow or flow rate through a MEMS flow module incorporating the plates 130, 136 and upon experiencing a pressure differential. It should be appreciated that the flow-restricting plugs 134 (and the noted variations thereof) could extend from the second plate 136, such that the flow-restricting gaps 139 are defined between the flow-restricting plugs 134 and the first plate 130 (not shown).

Figure 7:
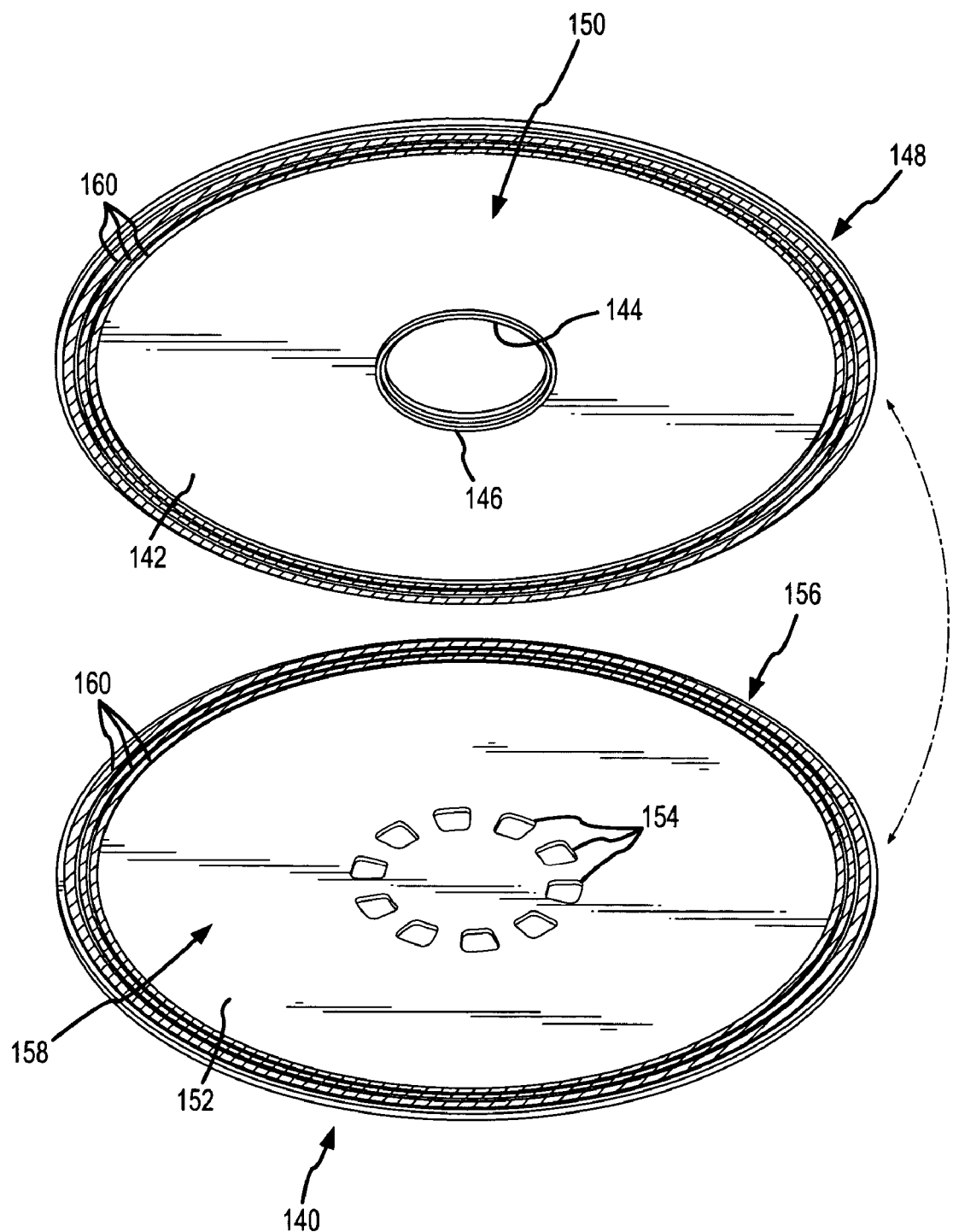
FIG. 7 is a cross-sectional, exploded, perspective view of another embodiment of MEMS flow module that uses a flexing diaphragm for regulating pressure.

Another embodiment of a MEMS flow module is illustrated in FIG. 7, is identified by reference numeral 140, and provides at least a pressure regulation function by a flexing diaphragm. The MEMS flow module 140 is fundamentally similar to the MEMS flow modules 90, 90' that were discussed above in relation to FIGS. 4A-D. Although the MEMS flow module 140 is illustrated as having a circular configuration in plan view, any appropriate configuration may be utilized and in any appropriate size.

FIG. 7 shows an exploded, perspective view of the MEMS flow module 140. Specifically, FIG. 7 is a cross-section of the MEMS flow module 140 that is taken along a plane that is parallel to its first plate 142, at a location that is between the first plate 142 and its second plate 152 so as to extend through a flow-restricting gap between the distal end of an annular flow-restricting wall 146 and the second plate 152, and with the first plate 142 having been rotated or pivoted away from the second plate 152. Generally, at least one of the first plate 142 and the second plate 152 flexes to increase the spacing between these two structures, to in turn accommodate an increased flow or flow rate through the MEMS flow module 140. Once again, preferably this is by an elastic deformation. The elasticity may then at least contribute to returning the relevant structure back toward its original position upon a subsequent reduction of the differential pressure.

As shown in FIG. 7, the MEMS flow module 140 includes a first plate 142 (e.g., fabricated in $P_3$ layer 26) having at least one first flow port 144 that extends completely through the first plate 142, a second plate 152 (e.g., fabricated at least in $P_2$ layer 22) having at least one second flow port 154 that extends completely through the second plate 152 (preferably a plurality of second flow ports 154 are associated with each first flow port 144), and a single annular flow-restricting wall 146 (e.g., fabricated in $P_3$ layer 26) for each first flow port 144. In the case where there is only a single first flow port 144, it may be desirable to dispose the same at the geometric center of the first plate 142. However, it could be disposed at other locations as well. Multiple first flow ports 144 may be disposed in any appropriate arrangement.

A first region 148 of the first plate 142 and a first region 156 of the second plate 152 include one or more structural interconnections between the first plate 142 and the second plate 152. Preferably, this structural interconnection is in the form of at least one annular connector, wall, or link 160 of any appropriate size, shape, and/or configuration. This not only disposes the first plate 142 and the second plate 152 in spaced relation, but provides at least one radial seal—namely a seal that reduces the potential of fluid exiting the MEMS flow module 140 through the space between the first plate 142 and the second plate 152. Using multiple, radially-spaced annular links 160 would thereby provide multiple, radially-spaced radial seals. Other types of structural connections could exist in the first region 148 of the first plate 142 and the first region 156 of the second plate 152 if such a "radial seal" function was not desired or required. For instance, one or more seals could be provided between a housing(s) that incorporates the MEMS flow module 140 and another structure to attempt to direct all flow through MEMS flow module 140. In any case, the first region 148 of the first plate 142 and the first region 156 of the second plate 152 generally are at least substantially maintained in a fixed orientation (e.g., such that the first region 148 of the first plate 142 and the first region 156 of the second plate 152 do not flex or otherwise change shape to any significant degree) during use of the MEMS flow module 140 in the anticipated conditions.

The MEMS flow module 140 may include various features from the MEMS flow module 34 of FIGS. 2A-C. The noted annular support 64 may be interconnected with the first plate 142 by one or more of the noted annular connectors, walls, or links 66 so as to "sandwich" the first plate 142 between the annular support 64 and the second plate 152. A ring 68 could be disposed on either side of the MEMS flow module 140, or on each side of the MEMS flow module 140, or both. One or more of the noted travel limiters 70, 78 also may be utilized to limit the maximum spacing between the first plate 142 and the second plate 152.

The annular flow-restricting wall 146 extends from the first plate 142 in the direction of the second plate 152. A gap or space exists between the distal end of the annular flow-restricting wall 146 and the second plate 152 to provide a desired flow restriction, although any appropriate way of providing a gap between the annular flow-restricting wall 146 and the second plate 152 could be utilized. At least some of the flow entering the MEMS flow module 140 must pass through this type of flow-restricting gap in order to progress completely through the MEMS flow module 140. The inward-most annular link 160, the first plate 142, and the second plate 152 may be characterized as collectively defining an enclosed space that may be accessed through the first flow port 144 and the second flow ports 154 (as well as possibly through one or more etch release holes). The above-noted flow-restricting gap would exist within this enclosed space. However and as noted above, the MEMS flow module 140 need not include one or more radial seals between perimeter portions of the first plate 142 and the second plate 152. Instead, one or more other fluid seals may be used to attempt to force at least some of the flow through the flow-restricting gap of the MEMS flow module 140.

The size of the above-noted flow-restricting gap may be of any appropriate value when there is no differential pressure across the MEMS flow module 140. The size of this flow-restricting gap when there is no differential pressure across the MEMS flow module 140 is no more than about 0.4 microns in one embodiment, is about 0.2 to about 0.3 microns in another embodiment, and is about 0.1 micron or less in yet another embodiment. This flow-restricting gap may provide a filtering function when there is no differential pressure across the MEMS flow module 140, in addition to providing a desired flow resistance. As will be discussed in more detail below, at least one of the first plate 142 and the second plate 152 may flex in response to a differential pressure to change at least one dimension of the flow-restricting gap, to decrease the flow resistance of the flow-restricting gap, or both to accommodate an increased flow or flow rate through the MEMS flow module 140. At this time, at least some degree of filtering may still be provided by the MEMS flow module 140.

The MEMS flow module 140 may be designed such that the annular flow-restricting wall 146 and the second plate 102 are spaced to allow at least a certain flow through the MEMS flow module 140 without requiring relative movement between at least part of the first plate 142 and at least part of the second plate 152 to increase the spacing therebetween. That is, the MEMS flow module 140 may be designed to provide a constantly open flow path that allows at least a certain limited flow through the MEMS flow module 140 at all times. Such a constantly open flow path may be beneficial in at least number of respects. One relates to the case where the MEMS flow module 140 is used to relieve intraocular pressure in an eye (e.g., by being incorporated into an eye implant). In this case, either the first plate 142 or the second plate 152 of the MEMS flow module 140 could be on the "anterior chamber" side. Having a flow path through the MEMS flow module 140 exist at all times (such that it always has a volume greater than zero, but with the flow restriction discussed herein by a desired spacing between the annular flow-restricting wall 146 and the second plate 152) is believed to at least generally mimic the flow of aqueous humor out of the anterior chamber of a patient's eye through the eye's canal of Schlemm. However, the MEMS flow module 140 could be designed so that the annular flow-restricting wall 146 is effectively disposed directly on the second plate 152 until at least a certain differential pressure develops (e.g., a differential pressure "set-point"), after which the at least part of the first plate 142 and/or at least part of the second plate 152 would flex to open the flow path through the MEMS flow module 140. Stated another way, the MEMS flow module 140 could be designed such that the annular flow-restricting wall 146 is positioned to at least substantially preclude any flow through the MEMS flow module 140 until at least a certain differential pressure exists across the MEMS flow module 140.

At least one of the first plate 142 or the second plate 152 of the MEMS flow module 140 will flex in response to the existence or development of at least a certain differential pressure across the MEMS flow module 140 to increase the size of the flow-restricting gap between the annular flow-restricting wall 146 and the second plate 152 (e.g., to change at least one dimension of this flow-restricting gap) to decrease the flow resistance of this flow-restricting gap, or both to accommodate an increased flow or flow rate through the MEMS flow module 140. Although the amount of differential pressure required to flex one or both of these structures may be of any appropriate magnitude, preferably the relevant structure will flex to at least some degree anytime the differential pressure across the MEMS flow module 140 is greater than zero or anytime there is any change in the differential pressure. As such, flexing will preferably occur anytime the differential pressure across the MEMS flow module 140 is greater than zero or anytime there is any change in the differential pressure. In any case, the MEMS flow module 140 provides a pressure regulation function by the noted flexing.

The first plate 142 may be configured to be disposed on the "inlet side" or "high-pressure side" of the MEMS flow module 140, or may be configured to be disposed on the "outlet side" or "low-pressure side" of the MEMS flow module 140. Any appropriate size, shape, and/or configuration may be utilized for the first plate 142. As noted, the first flow port 144 extends completely through the first plate 142. This first flow port 144 also may be of any appropriate size, shape, and/or configuration. In one embodiment, the surface area of the first flow port 144 is at least about 2,000 $\mu m^2$ (in plan view). Multiple first flow ports 144 could be utilized as well, each having a corresponding annular flow-restricting wall 146.

As noted above, the first region 148 of the first plate 142 is structurally interconnected with the first region 156 of the second plate 152 by one or more annular links 160 in the illustrated embodiment. The first plate 142 also includes a second region 150, which is that portion of the first plate 142 that is disposed inwardly of the inward-most annular link 160. No structural interconnection exists between the second plate 152 and the first plate 142 in its second region 150. All first flow ports 144 would also be disposed within the second region 150 of the first plate 142 as well.

The annular flow-restricting wall 146, that extends from the first plate 142 in the direction of the second plate 152, cooperates with the second plate 152 to provide the desired degree of flow resistance when there is no differential pressure across the MEMS flow module 140. "Annular" again means that the flow-restricting wall 146 extends a full 360 degrees about a common point, and does not limit the flow-restricting wall 146 to having a circular configuration. Other types of flow-restricting structures could be utilized as well. For instance, the flow-restricting wall 146 could be replaced by a plurality of flow-restricting segments of any appropriate size/shape/configuration, where adjacent pairs of flow-restricting segments would be appropriately spaced from each other (e.g., conceptually, a gap could be introduced in the flow-restricting wall 146 at each of a plurality of locations). The gap between such flow-restricting segments and the second plate 152, as well as the gap between each adjacent pair of flow-restricting segments, would provide the desired degree of flow restriction when there is no differential pressure across the MEMS flow module 140.

The second plate 152 may be configured to be disposed on the "outlet side" or "low-pressure side" of the MEMS flow module 140, or may be configured to be disposed on the "inlet side" or the "high-pressure side" of the MEMS flow module 140. Any appropriate size, shape, and/or configuration may be utilized for the second plate 152. As noted, the second flow ports 154 extend completely through the second plate 152. These second flow ports 154 also may be of any appropriate size, shape, and/or configuration, and further may be disposed in any appropriate arrangement. Any appropriate number of second flow ports 154 may be utilized as well.

Once again, the first region 148 of the first plate 142 is structurally interconnected with the first region 156 of the second plate 152 by one or more annular links 160 in the illustrated embodiment. The second plate 152 also includes a second region 158, which is that portion of the second plate 152 that is disposed inwardly of the inward-most annular link 160. No structural interconnection exists between the first plate 142 and the second plate 152 in its second region 158. All second flow ports 154 are also disposed within the second region 158 of the second plate 152 as well.

Typically either the first plate 142 or the second plate on 52 will be configured to flex for purposes of accommodating an increased flow or flow rate through the MEMS flow module 140 to provide a pressure regulation function. Consider the case where the MEMS flow module 140 is installed such that the first plate 142 is exposed to a high-pressure source and such that the second plate 152 is exposed to a low-pressure source. Upon experiencing at least a certain differential pressure, and again preferably anytime the pressure of the high-pressure source is larger than the pressure of the low-pressure source, the second region 158 of the second plate 152 (again, that which is disposed inwardly of the inward-most annular link 160) will flex or bulge at least generally away from the first plate 142 and relative to the first region 156 of the second plate 152 (which should remain in an at least substantially fixed orientation). It should be appreciated that a variety of factors may impact how the second region 158 of the second plate 152 flexes when exposed to a differential pressure. Any desired "flexing profile" may be utilized for the second plate 152 (e.g., the "shape" of the second plate 152 when exposed to a differential pressure), and this flexing profile may be realized in any appropriate manner. For instance, the second plate 152 could be configured/reinforced in a manner such that two locations that are equally spaced from the geometric center of the second plate 152 will actually flex a different amount when exposed the same differential pressure.

Having the second plate 152 deflect in the above-noted manner changes at least one dimension of the spacing between the flow-restricting wall 146 and the second plate 152, decreases the flow resistance by this spacing, or both, which accommodates a larger flow or flow rate through the MEMS flow module 140. While it may be desirable for the entire first plate 142 to remain in an at least substantially fixed orientation (e.g., such that the entire first plate 142 does not flex or otherwise change shape to any significant degree) during flexing of the second plate 152 to provide a pressure regulation function, it should be appreciated that at least some flexing of the first plate 142 in the direction of the second plate 152 could occur and yet still allow the MEMS flow module 140 to accommodate a higher flow or flow rate when the pressure of the high-pressure source exceeds the pressure of the low-pressure source. Generally, the second plate 152 would have to flex more than the first plate 142 when the pressure of the high-pressure source exceeds the pressure of the low-pressure source in order for the MEMS flow module 140 to accommodate an increased flow or flow rate through the MEMS flow module 140 in this first example.

Now consider the case where the MEMS flow module 140 is installed such that the second plate 152 is exposed to a high-pressure source and such that the first plate 142 is exposed to a low-pressure source. Upon experiencing at least a certain differential pressure, and again preferably anytime the pressure of the high-pressure source is larger than the pressure of the low-pressure source, the second region 150 of the first plate 142 (again, that which is disposed inwardly of the inward-most annular link 160) will flex or bulge at least generally away from the second plate 152 and relative to the first region 148 of the first plate 142 (which should remain in an at least substantially fixed orientation). It should be appreciated that a variety of factors may impact how the second region 150 of the first plate 142 actually flexes when exposed to a differential pressure. Any desired "flexing profile" may be used for the first plate 142 (e.g., the "shape" of the first plate 142 when exposed to a differential pressure), and this flexing profile may be realized in any appropriate manner.

Having the first plate 142 deflect in the above-noted manner changes at least one dimension the spacing between the flow-restricting wall 146 and the second plate 152, decreases the flow resistance associated this spacing, or both, which accommodates a larger flow or flow rate through the MEMS flow module 140. While it may be desirable for the entire second plate 152 to remain in an at least substantially fixed orientation (e.g., such that the entire second plate 152 does not flex or otherwise change shape to any significant degree) during flexing of the first plate 142 to provide a pressure regulation function, it should be appreciated that at least some flexing of the second plate 152 in the direction of the first plate 142 could occur and yet still allow the MEMS flow module 140 to accommodate a higher flow or flow rate when the pressure of the high-pressure source exceeds the pressure of the low-pressure source. Generally, the first plate 142 would have to flex more than the second plate 152 when the pressure of the high-pressure source exceeds the pressure of the low-pressure source in order for the MEMS flow module 140 to accommodate an increased flow or flow rate through the MEMS flow module 140 in this second example.

Surface micromachining is the preferred technology for fabricating the above-described MEMS flow modules having a diaphragm that flexes in response to experiencing at least a certain change in a differential pressure across the MEMS flow module. In this regard, the above-noted MEMS flow modules may be suspended above the substrate 10 after the release by one or more suspension tabs that are disposed about the perimeter of the MEMS flow module, that engage an appropriate portion of the MEMS flow module, and that are anchored to the substrate. These suspension tabs may be fractured or broken (e.g., by application of the mechanical force; electrically, such as by directing an appropriate current through the suspension tabs) to structurally disconnect the MEMS flow module from the substrate 10. One or more motion limiters may be fabricated and disposed about the perimeter of the MEMS flow module as well to limit the amount that the MEMS flow module may move in the lateral or radial dimension after the suspension tabs have been fractured and prior to retrieving the disconnected MEMS flow module. Representative suspension tabs and motion limiters are disclosed in commonly owned U.S. patent application Ser. No. 11/048,195, that was filed on Feb. 1, 2005, that is entitled "MEMS FLOW MODULE WITH PIVOTING-TYPE BAFFLE," and the entire disclosure of which is incorporated by reference herein.

Figure 8A:
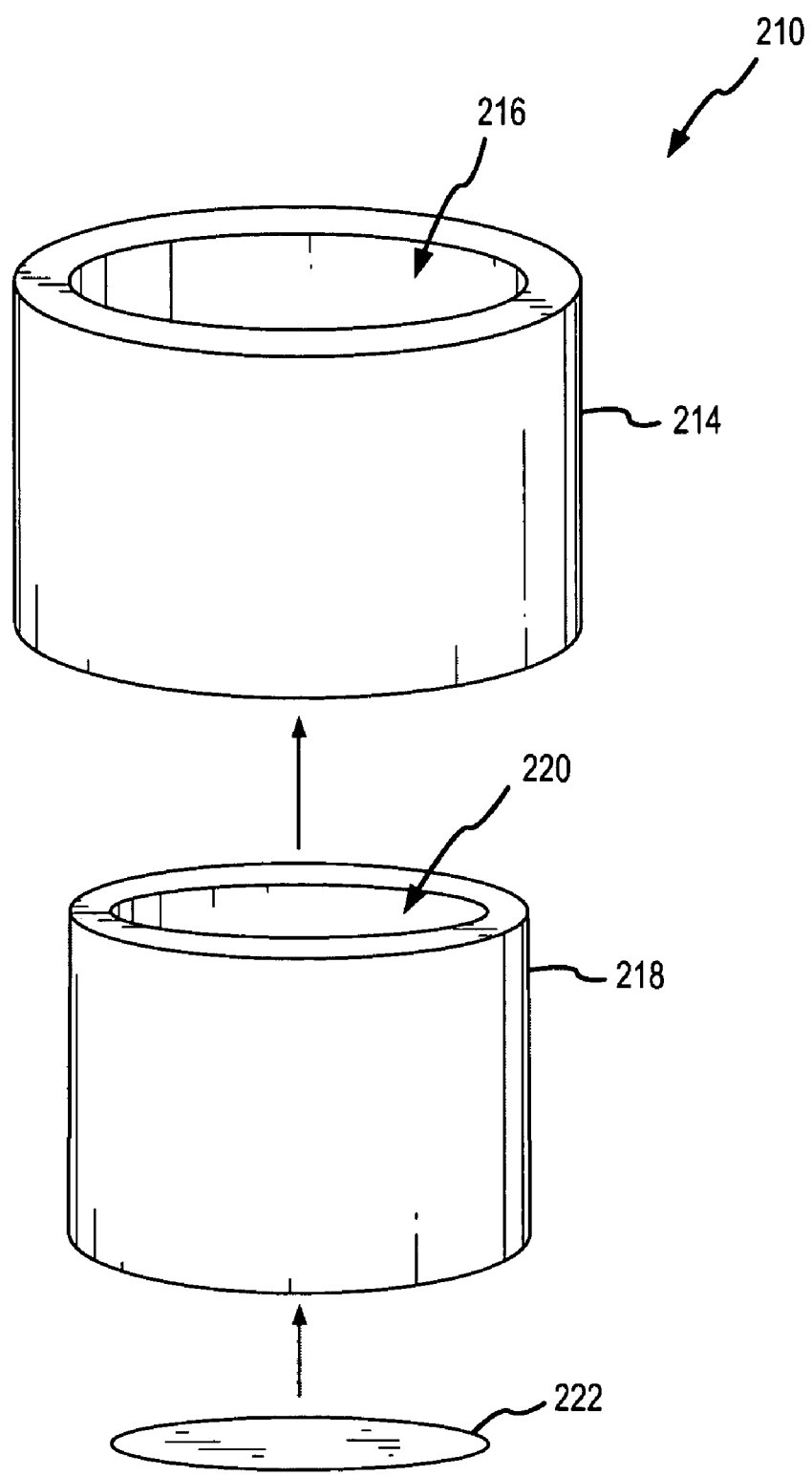
FIG. 8A is an exploded, perspective view of one embodiment of a flow assembly that uses a MEMS flow module.
Figures 8B, 10A:
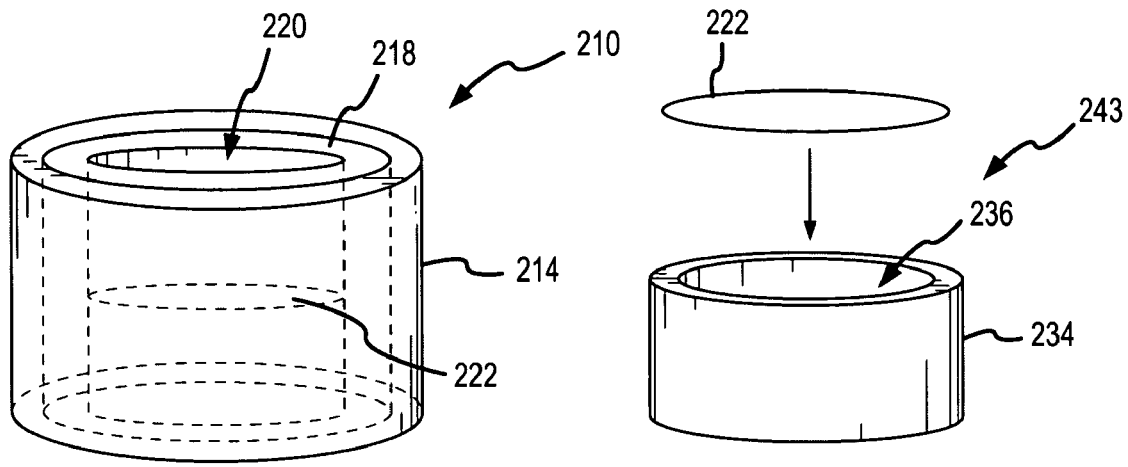
FIG. 8B is a perspective view of the flow assembly of FIG. 8A in an assembled condition.
FIG. 10A is an exploded, perspective of another embodiment of a flow assembly that uses a MEMS flow module.

FIGS. 8A-B schematically represent one embodiment of a flow assembly 210 that may be used for any appropriate application (e.g., the flow assembly 210 may be disposed in a flow of any type, may be used to filter and/or control the flow of a fluid of any type, may be located in a conduit that fluidly interconnects multiple sources of any appropriate type (e.g., between multiple fluid or pressure sources (including where one is the environment), such as a man-made reservoir, a biological reservoir, the environment, or any other appropriate source), or any combination thereof). One example would be to dispose the flow assembly 210 in a conduit extending between the anterior chamber of an eye and a location that is exterior of the cornea of the eye. Another example would be to dispose the flow assembly 210 in a conduit extending between the anterior chamber of an eye and another location that is exterior of the sclera of the eye. Yet another example would be to dispose the flow assembly 210 in a conduit extending between the anterior chamber of an eye and another location within the eye (e.g., into Schlemm's canal) or body. In each of these examples, the conduit would provide an exit path for aqueous humor when installed for a glaucoma patient. That is, each of these examples may be viewed as a way of treating glaucoma or providing at least some degree of control of the intraocular pressure.

Components of the flow assembly 210 include an outer housing 214, an inner housing 218, and a MEMS flow module 222. Any of the MEMS flow modules described herein may be used in place of the MEMS flow module 222. The position of the MEMS flow module 222 and the inner housing 218 are at least generally depicted within the outer housing 214 in FIG. 8B to show the relative positioning of these components in the assembled condition—not to convey that the outer housing 214 needs to be in the form of a transparent structure. All details of the MEMS flow module 222 and the inner housing 218 are not necessarily illustrated in FIG. 8B.

The MEMS flow module 222 is only schematically represented in FIGS. 8A-B, and provides at least one of a filtering function and a pressure regulation function. The MEMS flow module 222 may be of any appropriate design, size, shape, and configuration, and further may be formed from any material or combination of materials that are appropriate for use by the relevant microfabrication technology. Any appropriate coating or combination of coatings may be applied to exposed surfaces of the MEMS flow module 222 as well. For instance, a coating may be applied to improve the biocompatibility of the MEMS flow module 222, to make the exposed surfaces of the MEMS flow module 222 more hydrophilic, to reduce the potential for the MEMS flow module 222 causing any biofouling, or any combination thereof. In one embodiment, a self-assembled monolayer coating (e.g., poly-ethylene-glycol) is applied in any appropriate manner (e.g., liquid or vapor phase, with vapor phase being the preferred technique) to all exposed surfaces of the MEMS flow module 222. The main requirement of the MEMS flow module 222 is that it is a MEMS device.

The primary function of the outer housing 214 and inner housing 218 is to provide structural integrity for the MEMS flow module 222 or to support the MEMS flow module 222, and further to protect the MEMS flow module 222. In this regard, the outer housing 214 and inner housing 218 each will typically be in the form of a structure that is sufficiently rigid to protect the MEMS flow module 222 from being damaged by the forces that reasonably could be expected to be exerted on the flow assembly 210 during its assembly, as well as during use of the flow assembly 210 in the application for which it was designed.

The inner housing 218 includes a hollow interior or a flow path 220 that extends through the inner housing 218 (between its opposite ends in the illustrated embodiment). The MEMS flow module 222 may be disposed within the flow path 220 through the inner housing 218 in any appropriate manner and at any appropriate location within the inner housing 218 (e.g., at any location so that the inner housing 218 is disposed about the MEMS flow module 222). Preferably, the MEMS flow module 222 is maintained in a fixed position relative to the inner housing 218. For instance, the MEMS flow module 222 may be attached or bonded to an inner sidewall or a flange formed on this inner sidewall of the inner housing 218, a press-fit could be provided between the inner housing 218 and the MEMS flow module 222, or a combination thereof. The MEMS flow module 222 also could be attached to an end of the inner housing 218 in the manner of the embodiment of FIGS. 10A-B that will be discussed in more detail below.

The inner housing 218 is at least partially disposed within the outer housing 214 (thereby encompassing having the outer housing 214 being disposed about the inner housing 218 along the entire length of the inner housing 218, or only along a portion of the length of the inner housing 218). In this regard, the outer housing 214 includes a hollow interior 216 for receiving the inner housing 218, and possibly to provide other appropriate functionality (e.g., a flow path fluidly connected with the flow path 220 through the inner housing 218). The outer and inner sidewalls of the outer housing 214 may be cylindrical or of any other appropriate shape, as may be the outer and inner sidewalls of the inner housing 218. The inner housing 218 may be retained relative to the outer housing 214 in any appropriate manner. For instance, the inner housing 218 may be attached or bonded to an inner sidewall of the outer housing 214, a press-fit could be provided between the inner housing 218 and the outer housing 214, a shrink fit could be provided between the outer housing 214 and the inner housing 218, or a combination thereof.

The inner housing 218 is likewise only schematically represented in FIGS. 8A-B, and it may be of any appropriate shape/configuration, of any appropriate size, and formed from any material or combination of materials (e.g., polymethylmethacrylate (PMMA), ceramics, silicon, titanium, and other implantable metals and plastics). Typically its outer contour will be adapted to match the inner contour of the outer housing 214 in which it is at least partially disposed. In one embodiment, the illustrated cylindrical configuration for the inner housing 218 is achieved by cutting an appropriate length from hypodermic needle stock. The inner housing 218 also may be microfabricated into the desired/required shape (e.g., using at least part of a LIGA process). However, any way of making the inner housing 218 may be utilized. It should also be appreciated that the inner housing 218 may include one or more coatings as desired/required as well (e.g., an electroplated metal; a coating to improve the biocompatibility of the inner housing 218, to make the exposed surfaces of the inner housing 218 more hydrophilic, to reduce the potential for the inner housing 218 causing any bio-fouling, or any combination thereof). In one embodiment, a self-assembled monolayer coating (e.g., poly-ethylene-glycol) is applied in any appropriate manner (e.g., liquid or vapor phase, with vapor phase being the preferred technique) to all exposed surfaces of the inner housing 218.

The outer housing 214 likewise is only schematically represented in FIGS. 8A-B, and it may be of any appropriate shape/configuration, of any appropriate size, and formed from any material or combination of materials (e.g., polymethylmethacrylate (PMMA), ceramics, silicon, titanium, and other implantable metals and plastics). Typically its outer contour will be adapted to match the inner contour of the housing or conduit in which it is at least partially disposed or otherwise mounted. The outer housing 214 also may be microfabricated into the desired/required shape (e.g., using at least part of a LIGA process). However, any way of making the outer housing 214 may be utilized. It should also be appreciated that the outer housing 214 may include one or more coatings as desired/required as well (e.g., an electroplated metal; a coating to improve the biocompatibility of the outer housing 214, to make the exposed surfaces of the outer housing 214 more hydrophilic, to reduce the potential for the outer housing 214 causing any bio-fouling, or any combination thereof). In one embodiment, a self-assembled monolayer coating (e.g., poly-ethylene-glycol) is applied in any appropriate manner (e.g., liquid or vapor phase, with vapor phase being the preferred technique) to all exposed surfaces of the outer housing 214.

Figure 9A:
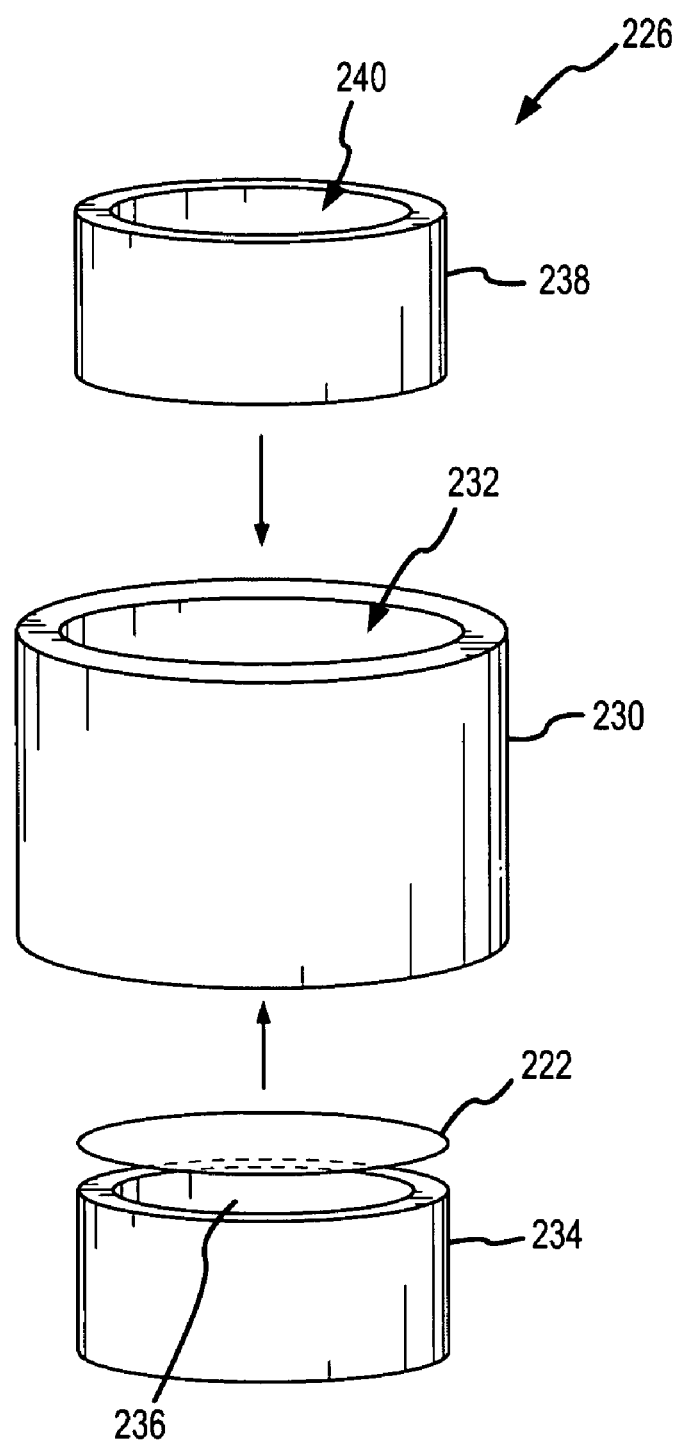
FIG. 9A is an exploded, perspective of another embodiment of a flow assembly that uses a MEMS flow module.
Figures 9B, 10B:
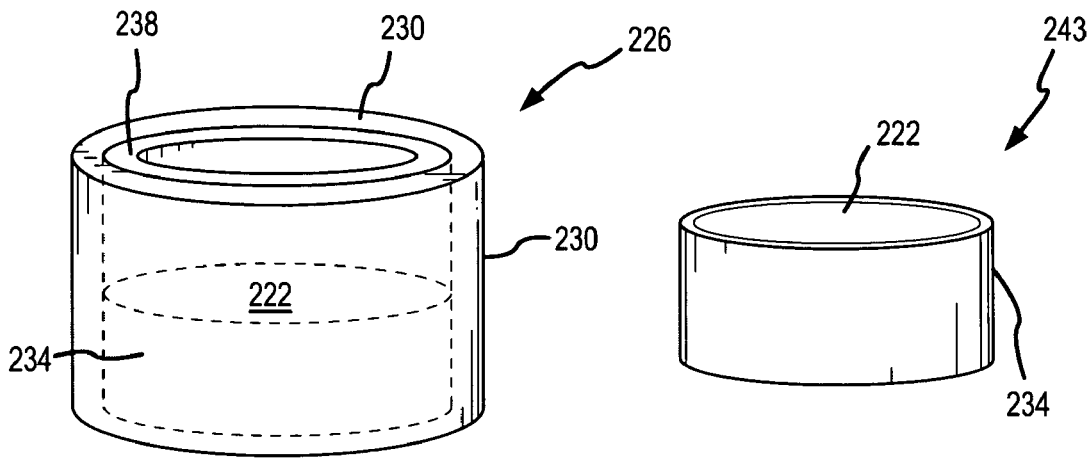
FIG. 9B is a perspective view of the flow assembly of FIG. 9A in an assembled condition.
FIG. 10B is a perspective view of the flow assembly of FIG. 10A in an assembled condition.

Another embodiment of a flow assembly is illustrated in FIGS. 9A-B (only schematic representations), and is identified by reference numeral 226. The flow assembly 226 may be used for any appropriate application (e.g., the flow assembly 226 may be disposed in a flow of any type, may be used to filter and/or control the flow of a fluid of any type, may be located in a conduit that fluidly interconnects multiple sources of any appropriate type (e.g., multiple fluid or pressure sources (including where one is the environment), such as a man-made reservoir, a biological reservoir, the environment, or any other appropriate source), or any combination thereof). The above-noted applications for the flow assembly 210 are equally applicable to the flow assembly to 226. The types of coatings discussed above in relation to the flow assembly 210 may be used by the flow assembly 226 as well.

Components of the flow assembly 226 include an outer housing 230, a first inner housing 234, a second inner housing 238, and the MEMS flow module 222. The MEMS flow 222 and the inner housings 234, 238 are at least generally depicted within the outer housing 230 in FIG. 9B to show the relative positioning of these components in the assembled condition—not to convey that the outer housing 230 needs to be in the form of a transparent structure. All details of the MEMS flow module 222 and the inner housings 234, 238 are not necessarily illustrated in FIG. 9B.

The primary function of the outer housing 230, first inner housing 234, and second inner housing 238 is to provide structural integrity for the MEMS flow module 222 or to support the MEMS flow module 222, and further to protect the MEMS flow module 222. In this regard, the outer housing 230, first inner housing 234, and second inner housing 238 each will typically be in the form of a structure that is sufficiently rigid to protect the MEMS flow module 222 from being damaged by the forces that reasonably could be expected to be exerted on the flow assembly 226 during its assembly, as well as during use of the flow assembly 226 in the application for which it was designed.

The first inner housing 234 includes a hollow interior or a flow path 236 that extends through the first inner housing 234. Similarly, the second inner housing 238 includes a hollow interior or a flow path 240 that extends through the second inner housing 238. The first inner housing 234 and the second inner housing 238 are disposed in end-to-end relation, with the MEMS flow module 222 being disposed between adjacent ends of the first inner housing 234 and the second inner housing 238. As such, a flow progressing through the first flow path 236 to the second flow path 240, or vice versa, passes through the MEMS flow module 222.

Preferably, the MEMS flow module 222 is maintained in a fixed position relative to each inner housing 234, 238, and its perimeter does not protrude beyond the adjacent sidewalls of the inner housings 234, 238 in the assembled and joined condition. For instance, the MEMS flow module 222 may be bonded to at least one of, but more preferably both of, the first inner housing 234 (more specifically one end thereof) and the second inner housing 238 (more specifically one end thereof) to provide structural integrity for the MEMS flow module 222 (e.g., using cyanoacrylic esters, thermal bonding, UV-curable epoxies, or other epoxies). Another option would be to fix the position the MEMS flow module 222 in the flow assembly 226 at least primarily by fixing the position of each of the inner housings 234, 238 relative to the outer housing 230 (i.e., the MEMS flow module 222 need not necessarily be bonded to either of the housings 234, 238). In one embodiment, an elastomeric material may be disposed between the MEMS flow module 222 and the first inner housing 234 to allow the first inner housing 234 with the MEMS flow module 222 disposed thereon to be pushed into the outer housing 230 (e.g., the elastomeric material is sufficiently "tacky" to at least temporarily retain the MEMS flow module 222 in position relative to the first inner housing 234 while being installed in the outer housing 230). The second inner housing 238 also may be pushed into the outer housing 230 (before, but more likely after, the first inner housing 234 is disposed in the outer housing 230) to "sandwich" the MEMS flow module 222 between the inner housings 234, 238 at a location that is within the outer housing 230 (i.e., such that the outer housing 230 is disposed about MEMS flow module 222). The MEMS flow module 222 would typically be contacted by both the first inner housing 234 and the second inner housing 238 when disposed within the outer housing 230. Fixing the position of each of the first inner housing 234 and the second inner housing 238 relative to the outer housing 230 will thereby in effect fix the position of the MEMS flow module 222 relative to the outer housing 230. Both the first inner housing 234 and second inner housing 238 are at least partially disposed within the outer housing 230 (thereby encompassing the outer housing 230 being disposed about either or both housings 234, 238 along the entire length thereof, or only along a portion of the length of thereof), again with the MEMS flow module 222 being located between the adjacent ends of the first inner housing 234 and the second inner housing 238. In this regard, the outer housing 230 includes a hollow interior 232 for receiving at least part of the first inner housing 234, at least part of the second inner housing 238, and the MEMS flow module 222 disposed therebetween, and possibly to provide other appropriate functionality (e.g., a flow path fluidly connected with the flow paths 236, 240 through the first and second inner housings 234, 238, respectively). The outer and inner sidewalls of the outer housing 230 may be cylindrical or of any other appropriate shape, as may be the outer and inner sidewalls of the inner housings 234, 238. Both the first inner housing 234 and the second inner housing 238 may be secured to the outer housing 230 in any appropriate manner, including in the manner discussed above in relation to the inner housing 218 and the outer housing 214 of the embodiment of FIGS. 8A-B.

Each inner housing 234, 238 is likewise only schematically represented in FIGS. 9A-B, and each may be of any appropriate shape/configuration, of any appropriate size, and formed from any material or combination of materials in the same manner as the inner housing 218 of the embodiment of FIGS. 7-8. Typically the outer contour of both housings 234, 238 will be adapted to match the inner contour of the outer housing 230 in which they are at least partially disposed. In one embodiment, the illustrated cylindrical configuration for the inner housings 234, 238 is achieved by cutting an appropriate length from hypodermic needle stock. The inner housings 234, 238 each also may be microfabricated into the desired/required shape (e.g., using at least part of a LIGA process). However, any way of making the inner housings 234, 238 may be utilized. It should also be appreciated that the inner housings 234, 238 may include one or more coatings as desired/required as well in accordance with the foregoing.

The outer housing 230 is likewise only schematically represented in FIGS. 9A-B, and it may be of any appropriate shape/configuration, of any appropriate size, and formed from any material or combination of materials in the same manner as the outer housing 214 of the embodiment of FIGS. 8A-B. Typically the outer contour of the outer housing 230 will be adapted to match the inner contour of the housing or conduit in which it is at least partially disposed or otherwise mounted. The outer housing 230 may be microfabricated into the desired/required shape (e.g., using at least part of a LIGA process). However, any way of making the outer housing 230 may be utilized. It should also be appreciated that the outer housing 230 may include one or more coatings as desired/required in accordance with the foregoing.

Another embodiment of a flow assembly is illustrated in FIGS. 10A-B (only schematic representations), and is identified by reference numeral 243. The flow assembly 243 may be used for any appropriate application (e.g., the flow assembly 243 may be disposed in a flow of any type, may be used to filter and/or control the flow of a fluid of any type, may be located in a conduit that fluidly interconnects multiple sources of any appropriate type (e.g., between multiple fluid or pressure sources, such as a man-made reservoir, a biological reservoir, the environment, or any other appropriate source), or any combination thereof). Components of the flow assembly 243 include the above-noted housing 234 and the MEMS flow module 222 from the embodiment of FIGS. 9A-B. In the case of the flow assembly 243, the MEMS flow module 222 is attached or bonded to one end of the housing 234 (e.g., using cyanoacrylic esters, thermal bonding, UV-curable epoxies, or other epoxies). The flow assembly 243 may be disposed within an outer housing in the manner of the embodiments of FIGS. 8A-9B, or could be used "as is." The above-noted applications for the flow assembly 210 are equally applicable to the flow assembly 243. The types of coatings discussed above in relation to the flow assembly 210 may be used by the flow assembly 243 as well.

One particularly desirable application for the flow assemblies 210, 226, and 243 of FIGS. 8A-10B, as discussed above, is to regulate pressure within the anterior chamber of an eye. That is, they may be disposed in an exit path through which aqueous humor travels to treat a glaucoma patient. Preferably, the flow assemblies 210, 226, 243 each provide a bacterial filtration function to reduce the potential for developing an infection within the eye. Although the various housings and MEMS flow modules used by the flow assemblies 210, 226, and 243 each may be of any appropriate color, it may be desirable for the color to be selected so as to "blend in" with the eye to at least some extent.

Figures 11A, 11B:
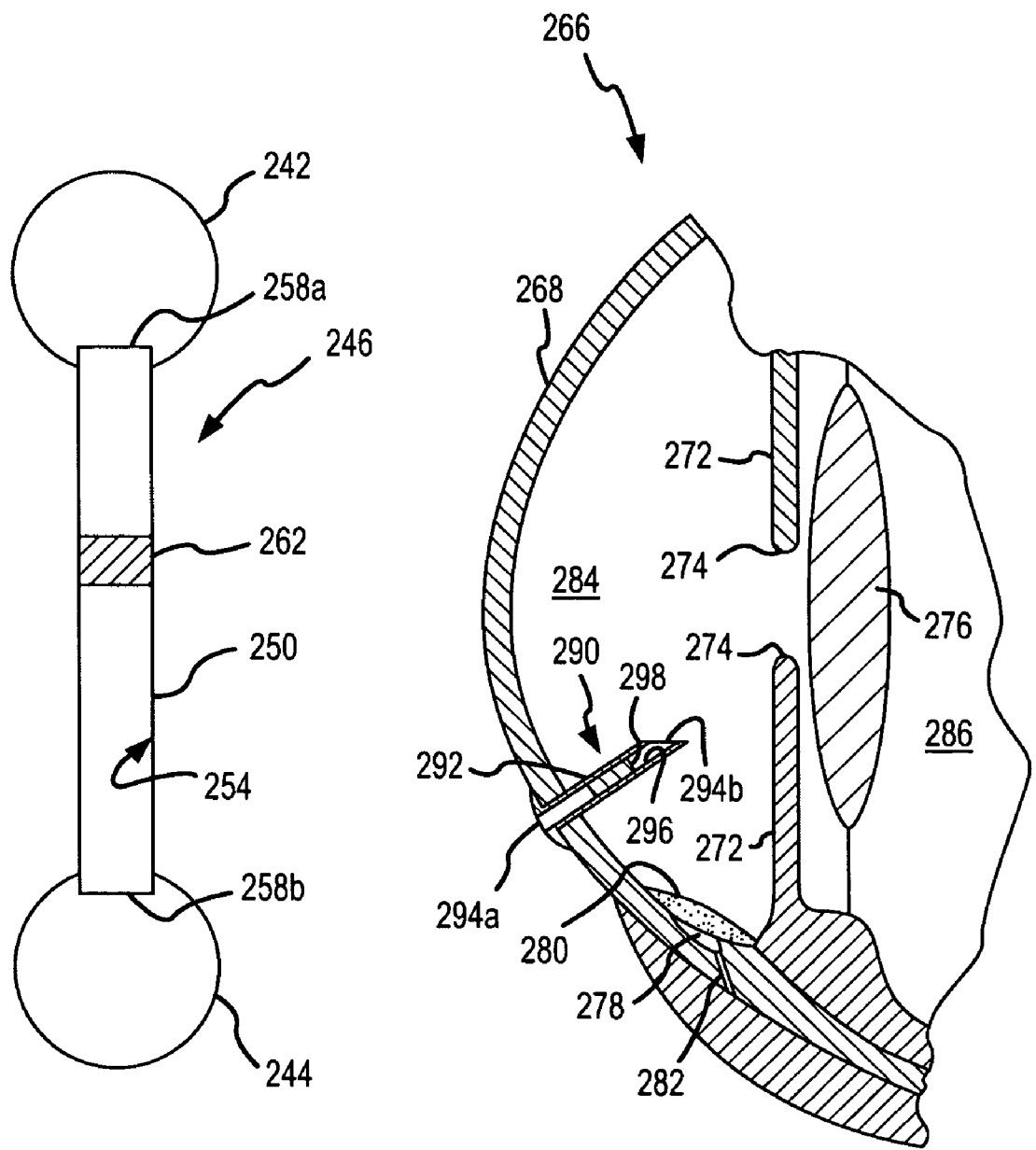
FIG. 11A is a schematic of one embodiment of a glaucoma or intraocular implant that may use any of the MEMS flow modules described herein.
FIG. 11B is a cross-sectional view of one embodiment of glaucoma or intraocular implant or shunt that is used to relieve pressure within the anterior chamber of the eye, and that may utilize any of the MEMS flow modules described herein.

An example of the above-noted application is schematically illustrated in FIG. 11A. Here, an anterior chamber 242 of a patient's eye (or other body region for that matter—a first body region) is fluidly interconnected with an appropriate drainage area 244 by an implant 246 (a "glaucoma implant" for the specifically noted case). The drainage area 244 may be any appropriate location, such as externally of the eye (e.g., on an exterior surface of the cornea), within the eye (e.g., Schlemm's canal), or within the patient's body in general (a second body region).

Generally, the implant 246 includes a conduit 250 having a pair of ends 258a, 258b, with a flow path 254 extending therebetween. The size, shape, and configuration of the conduit 250 may be adapted as desired/required, including to accommodate the specific drainage area 244 being used. Representative configurations for the conduit 250 are disclosed in U.S. Patent Application Publication No. 2003/0212383, as well as U.S. Pat. Nos. 3,788,327; 5,743,868; 5,807,302; 6,626,858; 6,638,239; 6,533,768; 6,595,945; 6,666,841; and 6,736,791, the entire disclosures of which are incorporated by reference in their entirety herein.

A flow assembly 262 is disposed within the flow path 254 of the conduit 250. All flow leaving the anterior chamber 242 through the implant 246 is thereby directed through the flow assembly 262. Similarly, any flow from the drainage area 244 into the implant 246 will have to pass through the flow assembly 262. The flow assembly 262 may be retained within the conduit 250 in any appropriate manner and at any appropriate location (e.g., it could be disposed on either end 258a, 258b, or any intermediate location therebetween). The flow assembly 262 may be in the form of any of the flow assemblies 210, 226, or 243 discussed above, replacing the MEMS flow module 222 with any of the MEMS flow modules in accordance with FIGS. 2A-7. Alternatively, the flow assembly 262 could simply be in the form of the MEMS flow modules in accordance with FIGS. 2A-7. Any appropriate coating may be applied to at least those surfaces of the implant 246 that would be exposed to biological material/fluids, including without limitation a coating that improves biocompatibility, that makes such surfaces more hydrophilic, and/or that reduces the potential for bio-fouling. In one embodiment, a self-assembled monolayer coating (e.g., poly-ethylene-glycol) is applied in any appropriate manner (e.g., liquid or vapor phase, with vapor phase being the preferred technique) to the noted surfaces.

FIG. 11B illustrates a representative embodiment in accordance with FIG. 11A. Various portions of the eye 266 are identified in FIG. 11B, including the cornea 268, iris 272, pupil 274, lens 276, anterior chamber 284, vitreous body 286, Schlemm's canal 278, trabecular meshwork 280, and aqueous veins 282. Here, an implant or shunt 290 having an appropriately-shaped conduit 292 is directed through the cornea 268. The conduit 292 may be in any appropriate form, but will typically include at least a pair of ends 294a, 294b, as well as a flow path 296 extending therebetween. End 294a is disposed on the exterior surface of the cornea 268, while end 294b is disposed within the anterior chamber 284 of the eye 266.

A flow assembly 298 is disposed within the flow path 296 of the conduit 292. All flow leaving the anterior chamber 284 through the shunt 290 is thereby directed through the flow assembly 298. Similarly, any flow from the environment back into the shunt 290 will have to pass through the flow assembly 298 as well. Preferably, the flow assembly 298 provides a bacterial filtration function to reduce the potential for developing an infection within the eye when using the implant 290. The flow assembly 298 may be retained within the conduit 292 in any appropriate manner and at any appropriate location (e.g., it could be disposed on either end 294a, 294b, or any an intermediate location therebetween). The flow assembly 298 may be in the form of any of the flow assemblies 210, 226, or 243 discussed above, replacing the MEMS flow module 222 with any of the MEMS flow modules in accordance with FIGS. 2A-7. Alternatively, the flow assembly 298 could simply be in the form of the MEMS flow modules in accordance with FIGS. 2A-7. Any appropriate coating may be applied to at least those surfaces of the shunt 290 that would be exposed to biological material/fluids, including without limitation a coating that improves biocompatibility, that makes such surfaces more hydrophilic, and/or that reduces the potential for bio-fouling. In one embodiment, a self-assembled monolayer coating (e.g., poly-ethylene-glycol) is applied in any appropriate manner (e.g., liquid or vapor phase, with vapor phase being the preferred technique) to the noted surfaces.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An implant for addressing pressure within a first body region, said implant comprising:
   a conduit comprising a flow path and adapted to fluidly interconnect with the first body region; and
   a MEMS flow module associated with said flow path, wherein said MEMS flow module comprises:
   a first plate comprising a first flow port;
   a second plate comprising a second flow port, wherein said second plate is spaced from and structurally interconnected with said first plate; and
   a first flow-restricting structure extending from one of said first and second plates at least toward the other of said first and second plates, wherein a spacing between said first flow-restricting structure and the other of said first and second plates defines a first flow restriction, and wherein at least one dimension of said first flow restriction changes based upon at least one of said first and second plates flexing in response to a development of at least a certain differential pressure across said MEMS flow module;
   wherein said first plate comprises a first region and a second region that extends from said first region to a perimeter of said first plate, wherein said second plate comprises a third region and a fourth region that extends from said third region to a perimeter of said second plate, wherein said second region of said first plate comprises a plurality of said first flow ports, wherein said third region of said second plate comprises a plurality of said second flow ports, wherein a first link extends between said first and second plates and interfaces with said first plate within said first region and interfaces with said second plate within said third region, and wherein said fourth region of said second plate is at least substantially maintained in a fixed orientation.

2. The implant of claim 1, the first body region is an anterior chamber of an eye.

3. The implant of claim 1, wherein each of said first and second plates comprises at least one layer, and wherein each said layer has a thickness within a range of about 1 micron to about 3 microns.

4. The implant of claim 1, wherein a flow rate through said MEMS flow module increases based upon said at least one dimension of said first flow restriction changing.

5. The implant of claim 1, wherein at least one dimension of said first flow restriction changes based upon said at least one of said first and second plates flexing in response to a development of any differential pressure greater than zero across said MEMS flow module.

6. The implant of claim 1 wherein said first region is centrally located in relation to said first plate.

7. The implant of claim 1 wherein said second plate is spaced from said first plate in a first direction, wherein said second region of said first plate flexes relative to said first region of said first plate in a second direction in response to said development of said at least a certain differential pressure across said MEMS flow module to change said at least one dimension of said first flow restriction, and wherein said second direction is opposite of said first direction.

8. The implant of claim 7, wherein an entirety of said second plate is at least substantially maintained in a fixed orientation.

9. The implant of claim 7, wherein said third region of said second plate flexes relative to said fourth region of said second plate and in said second direction in response to said development of said at least a certain differential pressure across said MEMS flow module to change said at least one dimension of said first flow restriction.

10. The implant of claim 7, wherein a first surface of said first plate, that is opposite a second surface of said first plate that faces said second plate, becomes at least generally cup-shaped when said second region of said first plate flexes in said second direction.

11. The implant of claim 1, wherein said second plate is spaced from said first plate in a first direction, wherein said first plate is at least substantially maintained in a fixed orientation, wherein said third region of said second plate flexes relative to said fourth region of said second plate and in a second direction in response to said development of said at least a certain differential pressure across said MEMS flow module to change said at least one dimension of said first flow restriction, and wherein said second direction is opposite of said first direction.

12. The implant of claim 1, wherein said MEMS flow module comprises a first fabrication level comprising said first plate and said first flow-restricting structure, as well as a second fabrication level comprising said second plate, and wherein said first flow-restricting structure extends from said first plate at least toward said second plate.

13. The implant of claim 1, wherein said MEMS flow module comprises a first fabrication level comprising said first plate, as well as a second fabrication level comprising said second plate and said first flow-restricting structure, and wherein said first flow-restricting structure extends from said second plate at least toward said first plate.

14. The implant of claim 1, wherein said perimeter of said first plate is disposed inwardly of said perimeter of said second plate.

15. The implant of claim 1, wherein a projection of said first plate onto said second plate defines a region that encompasses each of said plurality of second flow ports, and wherein an entirety of said perimeter of said second plate is disposed outwardly from said region.

16. The implant of claim 1, wherein said first flow-restricting structure is disposed about said first flow port, extends from said first plate in a direction of said second plate, and remains spaced from said second plate, and wherein at least part of said second flow port is disposed beyond a projection of said first flow-restricting structure onto said second plate.

17. The implant of claim 16, further comprising a plurality of said second flow ports.

18. The implant of claim 16, wherein said second plate is spaced from said first plate in a first direction, wherein said second region of said second plate flexes at least generally in said first direction in response to said development of said at least a certain differential pressure across said MEMS flow module to change said at least one dimension of said first flow restriction.

19. The implant of claim 16, wherein said second plate is spaced from said first plate in a first direction, wherein said second region of said first plate flexes at least generally in a second direction in response to said development of said at least a certain differential pressure across said MEMS flow module to change said at least one dimension of said first flow restriction, wherein said second direction is opposite of said first direction.

20. The implant of claim 16, wherein said MEMS flow module comprises a first fabrication level comprising said first plate and said first flow-restricting structure, as well as a second fabrication level comprising said second plate, and wherein said first flow-restricting structure extends from said first plate at least toward said second plate.

21. The implant of claim 1, wherein said first flow-restricting structure extends from said first plate and terminates prior to reaching said second plate.

22. The implant of claim 1, further comprising a plurality of said first flow-restricting structures, each having a corresponding said first flow restriction.

23. The implant of claim 22, wherein each of said plurality of said first flow-restricting structures is annular, and wherein said plurality of said first flow-restricting structures are concentrically disposed.

24. The implant of claim 22 wherein said second and fourth regions of each of said first and second plates, respectively, is maintained in an at least substantially fixed orientation, wherein at least one said first flow-restricting structure extends from said second or fourth region of said one of said first and second plates, wherein at least one said first flow-restricting structure extends from said first or third region of said one of said first and second plates, wherein each said first flow restriction associated with said second or fourth region of either said first or second plate is of a fixed magnitude, and wherein each said first flow restriction associated with said first or third region of either said first or second plate is adjustable by said flexing.

25. The implant of claim 22, wherein each of said plurality of first flow-restricting structures is annular, and wherein none of said plurality of first flow-restricting structures encompass a common region.

26. The implant of claim 22, said first flow restriction for at least two of said first flow-restricting structures are of a different size after said at least one of said first and second plates flexes in response to said development of said at least a certain differential pressure across said MEMS flow module.

27. The implant of claim 1, wherein said first flow-restricting structure is annular.

28. The implant of claim 1, wherein said first flow-restricting structure is in the form of a solid plug.

29. An implant for addressing pressure within a first body region, said implant comprising:
a conduit comprising a flow path and adapted to fluidly interconnect with the first body region; and
a MEMS flow module associated with said flow path, wherein said MEMS flow module comprises:

a first plate comprising first and second regions, wherein said first region of said first plate is disposed about said second region of said first plate, wherein said first and second regions each comprise a plurality of first flow ports, wherein said first region of said first plate comprises at least one first flow-restricting structure, and wherein said second region of said first plate comprises at least one second flow-restricting structure; and a second plate comprising first and second regions, wherein said first region of said second plate is disposed about said second region of said second plate, wherein said first and second regions of said second plate each comprise a plurality of second flow ports, wherein each of said first and second flow-restricting structures extends from said first plate at least toward said second plate, wherein a space between each said first and second flow-restricting structure defines first and second flow restrictions, respectively, wherein said first region of each of said first and second plates is maintained in an at least substantially fixed orientation, and wherein said second region of at least one of said first and second plates flexes in response to a development of at least a certain differential pressure across said MEMS flow module to change at least one dimension of at least one said second flow restriction;

wherein the first region of the first plate extends from said second region of the first plate to a perimeter of said first plate, wherein the first region of the second plate from said second region to a perimeter of said second plate, wherein a first link extends between said first and second plates and interfaces with said first plate within said second region of the first plate and interfaces with said second plate within said second region of the second plate, and wherein said first region of said second plate is at least substantially maintained in a fixed orientation.

30. The implant of claim 29 wherein said first flow-restricting structure is disposed within said second region of said one of said first and second plates.

31. The implant of claim 30, wherein said first region of said first plate comprises a plurality of said first flow ports, wherein said first region of said second plate comprises a plurality of said second flow ports, wherein said MEMS flow module further comprises a second flow-restricting structure that extends from one of said first and second plates at least toward the other of said first and second plates, and wherein an at least substantially fixed spacing exists between said second flow-restricting structure and its corresponding said other of said first and second plates.

32. The implant of claim 30, further comprising a plurality of structural interconnects extending between said first and second plates within said first region of each of said first and second plates.

33. The implant of claim 30, further comprising at least one annular wall extending between said first and second plates within said first region of each of said first and second plates.

34. The implant of claim 33, further comprising a plurality of structural interconnects extending between said first and second plates within said first region of each of said first and second plates.

35. The implant of claim 30, wherein said second plate is spaced from said first plate in a first direction, wherein said second region of said second plate flexes at least generally in said first direction in response to said development of said at least a certain differential pressure across said MEMS flow module to change said at least one dimension of said first flow restriction.

36. The implant of claim 35, wherein said second region of said first plate also flexes at least generally in said first direction in response to said development of said at least a certain differential pressure across said MEMS flow module.

37. The implant of claim 36, wherein said MEMS flow module comprises a first fabrication level comprising said first plate and said first flow-restricting structure, as well as a second fabrication level comprising said second plate, and wherein said first flow-restricting structure extends from said first plate at least toward said second plate.

38. The implant of claim 36, wherein said MEMS flow module comprises a first fabrication level comprising said first plate, as well as a second fabrication level comprising said second plate and said first flow-restricting structure, and wherein said first flow-restricting structure extends from said second plate at least toward said first plate.

39. The implant of claim 35, wherein an entirety of said first plate is at least substantially maintained in a fixed orientation.

40. The implant of claim 39, wherein said MEMS flow module comprises a first fabrication level comprising said first plate and said first flow-restricting structure, as well as a second fabrication level comprising said second plate, and wherein said first flow-restricting structure extends from said first plate at least toward said second plate.

41. The implant of claim 39, wherein said MEMS flow module comprises a first fabrication level comprising said first plate, as well as a second fabrication level comprising said second plate and said first flow-restricting structure, and wherein said first flow-restricting structure extends from said second plate at least toward said first plate.

42. The implant of claim 29, wherein all flow between any said first flow port and any said second flow port must pass through at least one said first or second flow restriction.

43. The implant of claim 29, wherein each said first and second flow-restricting structure is annular and concentrically disposed.

44. The implant of claim 29, further comprising a plurality of said first and second flow restricting structures.

* * * * *